(12) United States Patent
Yamahiro et al.

(10) Patent No.: US 7,863,396 B2
(45) Date of Patent: Jan. 4, 2011

(54) SILICON COMPOUNDS

(75) Inventors: Mikio Yamahiro, Kanagawa (JP); Hisao Oikawa, Kanagawa (JP); Kenya Ito, Kanagawa (JP); Yasuhiro Yamamoto, Kanagawa (JP); Masami Tanaka, Kanagawa (JP); Nobumasa Ootake, Kangawa (JP); Kenichi Watanabe, Kangawa (JP); Kohji Ohno, Kyoto (JP); Yoshinobu Tsujii, Kyoto (JP); Takeshi Fukuda, Kyoto (JP)

(73) Assignee: Chisso Corporation, Osaka (JP)

( * ) Notice: Subject to any disclaimer, the term of this patent is extended or adjusted under 35 U.S.C. 154(b) by 1186 days.

(21) Appl. No.: 10/548,365

(22) PCT Filed: Mar. 5, 2004

(86) PCT No.: PCT/JP2004/002809

§ 371 (c)(1),
(2), (4) Date: Oct. 19, 2005

(87) PCT Pub. No.: WO2004/078767

PCT Pub. Date: Sep. 16, 2004

(65) Prior Publication Data

US 2006/0287454 A1 Dec. 21, 2006

(30) Foreign Application Priority Data

Mar. 7, 2003 (JP) .............................. 2003-062135

(51) Int. Cl.
 *C08F 130/08* (2006.01)
(52) U.S. Cl. ...................................... 526/279; 556/464
(58) Field of Classification Search ................. 526/279; 556/464

See application file for complete search history.

(56) References Cited

U.S. PATENT DOCUMENTS 6,899,999 B2 * 5/2005 Hiraoka et al. .............. 430/311

OTHER PUBLICATIONS

Feher et al., Amine and ester-substituted silsesquioxanes: synthesis, characterization and use as a core for starburst dendrimers, Chemical Communications (Cambridge) (1998), (3), 323-324.*

Costa et al.,OrganicJInorganic Nanocomposite Star Polymers via Atom Transfer Radical Polymerization of Methyl Methacrylate Using Octafunctional Silsesquioxane Cores, Macromolecules, 34, pp. 5398-5407, 2001.*

Vohra et al., Fluoropolymer resists for 157 nm lithography, Proc. SPIE, vol. 5039, 539 (2003), Proc. SPIE, vol. 5039, 539 (2003).*

Ricardo O.R. Costa et al., "Organic/Inorganic Nanocomposite Star Polymers via Atom Transfer Radical Polymerization of Methyl Methacrylate Using Octafunctional Silsesquioxane Cores", Macromolecules, 34, pp. 5398-5407, 2001.

* cited by examiner

*Primary Examiner*—Daniel M Sullivan
*Assistant Examiner*—Chukwuma O Nwaonicha
(74) *Attorney, Agent, or Firm*—Wenderoth, Lind & Ponack, L.L.P.

(57) ABSTRACT

The present invention provides a silicon compound represented by Formula (1) and a polymer obtained by using the same, and this makes it possible not only to obtain an organic-inorganic composite material having a distinct structure but also to control the structure of the above polymer as a molecular aggregate.

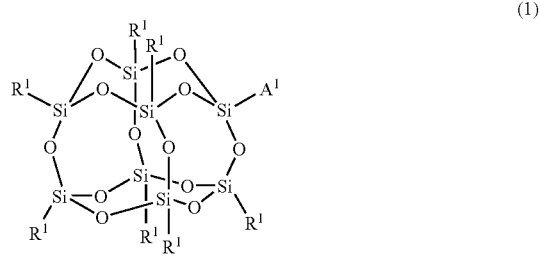

(1)

wherein $R^1$ is a group independently selected from hydrogen, alkyl having a carbon atom number of 1 to 40, substituted or non-substituted aryl and substituted or non-substituted arylalkyl; in this alkyl having a carbon atom number of 1 to 40, optional hydrogens may be substituted with fluorine, and optional —$CH_2$— may be substituted with —O—, —CH=CH—, cycloalkylene or cycloalkenylene; in alkylene in this arylalkyl, optional hydrogens may be substituted with fluorine, and optional —$CH_2$— may be substituted with —O— or —CH=CH—; and $A^1$ is a group having an α-haloester group.

27 Claims, No Drawings

SILICON COMPOUNDS

TECHNICAL FIELD

The present invention relates to a novel silicon compound characterized by having a polymerization initiating ability for addition-polymerizable monomers and a polymer obtained using the same.

RELATED ART

Polymers have come to be used in various fields not only as a general purpose structure-forming material but also as a value added type material having high-degree function and performance, and the importance of producing high molecular materials under precise design is increasing. Also in the field of organic-inorganic composite materials containing silsesquioxane as an inorganic component, it is very important to create novel functional high molecular materials. Polymers having distinct structures have to be synthesized in order to obtain such materials. A molecular property of a polymer and a property thereof as a molecular aggregate can not precisely be analyzed if it is not a polymer having a distinct structure, and therefore the performances of the high molecular material can not be optimized so that they meet the object. However, almost all of conventional organic-inorganic composite materials have not contained organic polymers having a controlled structure. A large part of them is obtained by mechanically blending silsesquioxane with organic polymers, and therefore it has been very difficult to control a structure thereof as a molecular aggregate of a complex.

Then, it has come to be tried to control a structure of a polymer by using a polymerization initiator. It is disclose in Document 1 that an α-haloester group is a good initiator for styrene base monomers and methacrylic acid base monomers in living radical polymerization. However, silsesquioxane derivatives having an α-haloester group have not so far been known up to now. It is disclose in Document 2 that silsesquioxane derivatives having a chloromethylphenethyl group are relatively good initiators for styrene base monomers in living radical polymerization.

Document 1: Chem. Rev., 101, 2921 to 2990 (2001)

Document 2: Chem. Mater., 13, 3436 to 3448 (2001)

An object of the present invention is to provide a novel silicon compound having a living radical polymerization initiating ability for addition-polymerizable monomers of a wide range and a polymer obtained using the same to thereby solve the problems described above regarding conventional organic-inorganic composite materials.

DISCLOSURE OF THE INVENTION

The present inventors have found a novel silsesquioxane derivative having an α-haloester group as a functional group. They have found that the above compound is effective as a means for solving the problems described above. That is, the present invention comprises the following structures.

[1] A silicon compound represented by Formula (1):

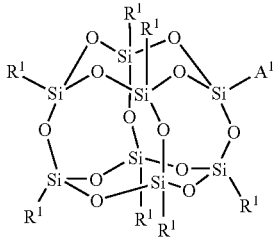

(1)

wherein $R^1$ is a group independently selected from hydrogen, alkyl having a carbon atom number of 1 to 40, substituted or non-substituted aryl and substituted or non-substituted arylalkyl; in this alkyl having a carbon atom number of 1 to 40, optional hydrogens may be substituted with fluorine, and optional —$CH_2$— may be substituted with —O—, —CH=CH—, cycloalkylene or cycloalkenylene; in alkylene in this arylalkyl, optional hydrogens may be substituted with fluorine, and optional —$CH_2$— may be substituted with —O— or —CH=CH—; and $A^1$ is a group having an α-haloester group.

[2] The silicon compound as described in the item [1], wherein $R^1$ is a group independently selected from hydrogen and alkyl having a carbon atom number of 1 to 30 in which optional hydrogens may be substituted with fluorine and in which optional —$CH_2$— may be substituted with —O— or cycloalkylene.

[3] The silicon compound as described in the item [1], wherein $R^1$ is a group independently selected from alkenyl having a carbon atom number of 1 to 20 in which optional hydrogens may be substituted with fluorine and in which optional —$CH_2$— may be substituted with —O— or cycloalkylene and alkyl having a carbon atom number of 1 to 20 in which optional hydrogens may be substituted with fluorine and in which at least one —$CH_2$— is substituted with cycloalkenylene.

[4] The silicon compound as described in the item [1], wherein $R^1$ is a group independently selected from non-substituted naphthyl and phenyl in which optional hydrogens may be substituted with halogen or alkyl having a carbon atom number of 1 to 10; and in the alkyl which is a substituent for the phenyl, optional hydrogens may be substituted with fluorine, and optional —$CH_2$— may be substituted with —O—, —CH=CH—, cycloalkylene or phenylene.

[5] The silicon compound as described in the item [1], wherein $R^1$ is a group independently selected from phenylalkyls constituted from phenyl in which optional hydrogens may be substituted with halogen or alkyl having a carbon atom number of 1 to 12 and alkylene having a carbon atom number of 1 to 12 in which optional hydrogens may be substituted with fluorine and in which optional —$CH_2$— may be substituted with —O— or —CH=CH—; and in the alkyl which is a substituent for the phenyl, optional hydrogens may be substituted with fluorine, and optional —$CH_2$— may be substituted with —O—, —CH=CH—, cycloalkylene or phenylene.

[6] The silicon compound as described in the item [1], wherein $R^1$ is a group independently selected from alkyl having a carbon atom number of 1 to 8 in which optional hydrogens may be substituted with fluorine and in which optional —$CH_2$— may be substituted with —O—, —CH=CH—, cycloalkylene or cycloalkenylene, phenyl in which optional hydrogens may be substituted with halogen, methyl or methoxy, non-substituted naphthyl and phenylalkyl constituted from phenyl in which optional hydrogens may be substituted with fluorine, alkyl having a carbon atom number of 1 to 4, vinyl or methoxy and alkylene which has a carbon atom number of 1 to 8 and in which optional —$CH_2$— may be substituted with —O— or —CH=CH—.

[7] The silicon compound as described in the item [1], wherein all $R^1$'s are the same group selected from alkyl having a carbon atom number of 1 to 8 in which optional hydrogens may be substituted with fluorine and in which optional —$CH_2$— may be substituted with —O—, —CH═CH—, cycloalkylene or cycloalkenylene, phenyl in which optional hydrogens may be substituted with halogen, methyl or methoxy, non-substituted naphthyl and phenylalkyl constituted from phenyl in which optional hydrogens may be substituted with fluorine, alkyl having a carbon atom number of 1 to 4, vinyl or methoxy and alkylene which has a carbon atom number of 1 to 8 and in which optional —CH$_2$— may be substituted with —O— or —CH═CH—.

[8] The silicon compound as described in the item [1], wherein all R$^1$'s are the same group selected from phenyl in which optional hydrogens may be substituted with halogen, methyl or methoxy, non-substituted naphthyl and phenylalkyl constituted from phenyl in which optional hydrogens may be substituted with fluorine, alkyl having a carbon atom number of 1 to 4, vinyl or methoxy and alkylene which has a carbon atom number of 1 to 8 and in which optional —CH$_2$— may be substituted with —O—.

[9] The silicon compound as described in the item [1], wherein all R$^1$'s are the same group selected from ethyl, 2-methylpropyl, 2,4,4-trimethylpentyl, cyclopentyl, cyclohexyl, non-substituted phenyl, 3,3,3-trifluoropropyl and tridecafluoro-1,1,2,2-tetrahydrooctyl.

[10] The silicon compound as described in the item [1], wherein all R$^1$'s are the same group selected from non-substituted phenyl and 3,3,3-trifluoropropyl.

[11] The silicon compound as described in the item [1], wherein in Formula (1), R$^1$ is a group independently selected from hydrogen, alkyl having a carbon atom number of 1 to 40, substituted or non-substituted aryl and substituted or non-substituted arylalkyl; in this alkyl having a carbon atom number of 1 to 40, optional hydrogens may be substituted with fluorine, and optional —CH$_2$— may be substituted with —O—, —CH═CH—, cycloalkylene or cycloalkenylene; in alkylene in this arylalkyl, optional hydrogens may be substituted with fluorine, and optional —CH$_2$— may be substituted with —O— or —CH═CH—; and A$^1$ is a group represented by Formula (2):

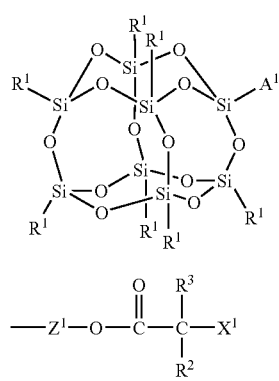

(1)

(2)

in Formula (2), X$^1$ is halogen; R$^2$ is alkyl having a carbon atom number of 1 to 20, aryl having a carbon atom number of 6 to 20 or aralkyl having a carbon atom number of 7 to 20; R$^3$ is hydrogen, alkyl having a carbon atom number of 1 to 20, aryl having a carbon atom number of 6 to 20 or aralkyl having a carbon atom number of 7 to 20; Z$^1$ is alkylene having a carbon atom number of 1 to 20 or alkenylene having a carbon atom number of 3 to 8; and in these alkylene and alkenylene, optional —CH$_2$— may be substituted with —O—.

[12] The silicon compound as described in the item [11], wherein R$^1$ is a group independently selected from hydrogen and alkyl having a carbon atom number of 1 to 30 in which optional hydrogens may be substituted with fluorine and in which optional —CH$_2$— may be substituted with —O— or cycloalkylene.

[13] The silicon compound as described in the item [11], wherein R$^1$ is a group independently selected from alkenyl having a carbon atom number of 1 to 20 in which optional hydrogens may be substituted with fluorine and in which optional —CH$_2$— may be substituted with —O— or cycloalkylene and alkyl having a carbon atom number of 1 to 20 in which optional hydrogens may be substituted with fluorine and in which at least one —CH$_2$— is substituted with cycloalkenyl.

[14] The silicon compound as described in the item [11], wherein R$^1$ is a group independently selected from non-substituted naphthyl and phenyl in which optional hydrogens may be substituted with halogen or alkyl having a carbon atom number of 1 to 10; and in the alkyl which is a substituent for the phenyl, optional hydrogens may be substituted with fluorine, and optional —CH$_2$— may be substituted with —O—, —CH═CH—, cycloalkylene or phenylene.

[15] The silicon compound as described in the item [11], wherein R$^1$ is a group independently selected from phenylalkyls constituted from phenyl in which optional hydrogens may be substituted with halogen or alkyl having a carbon atom number of 1 to 12 and alkylene having a carbon atom number of 1 to 12 in which optional hydrogens may be substituted with fluorine and in which optional —CH$_2$— may be substituted with —O— or —CH═CH—; and in the alkyl which is a substituent for the phenyl, optional hydrogens may be substituted with fluorine, and optional —CH$_2$— may be substituted with —O—, —CH═CH—, cycloalkylene or phenylene.

[16] The silicon compound as described in the item [11], wherein R$^1$ is a group independently selected from alkyl having a carbon atom number of 1 to 8 in which optional hydrogens may be substituted with fluorine and in which optional —CH$_2$— may be substituted with —O—, —CH═CH—, cycloalkylene or cycloalkenylene, phenyl in which optional hydrogens may be substituted with halogen, methyl or methoxy, non-substituted naphthyl and phenylalkyl constituted from phenyl in which optional hydrogens may be substituted with fluorine, alkyl having a carbon atom number of 1 to 4, vinyl or methoxy and alkylene which has a carbon atom number of 1 to 8 and in which optional —CH$_2$— may be substituted with —O— or —CH═CH—.

[17] The silicon compound as described in the item [11], wherein all R$^1$'s are the same group selected from alkyl having a carbon atom number of 1 to 8 in which optional hydrogens may be substituted with fluorine and in which optional —CH$_2$— may be substituted with —O—, —CH═CH—, cycloalkylene or cycloalkenylene, phenyl in which optional hydrogens may be substituted with halogen, methyl or methoxy, non-substituted naphthyl and phenylalkyl constituted from phenyl in which optional hydrogens may be substituted with fluorine, alkyl having a carbon atom number of 1 to 4, vinyl or methoxy and alkylene which has a carbon atom number of 1 to 8 and in which optional —CH$_2$— may be substituted with —O— or —CH═CH—.

[18] The silicon compound as described in the item [11], wherein all R$^1$'s are the same group selected from phenyl in which optional hydrogens may be substituted with halogen, methyl or methoxy, non-substituted naphthyl and phenylalkyl constituted from phenyl in which optional hydrogens may be substituted with fluorine, alkyl having a carbon atom number of 1 to 4, vinyl or methoxy and alkylene which has a carbon atom number of 1 to 8 and in which optional —CH$_2$— may be substituted with —O—.

[19] The silicon compound as described in the item [11], wherein all R$^1$'s are the same group selected from ethyl, 2-methylpropyl, 2,4,4-trimethylpentyl, cyclopentyl, cyclohexyl, non-substituted phenyl, 3,3,3-trifluoropropyl and tridecafluoro-1,1,2,2-tetrahydrooctyl.

[20] The silicon compound as described in the item [11], wherein all R$^1$'s are the same group selected from non-substituted phenyl and 3,3,3-trifluoropropyl.

[21] The silicon compound as described in the item [11], wherein Z$^1$ is alkylene which has a carbon atom number of 1 to 20 and in which optional —CH$_2$— may be substituted with —O—.

[22] The silicon compound as described in the item [11], wherein Z$^1$ is —C$_2$H$_4$—O—C$_3$H$_6$—, —C$_3$H$_6$— or —C$_2$H$_4$—; R$^2$ is methyl or ethyl; R$^3$ is hydrogen, methyl or ethyl; and X$^1$ is bromine.

[23] The silicon compound as described in the item [11], wherein Z$^1$ is —C$_3$H$_6$— or —C$_2$H$_4$—; both of R$^2$ and R$^3$ are methyl; and X$^1$ is bromine.

[24] A production process for the silicon compound represented by Formula (1) as described in the item [1], characterized by reacting a compound represented by Formula (3) with acid halide having a halogenated alkyl group:

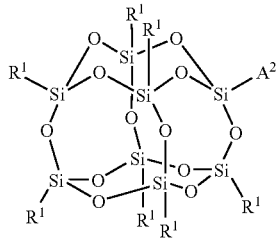
(3)

wherein R$^1$ is a group independently selected from hydrogen, alkyl having a carbon atom number of 1 to 40, substituted or non-substituted aryl and substituted or non-substituted arylalkyl; in this alkyl having a carbon atom number of 1 to 40, optional hydrogens may be substituted with fluorine, and optional —CH$_2$— may be substituted with —O—, —CH═CH—, cycloalkylene or cycloalkenylene; in alkylene in this arylalkyl, optional hydrogens may be substituted with fluorine, and optional —CH$_2$— may be substituted with —O— or —CH═CH—; and A$^2$ is an organic group having a hydroxyl group at an end.

[25] A production process for a silicon compound represented by Formula (6), characterized by reacting a compound represented by Formula (4) with a compound represented by Formula (5):

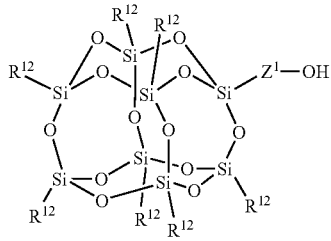
(4)

wherein all R$^{12}$'s are the same group selected from alkyl having a carbon atom number of 1 to 8 in which optional hydrogens may be substituted with fluorine and in which optional —CH$_2$— may be substituted with —O—, —CH═CH—, cycloalkylene or cycloalkenylene, phenyl in which optional hydrogens may be substituted with halogen, methyl or methoxy, non-substituted naphthyl and phenylalkyl constituted from phenyl in which optional hydrogens may be substituted with fluorine, alkyl having a carbon atom number of 1 to 4, vinyl or methoxy and alkylene which has a carbon atom number of 1 to 8 and in which optional —CH$_2$— may be substituted with —O—; Z$^1$ is alkylene having a carbon atom number of 1 to 20 or alkenylene having a carbon atom number of 3 to 8, and in these alkylene and alkenylene, optional —CH$_2$— may be substituted with —O—;

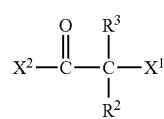
(5)

wherein both of X$^1$ and X$^2$ are halogens and may be the same or different; R$^2$ is alkyl having a carbon atom number of 1 to 20, aryl having a carbon atom number of 6 to 20 or aralkyl having a carbon atom number of 7 to 20; and R$^3$ is hydrogen, alkyl having a carbon atom number of 1 to 20, aryl having a carbon atom number of 6 to 20 or aralkyl having a carbon atom number of 7 to 20;

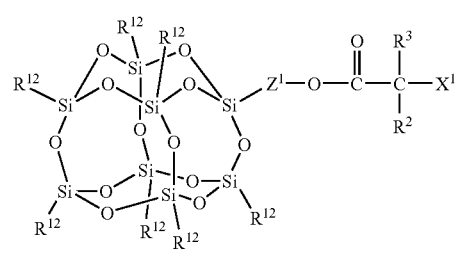
(6)

wherein R$^{12}$ and Z$^1$ each have the same meanings as those of these codes in Formula (4), and R$^2$, R$^3$ and X$^1$ each have the same meanings as those of these codes in Formula (5).

[26] A polymer obtained by polymerizing an addition-polymerizable monomer using the silicon compound as described in the item [1] as an initiator and using a transition metal complex as a catalyst.

[27] A polymer obtained by polymerizing an addition-polymerizable monomer using the silicon compound as described in the item [11] as an initiator and using a transition metal complex as a catalyst.

[28] A polymer represented by Formula (7):

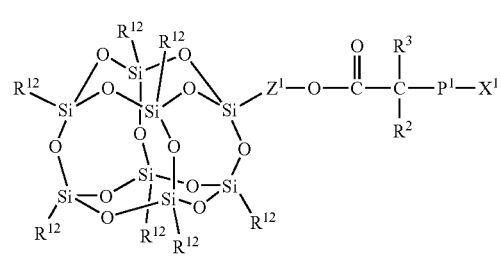
(7)

wherein all R$^{12}$'s are the same group selected from alkyl having a carbon atom number of 1 to 8 in which optional hydrogens may be substituted with fluorine and in which optional —CH$_2$— may be substituted with —O—, —CH=CH—, cycloalkylene or cycloalkenylene, phenyl in which optional hydrogens may be substituted with halogen, methyl or methoxy, non-substituted naphthyl and phenylalkyl constituted from phenyl in which optional hydrogens may be substituted with fluorine, alkyl having a carbon atom number of 1 to 4, vinyl or methoxy and alkylene which has a carbon atom number of 1 to 8 and in which optional —CH$_2$— may be substituted with —O—; Z$^1$ is alkylene having a carbon atom number of 1 to 20 or alkenylene having a carbon atom number of 3 to 8, and in these alkylene and alkenylene, optional —CH$_2$— may be substituted with —O—; R$^2$ is alkyl having a carbon atom number of 1 to 20, aryl having a carbon atom number of 6 to 20 or aralkyl having a carbon atom number of 7 to 20; R$^3$ is hydrogen, alkyl having a carbon atom number of 1 to 20, aryl having a carbon atom number of 6 to 20 or aralkyl having a carbon atom number of 7 to 20; X$^1$ is halogen; and P$^1$ is a chain of a structural unit obtained by polymerizing an addition-polymerizable monomer.

[29] The polymer as described in the item [27], wherein the addition-polymerizable monomer is at least one selected from (meth)acrylic acid derivatives and styrene derivatives.

[30] The polymer as described in the item [28], wherein all R$^{12}$'s are the same group selected from phenyl in which optional hydrogens may be substituted with halogen, methyl or methoxy, non-substituted naphthyl and phenylalkyl constituted from phenyl in which optional hydrogens may be substituted with fluorine, alkyl having a carbon atom number of 1 to 4, vinyl or methoxy and alkylene which has a carbon atom number of 1 to 8 and in which optional —CH$_2$— may be substituted with —O—; Z$^1$ is —C$_3$H$_6$— or —C$_2$H$_4$—; R$^2$ is methyl or ethyl; R$^3$ is hydrogen, methyl or ethyl; X$^1$ is bromine; and P$^1$ is a chain of a structural unit obtained by polymerizing at least one compound selected from (meth)acrylic acid derivatives and styrene derivatives.

[31] The polymer as described in the item [28], wherein all R$^{12}$'s are the same group selected from ethyl, 2-methylpropyl, 2,4,4-trimethylpentyl, cyclopentyl, cyclohexyl, non-substituted phenyl, 3,3,3-trifluoropropyl and tridecafluoro-1,1,2,2-tetrahydrooctyl; Z$^1$ is —C$_3$H$_6$— or —C$_2$H$_4$—; both of R$^2$ and R$^3$ are methyl; X$^1$ is bromine; and P$^1$ is a chain of a structural unit obtained by polymerizing at least one compound selected from (meth)acrylic acid derivatives and styrene derivatives.

[32] The polymer as described in the item [31], wherein P$^1$ is a chain of a structural unit obtained by polymerizing at least one compound selected from the styrene derivatives.

First, terms used in the present invention shall be explained. All of alkyl, alkylene, alkenyl and alkenylene may be either linear groups or branched groups. Both of cycloalkyl and cycloalkenyl may be or may not be groups having a cross-linked ring structure.

"Optional" used in the present invention shows that not only the position but also the number can optionally be selected. For example, alkyl in which optional —CH$_2$— may be substituted with —O— or —CH=CH— is any of alkyl, alkoxyalkyl, alkenyl, alkyloxyalkyl, alkenyloxyalkyl and alkenyloxyalkenyl. In the present invention, however, a case where —CH$_2$— bonded to an ester group is substituted with —O— and a case where plural continuous —CH$_2$— are substituted with —O— are not included.

(Meth)acrylic acid is a general term for acrylic acid and methacrylic acid. (Meth)acrylate is a general term for acrylate and methacrylate. (Meth)acryloyloxy is a general term for acryloyloxy and methacryloyloxy.

The compound represented by Formula (1) shall be described as the compound (1). The compounds represented by the other formulas shall be described by the same abbreviation.

The silicon compound of the present invention is represented by Formula (1):

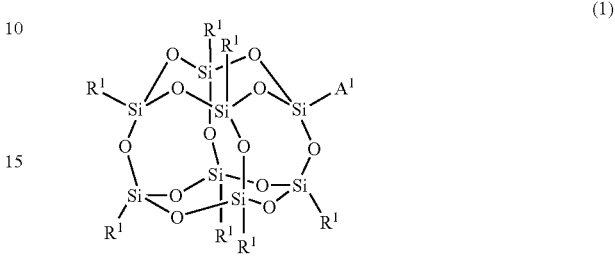

(1)

In Formula (1), R$^1$ is a group independently selected respectively from hydrogen, alkyl, substituted or non-substituted aryl and substituted or non-substituted arylalkyl. All R$^1$'s are preferably the same one group but may be constituted from different two or more groups. The examples of a case where seven R$^1$'s are constituted from different groups are a case where they are constituted from two or more alkyls, a case where they are constituted from two or more aryls, a case where they are constituted from two or more aralkyls, a case where they are constituted from hydrogen and at least one aryl, a case where they are constituted from at least one alkyl and at least one aryl, a case where they are constituted from at least one alkyl and at least one aralkyl and a case where they are constituted from at least one aryl and at least one aralkyl. They may be combinations other than the above cases. The compound (1) having at least two different R$^1$'s can be obtained by using two or more raw materials when producing it. These raw materials shall be described later.

When R$^1$ is alkyl, it has a carbon atom number of 1 to 40. The preferred carbon atom number is 1 to 30. The more preferred carbon atom number is 1 to 8. Optional hydrogens thereof may be substituted with fluorine, and optional —CH$_2$— may be substituted with —O—, —CH=CH—, cycloalkylene or cycloalkenylene. The preferred examples of such alkyl are non-substituted alkyl having a carbon atom number of 1 to 30, alkoxyalkyl having a carbon atom number of 2 to 30, a group in which one —CH$_2$— is substituted with cycloalkylene in alkyl having a carbon atom number of 1 to 8, alkenyl having a carbon atom number of 2 to 20, alkenyloxyalkenyl having a carbon atom number of 2 to 20, alkyloxyalkenyl having a carbon atom number of 2 to 20, a group in which one —CH$_2$— is substituted with cycloalkenylene in alkyl having a carbon atom number of 1 to 8 and groups in which optional hydrogens are substituted with fluorine in these groups given above. The preferred carbon atom numbers of cycloalkylene and cycloalkenylene are 3 to 8.

The examples of the non-substituted alkyl having a carbon atom number of 1 to 30 are methyl, ethyl, propyl, 1-methylethyl, butyl, 2-methylpropyl, 1,1-dimethylethyl, pentyl, hexyl, 1,1,2-trimethylpropyl, heptyl, octyl, 2,4,4-trimethylpentyl, nonyl, decyl, undecyl, dodecyl, tetradecyl, hexadecyl, octadecyl, eicosyl, docosyl and triacontyl.

The examples of the fluorinated alkyl having a carbon atom number of 1 to 30 are 3,3,3-trifluoropropyl, 3,3,4,4,5,5,6,6,6-nonadecafluorohexyl, tridecafluoro-1,1,2,2-tetrahydrooctyl, heptadecafluoro-1,1,2,2-tetrahydrodecyl, perfluoro-1H,1H,2H,2H-dodecyl and perfluoro-1H,1H,2H,2H-tetradecyl.

The examples of the alkoxyalkyl having a carbon atom number of 2 to 29 are 3-methoxypropyl, methoxyethoxyundecyl and 3-heptafluoroisopropoxypropyl.

The examples of the group in which one —CH$_2$— is substituted with cycloalkylene in alkyl having a carbon atom number of 1 to 8 are cyclohexylmethyl, adamantaneethyl, cyclopentyl, cyclohexyl, 2-bicycloheptyl and cyclooctyl. Cyclohexyl is an example in which —CH$_2$— in methyl is substituted with cyclohexylene. Cyclohexylmethyl is an example in which —CH$_2$— in a β position of ethyl is substituted with cyclohexylene.

The examples of the alkenyl having a carbon atom number of 2 to 20 are vinyl, 2-propenyl, 3-butenyl, 5-hexenyl, 7-octenyl, 10-undecenyl and 21-docosenyl.

The example of the alkenyloxyalkyl having a carbon atom number of 2 to 20 is allyloxyundecyl.

The examples of the group in which one —CH$_2$— is substituted with cycloalkenylene in alkyl having a carbon atom number of 1 to 8 are 2-(3-cyclohexenyl)ethyl, 5-(bicycloheptenyl)ethyl, 2-cyclopentenyl, 3-cyclohexenyl, 5-norbornene-2-yl and 4-cyclooctenyl.

The examples of a case where R$^1$ in Formula (1) is substituted or non-substituted aryl are phenyl in which optional hydrogens may be substituted with halogen or alkyl having a carbon atom number of 1 to 10 and non-substituted naphthyl. The preferred examples of halogen are a fluorine atom, a chlorine atom and bromine. In the alkyl having a carbon atom number of 1 to 10, optional hydrogens may be substituted with fluorine, and optional —CH$_2$— may be substituted with —O—, —CH=CH— or phenylene. That is, the preferred examples of the case where R$^1$ is substituted or non-substituted aryl are non-substituted phenyl, non-substituted naphthyl, alkylphenyl, alkyloxyphenyl, alkenylphenyl, phenyl having as a substituent, a group in which optional —CH$_2$— in the alkyl having a carbon atom number of 1 to 10 is substituted with phenylene and groups in which optional hydrogens are substituted with halogen in these groups.

The examples of the halogenated phenyl are pentafluorophenyl, 4-chlorophenyl and 4-bromophenyl.

The examples of the alkylphenyl are 4-methylphenyl, 4-ethylphenyl, 4-propylphenyl, 4-butylphenyl, 4-pentylphenyl, 4-heptylphenyl, 4-octylphenyl, 4-nonylphenyl, 4-decylphenyl, 2,4-dimethylphenyl, 2,4,6-trimethylphenyl, 2,4,6-triethylphenyl, 4-(1-methylethyl)phenyl, 4-(1,1-dimethylethyl)phenyl, 4-(2-ethylhexyl)phenyl and 2,4,6-tris(1-methylethyl)phenyl.

The examples of the alkyloxyphenyl are (4-methoxy)phenyl, (4-ethoxy)phenyl, (4-propoxy)phenyl, (4-butoxy)phenyl, (4-pentyloxy)phenyl, (4-heptyloxy)phenyl, (4-decyloxy)phenyl, (4-octadecyloxy)phenyl, 4-(1-methylethoxy)phenyl, 4-(2-methylpropoxy)phenyl and 4-(1,1-dimethylethoxy)phenyl. The examples of the alkenylphenyl are 4-vinylphenyl, 4-(1-methylvinyl)phenyl and 4-(3-butenyl)phenyl.

The examples of the phenyl having as a substituent, a group in which optional —CH$_2$— in the alkyl having a carbon atom number of 1 to 10 is substituted with phenylene are 4-(2-phenylvinyl)phenyl, 4-phenoxyphenyl, 3-(phenylmethyl)phenyl, biphenyl and terphenyl. 4-(2-Phenylvinyl)phenyl is an example in which one —CH$_2$— in ethyl of ethylphenyl is substituted with phenylene and in which the other —CH$_2$— is substituted with —CH=CH—.

The examples of the phenyl in which a part of hydrogens on a benzene ring is substituted with halogen and in which the other hydrogens are substituted with alkyl, alkyloxy or alkenyl are 3-chloro-4-methylphenyl, 2,5-dichloro-4-methylphenyl, 3,5-dichloro-4-methylphenyl, 2,3,5-trichloro-4-methylphenyl, 2,3,6-trichloro-4-methylphenyl, 3-bromo-4-methylphenyl, 2,5-dibromo-4-methylphenyl, 3,5-dibromo-4-methylphenyl, 2,3-difluoro-4-methylphenyl, 3-chloro-4-methoxyphenyl, 3-bromo-4-methoxyphenyl, 3,5-dibromo-4-methoxyphenyl, 2,3-difluoro-4-methoxyphenyl, 2,3-difluoro-4-ethoxyphenyl, 2,3-difluoro-4-propoxyphenyl and 4-vinyl-2,3,5,6-tetrafluorophenyl.

Next, the examples of a case where R$^1$ in Formula (1) is substituted or non-substituted arylalkyl shall be given. In alkylene of the arylalkyl constituting the arylalkyl, optional hydrogens may be substituted with fluorine, and optional —CH$_2$— may be substituted with —O— or —CH=CH—. The preferred example of the arylalkyl is phenylalkyl. In this case, the preferred carbon atom number of the alkylene is 1 to 12, and the more preferred carbon atom number is 1 to 8. The examples of the non-substituted phenylalkyl are phenylmethyl, 2-phenylethyl, 3-phenylpropyl, 4-phenylbutyl, 5-phenylpentyl, 6-phenylhexyl, 11-phenylundecyl, 1-phenylethyl, 2-phenylpropyl, 1-methyl-2-phenylethyl, 1-phenylpropyl, 3-phenylbutyl, 1-methyl-3-phenylpropyl, 2-phenylbutyl, 2-methyl-2-phenylpropyl and 1-phenylhexyl.

In the phenylalkyl, optional hydrogens on a benzene ring may be substituted with halogen or alkyl having a carbon atom number of 1 to 12. In this alkyl having a carbon atom number of 1 to 12, optional hydrogens may be substituted with fluorine, and optional —CH$_2$— may be substituted with —O—, —CH=CH—, cycloalkylene or phenylene. The examples of the phenylalkyl in which optional hydrogens on phenyl are substituted with fluorine are 4-fluorophenylmethyl, 2,3,4,5,6-pentafluorophenylmethyl, 2-(2,3,4,5,6-pentafluorophenyl)ethyl, 3-(2,3,4,5,6-pentafluorophenyl)propyl, 2-(2-fluorophenyl)propyl and 2-(4-fluorophenyl)propyl.

The examples of the phenylalkyl in which hydrogens on a benzene ring are substituted with chlorine are 4-chlorophenylmethyl, 2-chlorophenylmethyl, 2,6-dichlorophenylmethyl, 2,4-dichlorophenylmethyl, 2,3,6-trichlorophenylmethyl, 2,4,6-trichlorophenylmethyl, 2,4,5-trichlorophenylmethyl, 2,3,4,6-tetrachloro-phenylmethyl, 2,3,4,5,6-pentachlorophenylmethyl, 2-(2-chlorophenyl)ethyl, 2-(4-chlorophenyl)ethyl, 2-(2,4,5-chlorophenyl)ethyl, 2-(2,3,6-chlorophenyl)ethyl, 3-(3-chlorophenyl)propyl, 3-(4-chlorophenyl)propyl, 3-(2,4,5-trichlorophenyl)propyl, 3-(2,3,6-trichlorophenyl)propyl, 4-(2-chlorophenyl)butyl, 4-(3-chlorophenyl)butyl, 4-(4-chlorophenyl)butyl, 4-(2,3,6-trichlorophenyl)butyl, 4-(2,4,5-trichlorophenyl)butyl, 1-(3-chlorophenyl)-ethyl, 1-(4-chlorophenyl)ethyl, 2-(4-chlorophenyl)-propyl, 2-(2-chlorophenyl)propyl and 1-(4-chlorophenyl)butyl.

The examples of the phenylalkyl in which hydrogens on phenyl are substituted with bromine are 2-bromophenylmethyl, 4-bromophenylmethyl, 2,4-dibromophenylmethyl, 2,4,6-tribromophenylmethyl, 2,3,4,5-tetrabromophenylmethyl, 2,3,4,5,6-pentabromophenylmethyl, 2-(4-bromophenyl)ethyl, 3-(4-bromophenyl)propyl, 3-(3-bromophenyl)propyl, 4-(4-bromophenyl)butyl, 1-(4-bromophenyl)ethyl, 2-(2-bromophenyl)propyl and 2-(4-bromophenyl)propyl.

The examples of the phenylalkyl in which hydrogens on a benzene ring are substituted with alkyl having a carbon atom number of 1 to 12 are 2-methylphenylmethyl, 3-methylphenylmethyl, 4-methylphenylmethyl, 4-dodecylphenylmethyl, 3,5-dimethylphenylmethyl, 2-(4-methylphenyl)ethyl, 2-(3-methylphenyl)ethyl, 2-(2,5-dimethylphenyl)ethyl, 2-(4-ethylphenyl)ethyl, 2-(3-ethylphenyl)ethyl, 1-(4-methylphenyl)ethyl, 1-(3-methylphenyl)ethyl, 1-(2-methylphenyl)ethyl, 2-(4-methylphenyl)propyl, 2-(2-methylphenyl)propyl, 2-(4-ethylphenyl)propyl, 2-(2-ethylphenyl)propyl, 2-(2,3-dimethylphenyl)propyl, 2-(2,5-dimethylphenyl)propyl, 2-(3,5-dimethylphenyl)-propyl, 2-(2,4-dimethylphenyl)propyl, 2-(3,4-dimethylphenyl)propyl, 2-(2,5-dimethylphenyl)butyl, (4-(1-methylethyl)phenyl)methyl, 2-(4-(1,1-dimethylethyl)phenyl)ethyl, 2-(4-(1-methylethyl)phenyl)propyl and 2-(3-(1-methylethyl)phenyl)propyl.

The examples of the phenylalkyl in which hydrogens on a benzene ring are substituted with alkyl having a carbon atom number of 1 to 12 and in which hydrogens in this alkyl are substituted with fluorines are 3-(trifluoromethyl)phenylethyl, 2-(4-trifluoromethylphenyl)ethyl, 2-(4-nonafluorobutylphenyl)ethyl, 2-(4-tridecafluorohexylphenyl)ethyl, 2-(4-heptadecafluorooctylphenyl)ethyl, 1-(3-trifluoromethylphenyl)ethyl, 1-(4-trifluoromethylphenyl)ethyl, 1-(4-nonafluorobutylphenyl)ethyl, 1-(4-tridecafluorohexylphenyl)ethyl, 1-(4-heptadecafluorooctylphenyl)ethyl, 2-(4-nonafluorobutylphenyl)propyl, 1-methyl-1-(4-nonafluorobutylphenyl)ethyl, 2-(4-tridecafluorohexylphenyl)propyl, 1-methyl-1-(4-tridecafluorohexyl-phenyl)ethyl, 2-(4-heptadecafluorooctylphenyl)propyl and 1-methyl-1-(4-heptadecafluorooctylphenyl)ethyl.

The examples of the phenylalkyl in which hydrogens on a benzene ring are substituted with alkyl having a carbon atom number of 1 to 12 and in which —CH$_2$— in this alkyl is substituted with —CH=CH— are 2-(4-vinylphenyl)ethyl, 1-(4-vinylphenyl)ethyl and 1-(2-(2-propenyl)phenyl)ethyl.

The examples of the phenylalkyl in which hydrogens on a benzene ring are substituted with alkyl having a carbon atom number of 1 to 12 and in which —CH$_2$— in this alkyl is substituted with —O— are 4-methoxyphenylmethyl, 3-methoxyphenylmethyl, 4-ethoxyphenylmethyl, 2-(4-methoxyphenyl)ethyl, 3-(4-methoxyphenyl)propyl, 3-(2-methoxyphenyl)propyl, 3-(3,4-dimethoxyphenyl)propyl, 11-(4-methoxyphenyl)undecyl, 1-(4-methoxyphenyl)ethyl, 2-(3-(methoxymethyl)phenyl)ethyl and 3-(2-nonadecafluorodecenyloxyphenyl)propyl.

The examples of the phenylalkyl in which hydrogens on a benzene ring are substituted with alkyl having a carbon atom number of 1 to 12 and in which one of —CH$_2$— in this alkyl is substituted with cycloalkylene are, to give examples thereof including a case where another —CH$_2$— is substituted with —O—, cyclopentylphenylmethyl, cyclopentyloxyphenylmethyl, cyclohexylphenylmethyl, cyclohexylphenylethyl, cyclohexylphenylpropyl and cyclohexyloxyphenylmethyl.

The examples of the phenylalkyl in which hydrogens on a benzene ring are substituted with alkyl having a carbon atom number of 1 to 12 and in which one of —CH$_2$— in this alkyl is substituted with phenylene are, to give examples thereof including a case where another —CH$_2$— is substituted with —O—, 2-(4-phenoxyphenyl)ethyl, 2-(4-phenoxyphenyl)propyl, 2-(2-phenoxyphenyl)propyl, 4-biphenylylmethyl, 3-biphenylylethyl, 4-biphenylylethyl, 4-biphenylylpropyl, 2-(2-biphenylyl)propyl and 2-(4-biphenylyl)propyl.

The examples of the phenylalkyl in which at least two hydrogens on a benzene ring are substituted with different groups are 3-(2,5-dimethoxy-(3,4,6-trimethylphenyl)propyl, 3-chloro-2-methylphenylmethyl, 4-chloro-2-methylphenylmethyl, 5-chloro-2-methylphenylmethyl, 6-chloro-2-methylphenylmethyl, 2-chloro-4-methylphenylmethyl, 3-chloro-4-methylphenylmethyl, 2,3-dichloro-4-methylphenylmethyl, 2,5-dichloro-4-methylphenylmethyl, 3,5-dichloro-4-methylphenylmethyl, 2,3,5-trichloro-4-methylphenylmethyl, 2,3,5,6-tetrachloro-4-methylphenylmethyl, (2,3,4,6-tetrachloro-5-methylphenyl)methyl, 2,3,4,5-tetrachloro-6-methylphenylmethyl, 4-chloro-3,5-dimethylphenylmethyl, 2-chloro-3,5-dimethylphenylmethyl, 2,4-dichloro-3,5-dimethylphenylmethyl, 2,6-dichloro-3,5-dimethylphenylmethyl, 2,4,6-trichloro-3,5-dimethylphenylmethyl, 3-bromo-2-methylphenylmethyl, 4-bromo-2-methylphenylmethyl, 5-bromo-2-methylphenylmethyl, 6-bromo-2-methylphenylmethyl, 3-bromo-4-methylphenylmethyl, 2,3-dibromo-4-methylphenylmethyl, 2,3,5-tribromo-4-methylphenylmethyl, 2,3,5,6-tetrabromo-4-methylphenylmethyl and 11-(3-chloro-4-methoxyphenyl)undecyl.

The most preferred examples of phenyl constituting the phenylalkyl are non-substituted phenyl and phenyl having at least one of fluorine, alkyl having a carbon atom number of 1 to 4, vinyl and methoxy as a substituent.

The examples of the phenylalkyl in which —CH$_2$— in alkylene is substituted with —O— or —CH=CH— are 3-phenoxypropyl, 1-phenylvinyl, 2-phenylvinyl, 3-phenyl-2-propenyl, 4-phenyl-4-pentenyl and 13-phenyl-12-tridecenyl.

The examples of the phenylalkenyl in which hydrogen on a benzene ring is substituted with fluorine or methyl are 4-fluorophenylvinyl, 2,3-difluorophenylvinyl, 2,3,4,5,6-pentafluorophenylvinyl and 4-methylphenylvinyl.

The most preferred examples of R$^1$ are alkyl having a carbon atom number of 2 to 8 (ethyl, isobutyl, isooctyl and the like), phenyl, halogenated phenyl, phenyl having at least one methyl, methoxyphenyl, naphthyl, phenylmethyl, phenylethyl, phenylbutyl, 2-phenylpropyl, 1-methyl-2-phenylethyl, pentafluorophenylpropyl, 4-ethylphenylethyl, 3-ethylphenylethyl, 4-(1,1-dimethylethyl)phenylethyl, 4-vinylphenylethyl, 1-(4-vinylphenyl)ethyl, 4-methoxyphenylpropyl and phenoxypropyl.

A$^1$ in Formula (1) is a group having an α-haloester group. The group having an α-haloester group means a group having α-halocarbonyloxy as an end group. An atom transfer radical polymerization method is known as a polymerization method using this α-halocarbonyloxy group as an initiating group for radical polymerization. A polymerization catalyst used in this method is a metal complex comprising the eighth, ninth, tenth or eleventh element in the periodic table as a central metal atom. It is known that the group having α-halocarbonyloxy has an excellent polymerization initiating ability in this atom transfer radical polymerization. It is well known as well that this polymerization is living fation. That is, the compound (1) has an excellent polymerization initiating ability under the presence of a transition metal complex and can continue to maintain a living polymerization. The compound (1) can initiate polymerization of all radically polymerizable monomers, and it can allow particularly styrene base derivatives to exhibit an excellent living polymerization.

The silicon compound of the present invention has α-halocarbonyloxy as an end group and therefore can be derived into a lot of derivatives by applying various organic reactions. For example, the compound (1) can be derived into silsesquioxanes having an organic metal functional group by reacting it with lithium, magnesium or zinc. To be specific, the compound (1) is reacted with zinc and derived into silsesquioxane having an organic zinc functional group, and then aldehyde and ketone are added thereto, whereby it can be converted into alcohols. That is, silsesquioxane having an organic zinc functional group is useful as an intermediate raw material used for a so-called Reformatsky reaction.

An α-halocarbonyloxy group in the compound (1) has a strong electrophilicity, and therefore it can be converted into an amino group and a mercapto group using various nucleophilic reagents. Further, the compound (1) is treated with enamine to be converted into an imine salt, and this imine salt is hydrolyzed, whereby it can be converted into ketone. That is, the compound (1) is also useful as an intermediate raw material used for a stork-enamine reaction. Silsesquioxane derivatives having various organic functional groups and polymerizable functional groups can be prepared as well by reacting the compound (1) with aliphatic or aromatic Grignard reagents. Accordingly, the silicon compound of the present invention can be used not only as a polymerization initiator but also as an intermediate useful for various organic syntheses.

The preferred example of $A^1$ is a group represented by Formula (2):

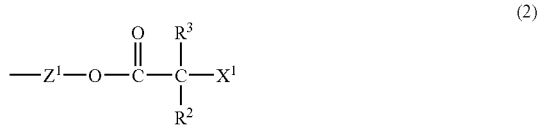

in Formula (2), $X^1$ is halogen; $R^2$ is alkyl having a carbon atom number of 1 to 20, aryl having a carbon atom number of 6 to 20 or aralkyl having a carbon atom number of 7 to 20; $R^3$ is hydrogen, alkyl having a carbon atom number of 1 to 20, aryl having a carbon atom number of 6 to 20 or aralkyl having a carbon atom number of 7 to 20; $Z^1$ is alkylene having a carbon atom number of 1 to 20 or alkenylene having a carbon atom number of 3 to 8; and in these alkylene and alkenylene, optional —$CH_2$— may be substituted with —O—. The preferred example of $Z^1$ is —$C_2H_4$—O—$C_3H_6$—, —$C_3H_6$— or —$C_2H_4$—. The examples of halogen are chlorine, bromine and iodine. Chlorine and bromine are most preferred as an initiating group for atom transfer radical polymerization.

Next, a production process for the silicon compound of the present invention shall be explained. The preferred raw material is a silicon compound represented by Formula (3):

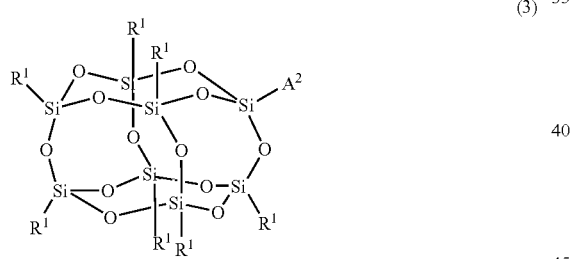

In Formula (3), $R^1$ has the same meaning as that of $R^1$ in Formula (1), and $A^2$ is an organic group having a hydroxyl group at an end.

This compound (3) used as a raw material is reacted with acid halide in which halogen is bonded to carbon in an α-position, whereby it can be derived into the compound (1). Then, the more preferred raw material in the present invention is a silicon compound represented by Formula (4):

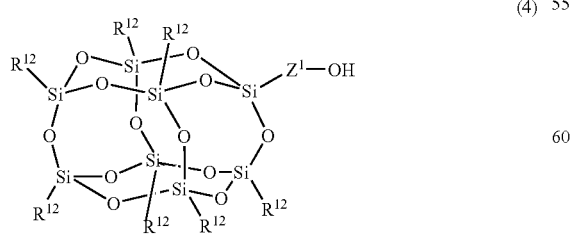

All $R^{12}$'s in Formula (4) are the same group selected from alkyl having a carbon atom number of 1 to 8 in which optional hydrogens may be substituted with fluorine and in which optional —$CH_2$— may be substituted with —O—, —CH=CH—, cycloalkylene or cycloalkenylene, phenyl in which optional hydrogens may be substituted with halogen, methyl or methoxy, non-substituted naphthyl and phenylalkyl constituted from phenyl in which optional hydrogens may be substituted with fluorine, alkyl having a carbon atom number of 1 to 4, vinyl or methoxy and alkylene which has a carbon atom number of 1 to 8 and in which optional —$CH_2$— may be substituted with —O—. $Z^1$ in Formula (4) is alkylene having a carbon atom number of 1 to 20 or alkenylene having a carbon atom number of 3 to 8. In these alkylene and alkenylene, optional —$CH_2$— may be substituted with —O—.

A synthetic route shown in the following scheme 1 and scheme 2 is one of the specific examples of a process for producing the compound (4). That is, a compound (A-1) is reacted with acetoxyethyltrichlorosilane at a room temperature under the presence of triethylamine using tetrahydrofuran as a solvent to prepare a compound B. Then, the compound B is subjected to transesterification reaction in methanol under the presence of a sulfuric acid catalyst, whereby a compound C having hydroxyalkyl can be prepared. The compound (A-1) in the scheme 1 is obtained by obtaining polysilsesquioxane by hydrolyzing a silicon compound having three hydrolyzable groups and then reacting it with monovalent alkali metal hydroxide in tetrahydrofuran. The compound (A-1) is obtained as well by hydrolyzing a silicon compound having three hydrolyzable groups under the presence of alkali metal hydroxide in an oxygen-containing organic solvent and subjecting it to polycondensation. A compound (A-2) may be used in place of the compound (A-1). The compound (A-2) is described in Organometallics, 10, 2526-(1991). In the following scheme, Ph is phenyl; THF is tetrahydrofuran; and TEA is triethylamine.

Scheme 1

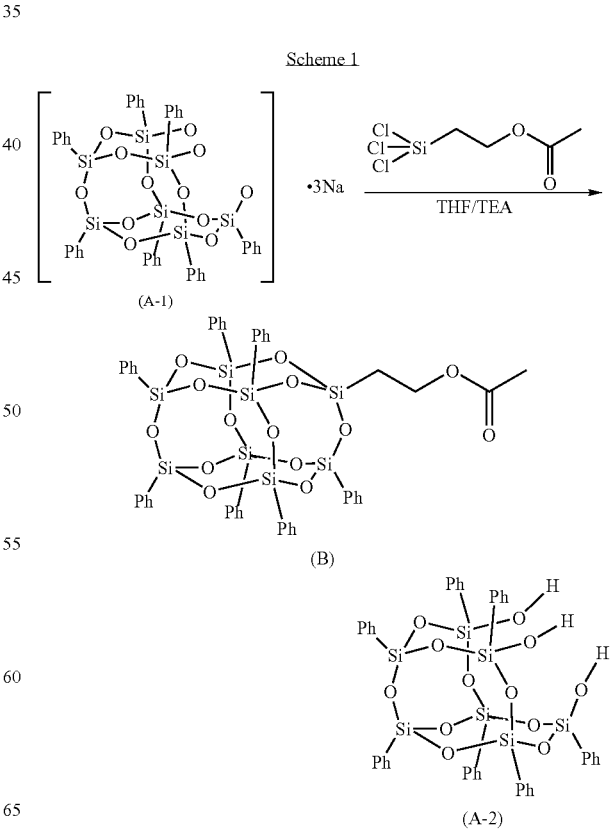

Scheme 2

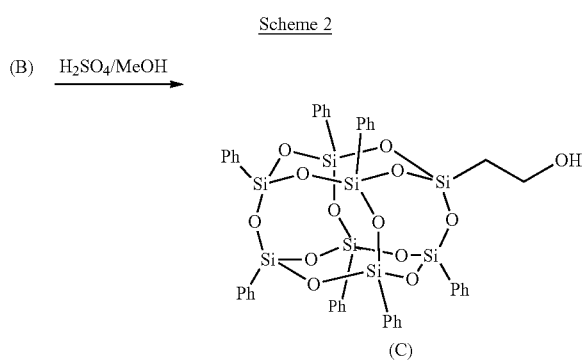

The compound (4) can be produced by a process of Feher et al. The process of Feher et al is described in Chemical Communications (Cambridge, United Kingdom), 1289 to 1290 (1990). The compound (4) can be produced by making use of the process of Feher et al for a part of the synthetic route. One of the specific examples thereof shall be shown in a scheme 3 to a scheme 5.

Scheme 3

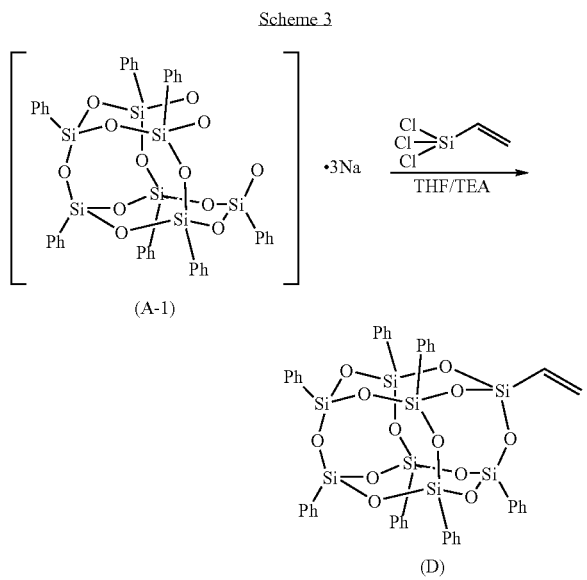

Scheme 4

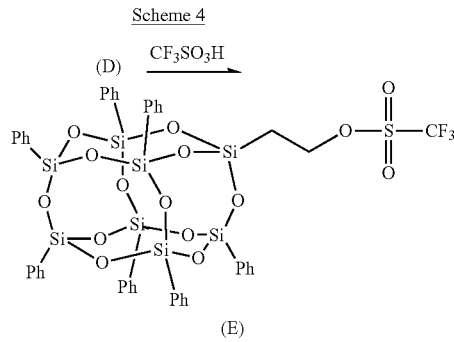

Scheme 5

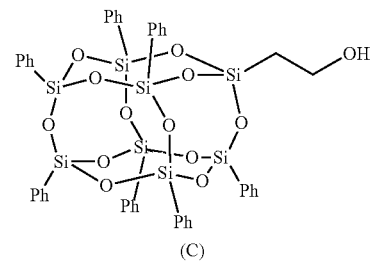

That is, the compound (A-1) is reacted with vinyltrichlorosilane at a room temperature under the presence of triethylamine using tetrahydrofuran as a solvent to prepare a compound (D). Then, one equivalent of trifluoromethanesulfonic acid is added to a vinyl group of the compound (D) to prepare a compound (E). The compound (E) thus obtained is hydrolyzed, whereby a compound (C) can be obtained. Also, in the case of this route, the compound (A-2) can be used in place of the compound (A-1).

A compound (6) which is a preferred example of the compound of the present invention can be obtained by reacting the compound (4) thus obtained with a compound (5):

In Formula (5), $X^2$ is halogen, and the examples thereof are chlorine, bromine and iodine. $X^1$, $R^2$ and $R^3$ each have the same meanings as those of these codes in Formula (2). $X^1$ and $X^2$ may be the same or different.

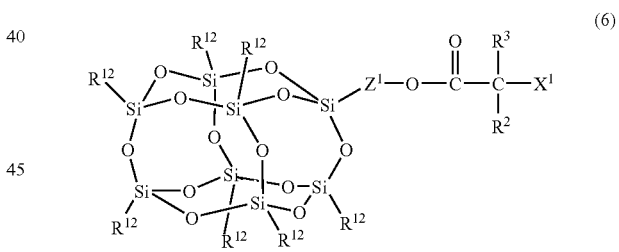

$R^{12}$ and $Z^1$ in Formula (6) each have the same meanings as those of these codes in Formula (4), and $R^2$, $R^3$ and $X^1$ each have the same meanings as those of these codes in Formula (2).

The compound (4) is readily reacted with the compound (5) to become an ester. Hydrogen halides by-produced in the reaction induces side reactions such as dehydration, addition to a double bond site and the like, and therefore the reaction is carried out in the coexistence of organic bases in order to remove the hydrogen halides. The examples of the organic bases are pyridine, dimethylaniline, triethylamine and tetramethylurea. The other organic bases may be used as long as they can inhibit the side reactions and allow the reaction to quickly proceed. The most preferred example of the organic bases is triethylamine. This reaction is a nucleophilic displacement reaction which quantitatively proceeds, and a use amount of the compound (5) is preferably 1 to 10 times in terms of an equivalent ratio based on the compound (4). An increase in a use amount of the compound (5) makes it possible to react the whole compound (4) and makes it possible to shorten the reaction time.

This reaction is usually carried out in an atmosphere of inert gas such as argon gas and nitrogen gas using a dry organic solvent which is inactive to the raw material. The examples of the organic solvent are cyclic ethers such as tetrahydrofuran and dioxane, aromatic hydrocarbons such as toluene and xylene, halogenated hydrocarbons such as methylene chloride and chloroform and carbon tetrachloride. The preferred example of the organic solvent is methylene chloride. The reaction temperature shall not specifically be restricted. However, the above reaction quickly goes on while generating heat, and therefore usually it is carried out preferably under a low temperature condition. The preferred reaction temperature is 100° C. or lower, and the most referred reaction temperature is 35° C. or lower. As a matter of fact, the reaction may be carried out while irregularly controlling the reaction temperature. For example, employed is a method in which the reaction is carried out while cooling the reaction system using a dry ice-methanol bath or an ice bath in an initial stage and in which the temperature is then elevated to the vicinity of a room temperature to continue the reaction. The reaction time shall not specifically be restricted, and usually the intended silicon compound can be obtained in 1 to 10 hours.

In the following explanations, the unreacted raw material compounds and the solvents shall be referred to as "impurities". If a distillation method is applied in order to remove the impurities, the liquid is maintained under a high temperature condition for long time, and therefore the intended compound is likely to be decomposed. Accordingly, it is preferably refined by reprecipitation operation in order to efficiently remove the impurities without damaging a purity of the compound (6). This refining method is carried out in the following manner. First, the reaction liquid is dissolved in a solvent dissolving both of the compound (6) and the impurities. In this case, a preferred concentration of the compound (6) is, roughly speaking, 1 to 15% by weight. Next, such a solvent as not dissolving the compound (6) but dissolving the impurities, a so-called precipitant is added to the above solution to precipitate only the compound (6). A preferred use amount of the precipitant is 20 to 50 times based on the weight of the solvent used for dissolving both of the compound (6) and the impurities. This use range is a rough standard, and as is the case with the foregoing concentration rage of the compound (6), it may not necessarily fall in the above range.

The preferred solvent for dissolving the compound (6) is a solvent having a large dissolving power and a relatively low boiling point. The preferred precipitant is a solvent which is compatible with the solvent for dissolving the compound (6) and does not dissolve the compound (6) at all and which dissolves only the impurities and has a relatively low boiling point. The example of the preferred precipitant is lower alcohols. The particularly preferred precipitant is methanol or ethanol. A repeating frequency of the reprecipitation operation is advisably raised in order to further elevate the refining degree.

Next, the examples of the compound (1) shall specifically be shown by using codes defined in Table 1. Examples shown in Table 2 to Table 9 are the examples of a case in which $R^{12}$ is ethyl, 2-methylpropyl, 2,4,4-trimethylpentyl, cyclopentyl, cyclohexyl, 3,3,3-trifluoropropyl or phenyl in Formula (6) and in which $Z^1$ is —$(CH_2)_2$—, —$(CH_2)_3$—, —$(CH_2)_4$—, —$(CH_2)_5$— or —$C_2H_4$—O—$C_3H_6$—. The compound (1) shall not be restricted by these examples.

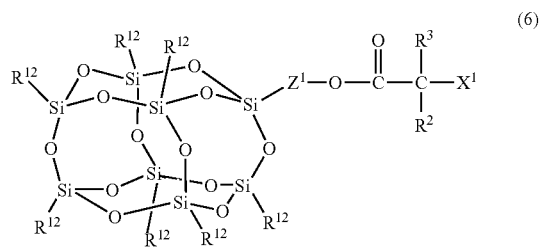

(6)

T8 in the following tables means an octavalent group having a PSQ skeleton shown below:

TABLE 1

| Code | Chemical formula |
|---|---|
| Me | —$CH_3$ |
| Et | —$C_2H_5$ |
| IBu | —$CH_2CH(CH_3)_2$ |
| IOc | —$CH_2CH(CH_3)CH_2C(CH_3)_3$ |
| CPe | (cyclopentyl) |
| CHe | (cyclohexyl) |
| Ph | (phenyl) |
| TFPr | —$CH_2CH_2CF_3$ |
| C2 | —$C_2H_4$— |
| C3 | —$C_3H_6$— |
| C4 | —$C_4H_8$— |
| C5 | —$C_5H_{10}$— |
| C2OC3 | —$C_2H_4$—O—$C_3H_6$— |
| CL | —Cl |
| BR | —Br |

TABLE 2

| No. | $R^{12}$ | $Z^1$ | $R^2$ | $R^3$ | $X^1$ | Formula (6) |
|---|---|---|---|---|---|---|
| 1 | Et | C2 | Me | H | CL | (Et—)$_7$ T8 (—C2—OCO—CHMe—CL) |
| 2 | IBu | C2 | Me | H | CL | (IBu—)$_7$ T8 (—C2—OCO—CHMe—CL) |
| 3 | IOc | C2 | Me | H | CL | (IOc—)$_7$ T8 (—C2—OCO—CHMe—CL) |

TABLE 2-continued

| No. | R$^{12}$ | Z$^1$ | R$^2$ | R$^3$ | X$^1$ | Formula (6) |
|---|---|---|---|---|---|---|
| 4 | CPe | C2 | Me | H | CL | (CPe—)$_7$ T8 (—C2—OCO—CHMe—CL) |
| 5 | CHe | C2 | Me | H | CL | (CHe—)$_7$ T8 (—C2—OCO—CHMe—CL) |
| 6 | Ph | C2 | Me | H | CL | (Ph—)$_7$ T8 (—C2—OCO—CHMe—CL) |
| 7 | TFPr | C2 | Me | H | CL | (TFPr—)$_7$ T8 (—C2—OCO—CHMe—CL) |
| 8 | Et | C3 | Me | H | CL | (Et—)$_7$ T8 (—C3—OCO—CHMe—CL) |
| 9 | IBu | C3 | Me | H | CL | (IBu—)$_7$ T8 (—C3—OCO—CHMe—CL) |
| 10 | IOc | C3 | Me | H | CL | (IOc—)$_7$ T8 (—C3—OCO—CHMe—CL) |
| 11 | CPe | C3 | Me | H | CL | (CPe—)$_7$ T8 (—C3—OCO—CHMe—CL) |
| 12 | CHe | C3 | Me | H | CL | (CHe—)$_7$ T8 (—C3—OCO—CHMe—CL) |
| 13 | Ph | C3 | Me | H | CL | (Ph—)$_7$ T8 (—C3—OCO—CHMe—CL) |
| 14 | TFPr | C3 | Me | H | CL | (TFPr—)$_7$ T8 (—C3—OCO—CHMe—CL) |
| 15 | Et | C4 | Me | H | CL | (Et—)$_7$ T8 (—C4—OCO—CHMe—CL) |
| 16 | IBu | C4 | Me | H | CL | (IBu—)$_7$ T8 (—C4—OCO—CHMe—CL) |
| 17 | IOc | C4 | Me | H | CL | (IOc—)$_7$ T8 (—C4—OCO—CHMe—CL) |
| 18 | CPe | C4 | Me | H | CL | (CPe—)$_7$ T8 (—C4—OCO—CHMe—CL) |
| 19 | CHe | C4 | Me | H | CL | (CHe—)$_7$ T8 (—C4—OCO—CHMe—CL) |
| 20 | Ph | C4 | Me | H | CL | (Ph—)$_7$ T8 (—C4—OCO—CHMe—CL) |
| 21 | TFPr | C4 | Me | H | CL | (TFPr—)$_7$ T8 (—C4—OCO—CHMe—CL) |
| 22 | Et | C5 | Me | H | CL | (Et—)$_7$ T8 (—C5—OCO—CHMe—CL) |
| 23 | IBu | C5 | Me | H | CL | (IBu—)$_7$ T8 (—C5—OCO—CHMe—CL) |
| 24 | IOc | C5 | Me | H | CL | (IOc—)$_7$ T8 (—C5—OCO—CHMe—CL) |
| 25 | CPe | C5 | Me | H | CL | (CPe—)$_7$ T8 (—C5—OCO—CHMe—CL) |
| 26 | CHe | C5 | Me | H | CL | (CHe—)$_7$ T8 (—C5—OCO—CHMe—CL) |
| 27 | Ph | C5 | Me | H | CL | (Ph—)$_7$ T8 (—C5—OCO—CHMe—CL) |
| 28 | TFPr | C5 | Me | H | CL | (TFPr—)$_7$ T8 (—C5—OCO—CHMe—CL) |
| 29 | Et | C2OC3 | Me | H | CL | (Et—)$_7$ T8 (—C2OC3—OCO—CHMe—CL) |
| 30 | IBu | C2OC3 | Me | H | CL | (IBu—)$_7$ T8 (—C2OC3—OCO—CHMe—CL) |

TABLE 3

| No. | R$^{12}$ | Z$^1$ | R$^2$ | R$^3$ | X$^1$ | Formula (6) |
|---|---|---|---|---|---|---|
| 31 | IOc | C2OC3 | Me | H | CL | (IOc—)$_7$ T8 (—C2OC3—OCO—CHMe—CL) |
| 32 | CPe | C2OC3 | Me | H | CL | (CPe—)$_7$ T8 (—C2OC3—OCO—CHMe—CL) |
| 33 | CHe | C2OC3 | Me | H | CL | (CHe—)$_7$ T8 (—C2OC3—OCO—CHMe—CL) |
| 34 | Ph | C2OC3 | Me | H | CL | (Ph—)$_7$ T8 (—C2OC3—OCO—CHMe—CL) |
| 35 | TFPr | C2OC3 | Me | H | CL | (TFPr—)$_7$ T8 (—C2OC3—OCO—CHMe—CL) |
| 36 | Et | C2 | Me | Me | CL | (Et—)$_7$ T8 (—C2—OCO—CMe$_2$—CL) |
| 37 | IBu | C2 | Me | Me | CL | (IBu—)$_7$ T8 (—C2—OCO—CMe$_2$—CL) |
| 38 | IOc | C2 | Me | Me | CL | (IOc—)$_7$ T8 (—C2—OCO—CMe$_2$—CL) |
| 39 | CPe | C2 | Me | Me | CL | (CPe—)$_7$ T8 (—C2—OCO—CMe$_2$—CL) |
| 40 | CHe | C2 | Me | Me | CL | (CHe—)$_7$ T8 (—C2—OCO—CMe$_2$—CL) |
| 41 | Ph | C2 | Me | Me | CL | (Ph—)$_7$ T8 (—C2—OCO—CMe$_2$—CL) |
| 42 | TFPr | C2 | Me | Me | CL | (TFPr—)$_7$ T8 (—C2—OCO—CMe$_2$—CL) |
| 43 | Et | C3 | Me | Me | CL | (Et—)$_7$ T8 (—C3—OCO—CMe$_2$—CL) |
| 44 | IBu | C3 | Me | Me | CL | (IBu—)$_7$ T8 (—C3—OCO—CMe$_2$—CL) |
| 45 | IOc | C3 | Me | Me | CL | (IOc—)$_7$ T8 (—C3—OCO—CMe$_2$—CL) |
| 46 | CPe | C3 | Me | Me | CL | (CPe—)$_7$ T8 (—C3—OCO—CMe$_2$—CL) |
| 47 | CHe | C3 | Me | Me | CL | (CHe—)$_7$ T8 (—C3—OCO—CMe$_2$—CL) |
| 48 | Ph | C3 | Me | Me | CL | (Ph—)$_7$ T8 (—C3—OCO—CMe$_2$—CL) |
| 49 | TFPr | C3 | Me | Me | CL | (TFPr—)$_7$ T8 (—C3—OCO—CMe$_2$—CL) |
| 50 | Et | C4 | Me | Me | CL | (Et—)$_7$ T8 (—C4—OCO—CMe$_2$—CL) |
| 51 | IBu | C4 | Me | Me | CL | (IBu—)$_7$ T8 (—C4—OCO—CMe$_2$—CL) |
| 52 | IOc | C4 | Me | Me | CL | (IOc—)$_7$ T8 (—C4—OCO—CMe$_2$—CL) |
| 53 | CPe | C4 | Me | Me | CL | (CPe—)$_7$ T8 (—C4—OCO—CMe$_2$—CL) |
| 54 | CHe | C4 | Me | Me | CL | (CHe—)$_7$ T8 (—C4—OCO—CMe$_2$—CL) |
| 55 | Ph | C4 | Me | Me | CL | (Ph—)$_7$ T8 (—C4—OCO—CMe$_2$—CL) |
| 56 | TFPr | C4 | Me | Me | CL | (TFPr—)$_7$ T8 (—C4—OCO—CMe$_2$—CL) |
| 57 | Et | C5 | Me | Me | CL | (Et—)$_7$ T8 (—C5—OCO—CMe$_2$—CL) |
| 58 | IBu | C5 | Me | Me | CL | (IBu—)$_7$ T8 (—C5—OCO—CMe$_2$—CL) |
| 59 | IOc | C5 | Me | Me | CL | (IOc—)$_7$ T8 (—C5—OCO—CMe$_2$—CL) |
| 60 | CPe | C5 | Me | Me | CL | (CPe—)$_7$ T8 (—C5—OCO—CMe$_2$—CL) |

TABLE 4

| No. | R$^{12}$ | Z$^1$ | R$^2$ | R$^3$ | X$^1$ | Formula (6) |
|---|---|---|---|---|---|---|
| 61 | CHe | C5 | Me | Me | CL | (CHe—)$_7$ T8 (—C5—OCO—CMe$_2$—CL) |
| 62 | Ph | C5 | Me | Me | CL | (Ph—)$_7$ T8 (—C5—OCO—CMe$_2$—CL) |
| 63 | TFPr | C5 | Me | Me | CL | (TFPr—)$_7$ T8 (—C5—OCO—CMe$_2$—CL) |
| 64 | Et | C2OC3 | Me | Me | CL | (Et—)$_7$ T8 (—C2OC3—OCO—CMe$_2$—CL) |
| 65 | IBu | C2OC3 | Me | Me | CL | (IBu—)$_7$ T8 (—C2OC3—OCO—CMe$_2$—CL) |
| 66 | IOc | C2OC3 | Me | Me | CL | (IOc—)$_7$ T8 (—C2OC3—OCO—CMe$_2$—CL) |

TABLE 4-continued

| No. | R$^{12}$ | Z$^1$ | R$^2$ | R$^3$ | X$^1$ | Formula (6) |
|---|---|---|---|---|---|---|
| 67 | CPe | C2OC3 | Me | Me | CL | (CPe—)$_7$ T8 (—C2OC3—OCO—CMe$_2$—CL) |
| 68 | CHe | C2OC3 | Me | Me | CL | (CHe—)$_7$ T8 (—C2OC3—OCO—CMe$_2$—CL) |
| 69 | Ph | C2OC3 | Me | Me | CL | (Ph—)$_7$ T8 (—C2OC3—OCO—CMe$_2$—CL) |
| 70 | TFPr | C2OC3 | Me | Me | CL | (TFPr—)$_7$ T8 (—C2OC3—OCO—CMe$_2$—CL) |
| 71 | Et | C2 | Et | Et | CL | (Et—)$_7$ T8 (—C2—OCO—CEt$_2$—CL) |
| 72 | IBu | C2 | Et | Et | CL | (IBu—)$_7$ T8 (—C2—OCO—CEt$_2$—CL) |
| 73 | IOc | C2 | Et | Et | CL | (IOc—)$_7$ T8 (—C2—OCO—CEt$_2$—CL) |
| 74 | CPe | C2 | Et | Et | CL | (CPe—)$_7$ T8 (—C2—OCO—CEt$_2$—CL) |
| 75 | CHe | C2 | Et | Et | CL | (CHe—)$_7$ T8 (—C2—OCO—CEt$_2$—CL) |
| 76 | Ph | C2 | Et | Et | CL | (Ph—)$_7$ T8 (—C2—OCO—CEt$_2$—CL) |
| 77 | TFPr | C2 | Et | Et | CL | (TFPr—)$_7$ T8 (—C2—OCO—CEt$_2$—CL) |
| 78 | Et | C3 | Et | Et | CL | (Et—)$_7$ T8 (—C3—OCO—CEt$_2$—CL) |
| 79 | IBu | C3 | Et | Et | CL | (IBu—)$_7$ T8 (—C3—OCO—CEt$_2$—CL) |
| 80 | IOc | C3 | Et | Et | CL | (IOc—)$_7$ T8 (—C3—OCO—CEt$_2$—CL) |
| 81 | CPe | C3 | Et | Et | CL | (CPe—)$_7$ T8 (—C3—OCO—CEt$_2$—CL) |
| 82 | CHe | C3 | Et | Et | CL | (CHe—)$_7$ T8 (—C3—OCO—CEt$_2$—CL) |
| 83 | Ph | C3 | Et | Et | CL | (Ph—)$_7$ T8 (—C3—OCO—CEt$_2$—CL) |
| 84 | TFPr | C3 | Et | Et | CL | (TFPr—)$_7$ T8 (—C3—OCO—CEt$_2$—CL) |
| 85 | Et | C4 | Et | Et | CL | (Et—)$_7$ T8 (—C4—OCO—CEt$_2$—CL) |
| 86 | IBu | C4 | Et | Et | CL | (IBu—)$_7$ T8 (—C4—OCO—CEt$_2$—CL) |
| 87 | IOc | C4 | Et | Et | CL | (IOc—)$_7$ T8 (—C4—OCO—CEt$_2$—CL) |
| 88 | CPe | C4 | Et | Et | CL | (CPe—)$_7$ T8 (—C4—OCO—CEt$_2$—CL) |
| 89 | CHe | C4 | Et | Et | CL | (CHe—)$_7$ T8 (—C4—OCO—CEt$_2$—CL) |
| 90 | Ph | C4 | Et | Et | CL | (Ph—)$_7$ T8 (—C4—OCO—CEt$_2$—CL) |

TABLE 5

| No. | R$^{12}$ | Z$^1$ | R$^2$ | R$^3$ | X$^1$ | Formula (6) |
|---|---|---|---|---|---|---|
| 91 | TFPr | C4 | Et | Et | CL | (TFPr—)$_7$ T8 (—C4—OCO—CEt$_2$—CL) |
| 92 | Et | C5 | Et | Et | CL | (Et—)$_7$ T8 (—C5—OCO—CEt$_2$—CL) |
| 93 | IBu | C5 | Et | Et | CL | (IBu—)$_7$ T8 (—C5—OCO—CEt$_2$—CL) |
| 94 | IOc | C5 | Et | Et | CL | (IOc—)$_7$ T8 (—C5—OCO—CEt$_2$—CL) |
| 95 | CPe | C5 | Et | Et | CL | (CPe—)$_7$ T8 (—C5—OCO—CEt$_2$—CL) |
| 96 | CHe | C5 | Et | Et | CL | (CHe—)$_7$ T8 (—C5—OCO—CEt$_2$—CL) |
| 97 | Ph | C5 | Et | Et | CL | (Ph—)$_7$ T8 (—C5—OCO—CEt$_2$—CL) |
| 98 | TFPr | C5 | Et | Et | CL | (TFPr—)$_7$ T8 (—C5—OCO—CEt$_2$—CL) |
| 99 | Et | C2OC3 | Et | Et | CL | (Et—)$_7$ T8 (—C2OC3—OCO—CEt$_2$—CL) |
| 100 | IBu | C2OC3 | Et | Et | CL | (IBu—)$_7$ T8 (—C2OC3—OCO—CEt$_2$—CL) |
| 101 | IOc | C2OC3 | Et | Et | CL | (IOc—)$_7$ T8 (—C2OC3—OCO—CEt$_2$—CL) |
| 102 | CPe | C2OC3 | Et | Et | CL | (CPe—)$_7$ T8 (—C2OC3—OCO—CEt$_2$—CL) |
| 103 | CHe | C2OC3 | Et | Et | CL | (CHe—)$_7$ T8 (—C2OC3—OCO—CEt$_2$—CL) |
| 104 | Ph | C2OC3 | Et | Et | CL | (Ph—)$_7$ T8 (—C2OC3—OCO—CEt$_2$—CL) |
| 105 | TFPr | C2OC3 | Et | Et | CL | (TFPr—)$_7$ T8 (—C2OC3—OCO—CEt$_2$—CL) |
| 106 | Et | C2 | Me | H | BR | (Et—)$_7$ T8 (—C2—OCO—CHMe—BR) |
| 107 | IBu | C2 | Me | H | BR | (IBu—)$_7$ T8 (—C2—OCO—CHMe—BR) |
| 108 | IOc | C2 | Me | H | BR | (IOc—)$_7$ T8 (—C2—OCO—CHMe—BR) |
| 109 | CPe | C2 | Me | H | BR | (CPe—)$_7$ T8 (—C2—OCO—CHMe—BR) |
| 110 | CHe | C2 | Me | H | BR | (CHe—)$_7$ T8 (—C2—OCO—CHMe—BR) |
| 111 | Ph | C2 | Me | H | BR | (Ph—)$_7$ T8 (—C2—OCO—CHMe—BR) |
| 112 | TFPr | C2 | Me | H | BR | (TFPr—)$_7$ T8 (—C2—OCO—CHMe—BR) |
| 113 | Et | C3 | Me | H | BR | (Et—)$_7$ T8 (—C3—OCO—CHMe—BR) |
| 114 | IBu | C3 | Me | H | BR | (IBu—)$_7$ T8 (—C3—OCO—CHMe—BR) |
| 115 | IOc | C3 | Me | H | BR | (IOc—)$_7$ T8(—C3—OCO—CHMe—BR) |
| 116 | CPe | C3 | Me | H | BR | (CPe—)$_7$ T8 (—C3—OCO—CHMe—BR) |
| 117 | CHe | C3 | Me | H | BR | (CHe—)$_7$ T8 (—C3—OCO—CHMe—BR) |
| 118 | Ph | C3 | Me | H | BR | (Ph—)$_7$ T8 (—C3—OCO—CHMe—BR) |
| 119 | TFPr | C3 | Me | H | BR | (TFPr—)$_7$ T8 (—C3—OCO—CHMe—BR) |
| 120 | Et | C4 | Me | H | BR | (Et—)$_7$ T8 (—C4—OCO—CHMe—BR) |

TABLE 6

| No. | R$^{12}$ | Z$^1$ | R$^2$ | R$^3$ | X$^1$ | Formula (6) |
|---|---|---|---|---|---|---|
| 121 | IBu | C4 | Me | H | BR | (IBu—)$_7$ T8 (—C4—OCO—CHMe—BR) |
| 122 | IOc | C4 | Me | H | BR | (IOc—)$_7$ T8 (—C4—OCO—CHMe—BR) |
| 123 | CPe | C4 | Me | H | BR | (CPe—)$_7$ T8 (—C4—OCO—CHMe—BR) |
| 124 | CHe | C4 | Me | H | BR | (CHe—)$_7$ T8 (—C4—OCO—CHMe—BR) |
| 125 | Ph | C4 | Me | H | BR | (Ph—)$_7$ T8 (—C4—OCO—CHMe—BR) |
| 126 | TFPr | C4 | Me | H | BR | (TFPr—)$_7$ T8 (—C4—OCO—CHMe—BR) |
| 127 | Et | C5 | Me | H | BR | (Et—)$_7$ T8 (—C5—OCO—CHMe—BR) |
| 128 | IBu | C5 | Me | H | BR | (IBu—)$_7$ T8 (—C5—OCO—CHMe—BR) |

TABLE 6-continued

| No. | R$^{12}$ | Z$^1$ | R$^2$ | R$^3$ | X$^1$ | Formula (6) |
|---|---|---|---|---|---|---|
| 129 | IOc | C5 | Me | H | BR | (IOc—)$_7$ T8 (—C5—OCO—CHMe—BR) |
| 130 | CPe | C5 | Me | H | BR | (CPe—)$_7$ T8 (—C5—OCO—CHMe—BR) |
| 131 | CHe | C5 | Me | H | BR | (CHe—)$_7$ T8 (—C5—OCO—CHMe—BR) |
| 132 | Ph | C5 | Me | H | BR | (Ph—)$_7$ T8 (—C5—OCO—CHMe—BR) |
| 133 | TFPr | C5 | Me | H | BR | (TFPr—)$_7$ T8 (—C5—OCO—CHMe—BR) |
| 134 | Et | C2OC3 | Me | H | BR | (Et—)$_7$ T8 (—C2OC3—OCO—CHMe—BR) |
| 135 | IBu | C2OC3 | Me | H | BR | (IBu—)$_7$ T8 (—C2OC3—OCO—CHMe—BR) |
| 136 | IOc | C2OC3 | Me | H | BR | (IOc—)$_7$ T8 (—C2OC3—OCO—CHMe—BR) |
| 137 | CPe | C2OC3 | Me | H | BR | (CPe—)$_7$ T8 (—C2OC3—OCO—CHMe—BR) |
| 138 | CHe | C2OC3 | Me | H | BR | (CHe—)$_7$ T8 (—C2OC3—OCO—CHMe—BR) |
| 139 | Ph | C2OC3 | Me | H | BR | (Ph—)$_7$ T8 (—C2OC3—OCO—CHMe—BR) |
| 140 | TFPr | C2OC3 | Me | H | BR | (TFPr—)$_7$ T8 (—C2OC3—OCO—CHMe—BR) |
| 141 | Et | C2 | Me | Me | BR | (Et—)$_7$ T8 (—C2—OCO—CMe$_2$—BR) |
| 142 | IBu | C2 | Me | Me | BR | (IBu—)$_7$ T8 (—C2—OCO—CMe$_2$—BR) |
| 143 | IOc | C2 | Me | Me | BR | (IOc—)$_7$ T8 (—C2—OCO—CMe$_2$—BR) |
| 144 | CPe | C2 | Me | Me | BR | (CPe—)$_7$ T8 (—C2—OCO—CMe$_2$—BR) |
| 145 | CHe | C2 | Me | Me | BR | (CHe—)$_7$ T8 (—C2—OCO—CMe$_2$—BR) |
| 146 | Ph | C2 | Me | Me | BR | (Ph—)$_7$ T8 (—C2—OCO—CMe$_2$—BR) |
| 147 | TFPr | C2 | Me | Me | BR | (TFPr—)$_7$ T8 (—C2—OCO—CMe$_2$—BR) |
| 148 | Et | C3 | Me | Me | BR | (Et—)$_7$ T8 (—C3—OCO—CMe$_2$—BR) |
| 149 | IBu | C3 | Me | Me | BR | (IBu—)$_7$ T8 (—C3—OCO—CMe$_2$—BR) |
| 150 | IOc | C3 | Me | Me | BR | (IOc—)$_7$ T8 (—C3—OCO—CMe$_2$—BR) |

TABLE 7

| No. | R$^{12}$ | Z$^1$ | R$^2$ | R$^3$ | X$^1$ | Formula (6) |
|---|---|---|---|---|---|---|
| 151 | CPe | C3 | Me | Me | BR | (CPe—)$_7$ T8 (—C3—OCO—CMe$_2$—BR) |
| 152 | CHe | C3 | Me | Me | BR | (CHe—)$_7$ T8 (—C3—OCO—CMe$_2$—BR) |
| 153 | Ph | C3 | Me | Me | BR | (Ph—)$_7$ T8 (—C3—OCO—CMe$_2$—BR) |
| 154 | TFPr | C3 | Me | Me | BR | (TFPr—)$_7$ T8 (—C3—OCO—CMe$_2$—BR) |
| 155 | Et | C4 | Me | Me | BR | (Et—)$_7$ T8 (—C4—OCO—CMe$_2$—BR) |
| 156 | IBu | C4 | Me | Me | BR | (IBu—)$_7$ T8 (—C4—OCO—CMe$_2$—BR) |
| 157 | IOc | C4 | Me | Me | BR | (IOc—)$_7$ T8 (—C4—OCO—CMe$_2$—BR) |
| 158 | CPe | C4 | Me | Me | BR | (CPe—)$_7$ T8 (—C4—OCO—CMe$_2$—BR) |
| 159 | CHe | C4 | Me | Me | BR | (CHe—)$_7$ T8 (—C4—OCO—CMe$_2$—BR) |
| 160 | Ph | C4 | Me | Me | BR | (Ph—)$_7$ T8 (—C4—OCO—CMe$_2$—BR) |
| 161 | TFPr | C4 | Me | Me | BR | (TFPr—)$_7$ T8 (—C4—OCO—CMe$_2$—BR) |
| 162 | Et | C5 | Me | Me | BR | (Et—)$_7$ T8 (—C5—OCO—CMe$_2$—BR) |
| 163 | IBu | C5 | Me | Me | BR | (IBu—)$_7$ T8 (—C5—OCO—CMe$_2$—BR) |
| 164 | IOc | C5 | Me | Me | BR | (IOc—)$_7$ T8 (—C5—OCO—CMe$_2$—BR) |
| 165 | CPe | C5 | Me | Me | BR | (CPe—)$_7$ T8 (—C5—OCO—CMe$_2$—BR) |
| 166 | CHe | C5 | Me | Me | BR | (CHe—)$_7$ T8 (—C5—OCO—CMe$_2$—BR) |
| 167 | Ph | C5 | Me | Me | BR | (Ph—)$_7$ T8 (—C5—OCO—CMe$_2$—BR) |
| 168 | TFPr | C5 | Me | Me | BR | (TFPr—)$_7$ T8 (—C5—OCO—CMe$_2$—BR) |
| 169 | Et | C2OC3 | Me | Me | BR | (Et—)$_7$ T8 (—C2OC3—OCO—CMe$_2$—BR) |
| 170 | IBu | C2OC3 | Me | Me | BR | (IBu—)$_7$ T8 (—C2OC3—OCO—CMe$_2$—BR) |
| 171 | IOc | C2OC3 | Me | Me | BR | (IOc—)$_7$ T8 (—C2OC3—OCO—CMe$_2$—BR) |
| 172 | CPe | C2OC3 | Me | Me | BR | (CPe—)$_7$ T8 (—C2OC3—OCO—CMe$_2$—BR) |
| 173 | CHe | C2OC3 | Me | Me | BR | (CHe—)$_7$ T8 (—C2OC3—OCO—CMe$_2$—BR) |
| 174 | Ph | C2OC3 | Me | Me | BR | (Ph—)$_7$ T8 (—C2OC3—OCO—CMe$_2$—BR) |
| 175 | TFPr | C2OC3 | Me | Me | BR | (TFPr—)$_7$ T8 (—C2OC3—OCO—CMe$_2$—BR) |
| 176 | Et | C2 | Et | Et | BR | (Et—)$_7$ T8 (—C2—OCO—CEt$_2$—BR) |
| 177 | IBu | C2 | Et | Et | BR | (IBu—)$_7$ T8 (—C2—OCO—CEt$_2$—BR) |
| 178 | IOc | C2 | Et | Et | BR | (IOc—)$_7$ T8 (—C2—OCO—CEt$_2$—BR) |
| 179 | CPe | C2 | Et | Et | BR | (CPe—)$_7$ T8 (—C2—OCO—CEt$_2$—BR) |
| 180 | CHe | C2 | Et | Et | BR | (CHe—)$_7$ T8 (—C2—OCO—CEt$_2$—BR) |

TABLE 8

| No. | R$^{12}$ | Z$^1$ | R$^2$ | R$^3$ | X$^1$ | Formula (6) |
|---|---|---|---|---|---|---|
| 151 | CPe | C3 | Me | Me | BR | (CPe—)$_7$ T8 (—C3—OCO—CMe$_2$—BR) |
| 152 | CHe | C3 | Me | Me | BR | (CHe—)$_7$ T8 (—C3—OCO—CMe$_2$—BR) |
| 153 | Ph | C3 | Me | Me | BR | (Ph—)$_7$ T8 (—C3—OCO—CMe$_2$—BR) |
| 154 | TFPr | C3 | Me | Me | BR | (TFPr—)$_7$ T8 (—C3—OCO—CMe$_2$—BR) |
| 155 | Et | C4 | Me | Me | BR | (Et—)$_7$ T8 (—C4—OCO—CMe$_2$—BR) |
| 156 | IBu | C4 | Me | Me | BR | (IBu—)$_7$ T8 (—C4—OCO—CMe$_2$—BR) |
| 157 | IOc | C4 | Me | Me | BR | (IOc—)$_7$ T8 (—C4—OCO—CMe$_2$—BR) |
| 158 | CPe | C4 | Me | Me | BR | (CPe—)$_7$ T8 (—C4—OCO—CMe$_2$—BR) |
| 159 | CHe | C4 | Me | Me | BR | (CHe—)$_7$ T8 (—C4—OCO—CMe$_2$—BR) |
| 160 | Ph | C4 | Me | Me | BR | (Ph—)$_7$ T8 (—C4—OCO—CMe$_2$—BR) |

TABLE 8-continued

| No. | $R^{12}$ | $Z^1$ | $R^2$ | $R^3$ | $X^1$ | Formula (6) |
|---|---|---|---|---|---|---|
| 161 | TFPr | C4 | Me | Me | BR | (TFPr—)$_7$ T8 (—C4—OCO—CMe$_2$—BR) |
| 162 | Et | C5 | Me | Me | BR | (Et—)$_7$ T8 (—C5—OCO—CMe$_2$—BR) |
| 163 | IBu | C5 | Me | Me | BR | (IBu—)$_7$ T8 (—C5—OCO—CMe$_2$—BR) |
| 164 | IOc | C5 | Me | Me | BR | (IOc—)$_7$ T8 (—C5—OCO—CMe$_2$—BR) |
| 165 | CPe | C5 | Me | Me | BR | (CPe—)$_7$ T8 (—C5—OCO—CMe$_2$—BR) |
| 166 | CHe | C5 | Me | Me | BR | (CHe—)$_7$ T8 (—C5—OCO—CMe$_2$—BR) |
| 167 | Ph | C5 | Me | Me | BR | (Ph—)$_7$ T8 (—C5—OCO—CMe$_2$—BR) |
| 168 | TFPr | C5 | Me | Me | BR | (TFPr—)$_7$ T8 (—C5—OCO—CMe$_2$—BR) |
| 169 | Et | C2OC3 | Me | Me | BR | (Et—)$_7$ T8 (—C2OC3—OCO—CMe$_2$—BR) |
| 170 | IBu | C2OC3 | Me | Me | BR | (IBu—)$_7$ T8 (—C2OC3—OCO—CMe$_2$—BR) |
| 171 | IOc | C2OC3 | Me | Me | BR | (IOc—)$_7$ T8 (—C2OC3—OCO—CMe$_2$—BR) |
| 172 | CPe | C2OC3 | Me | Me | BR | (CPe—)$_7$ T8 (—C2OC3—OCO—CMe$_2$—BR) |
| 173 | CHe | C2OC3 | Me | Me | BR | (CHe—)$_7$ T8 (—C2OC3—OCO—CMe$_2$—BR) |
| 174 | Ph | C2OC3 | Me | Me | BR | (Ph—)$_7$ T8 (—C2OC3—OCO—CMe$_2$—BR) |
| 175 | TFPr | C2OC3 | Me | Me | BR | (TFPr—)$_7$ T8 (—C2OC3—OCO—CMe$_2$—BR) |
| 176 | Et | C2 | Et | Et | BR | (Et—)$_7$ T8 (—C2—OCO—CEt$_2$—BR) |
| 177 | IBu | C2 | Et | Et | BR | (IBu—)$_7$ T8 (—C2—OCO—CEt$_2$—BR) |
| 178 | IOc | C2 | Et | Et | BR | (IOc—)$_7$ T8 (—C2—OCO—CEt$_2$—BR) |
| 179 | CPe | C2 | Et | Et | BR | (CPe—)$_7$ T8 (—C2—OCO—CEt$_2$—BR) |
| 180 | CHe | C2 | Et | Et | BR | (CHe—)$_7$ T8 (—C2—OCO—CEt$_2$—BR) |

TABLE 9

| No. | $R^{12}$ | $Z^1$ | $R^2$ | $R^3$ | $X^1$ | Formula (6) |
|---|---|---|---|---|---|---|
| 181 | Ph | C2 | Et | Et | BR | (Ph—)$_7$ T8 (—C2—OCO—CEt$_2$—BR) |
| 182 | TFPr | C2 | Et | Et | BR | (TFPr—)$_7$ T8 (—C2—OCO—CEt$_2$—BR) |
| 183 | Et | C3 | Et | Et | BR | (Et—)$_7$ T8 (—C3—OCO—CEt$_2$—BR) |
| 184 | IBu | C3 | Et | Et | BR | (IBu—)$_7$ T8 (—C3—OCO—CEt$_2$—BR) |
| 185 | IOc | C3 | Et | Et | BR | (IOc—)$_7$ T8 (—C3—OCO—CEt$_2$—BR) |
| 186 | CPe | C3 | Et | Et | BR | (CPe—)$_7$ T8 (—C3—OCO—CEt$_2$—BR) |
| 187 | CHe | C3 | Et | Et | BR | (CHe—)$_7$ T8 (—C3—OCO—CEt$_2$—BR) |
| 188 | Ph | C3 | Et | Et | BR | (Ph—)$_7$ T8 (—C3—OCO—CEt$_2$—BR) |
| 189 | TFPr | C3 | Et | Et | BR | (TFPr—)$_7$ T8 (—C3—OCO—CEt$_2$—BR) |
| 190 | Et | C4 | Et | Et | BR | (Et—)$_7$ T8 (—C4—OCO—CEt$_2$—BR) |
| 191 | IBu | C4 | Et | Et | BR | (IBu—)$_7$ T8 (—C4—OCO—CEt$_2$—BR) |
| 192 | IOc | C4 | Et | Et | BR | (IOc—)$_7$ T8 (—C4—OCO—CEt$_2$—BR) |
| 193 | CPe | C4 | Et | Et | BR | (CPe—)$_7$ T8 (—C4—OCO—CEt$_2$—BR) |
| 194 | CHe | C4 | Et | Et | BR | (CHe—)$_7$ T8 (—C4—OCO—CEt$_2$—BR) |
| 195 | Ph | C4 | Et | Et | BR | (Ph—)$_7$ T8 (—C4—OCO—CEt$_2$—BR) |
| 196 | TFPr | C4 | Et | Et | BR | (TFPr—)$_7$ T8 (—C4—OCO—CEt$_2$—BR) |
| 197 | Et | C5 | Et | Et | BR | (Et—)$_7$ T8 (—C5—OCO—CEt$_2$—BR) |
| 198 | IBu | C5 | Et | Et | BR | (IBu—)$_7$ T8 (—C5—OCO—CEt$_2$—BR) |
| 199 | IOc | C5 | Et | Et | BR | (IOc—)$_7$ T8 (—C5—OCO—CEt$_2$—BR) |
| 200 | CPe | C5 | Et | Et | BR | (CPe—)$_7$ T8 (—C5—OCO—CEt$_2$—BR) |
| 201 | CHe | C5 | Et | Et | BR | (CHe—)$_7$ T8 (—C5—OCO—CEt$_2$—BR) |
| 202 | Ph | C5 | Et | Et | BR | (Ph—)$_7$ T8 (—C5—OCO—CEt$_2$—BR) |
| 203 | TFPr | C5 | Et | Et | BR | (TFPr—)$_7$ T8 (—C5—OCO—CEt$_2$—BR) |
| 204 | Et | C2OC3 | Et | Et | BR | (Et—)$_7$ T8 (—C2OC3—OCO—CEt$_2$—BR) |
| 205 | IBu | C2OC3 | Et | Et | BR | (IBu—)$_7$ T8 (—C2OC3—OCO—CEt$_2$—BR) |
| 206 | IOc | C2OC3 | Et | Et | BR | (IOc—)$_7$ T8 (—C2OC3—OCO—CEt$_2$—BR) |
| 207 | CPe | C2OC3 | Et | Et | BR | (CPe—)$_7$ T8 (—C2OC3—OCO—CEt$_2$—BR) |
| 208 | CHe | C2OC3 | Et | Et | BR | (CHe—)$_7$ T8 (—C2OC3—OCO—CEt$_2$—BR) |
| 209 | Ph | C2OC3 | Et | Et | BR | (Ph—)$_7$ T8 (—C2OC3—OCO—CEt$_2$—BR) |
| 210 | TFPr | C2OC3 | Et | Et | BR | (TFPr—)$_7$ T8 (—C2OC3—OCO—CEt$_2$—BR) |

The examples shown in Table 2 to Table 9 are the preferred examples of the compounds of the present invention. In addition thereto, preferred as well are the compounds in which $R^{12}$ in Formula (6) is tridecafluoro-1,1,2,2-tetrahydrooctyl and in which $Z^1$ is —(CH$_2$)$_2$—, —(CH$_2$)$_3$—, —(CH$_2$)$_4$—, —(CH$_2$)$_5$— or —C$_2$H$_4$—O—C$_3$H$_6$—. The compound in which $R^{12}$ is 3,3,3-trifluoropropyl or non-substituted phenyl in Formula (6) is most preferred.

Next, an addition-polymerizable monomer for which the compound (1) can be used as a polymerization initiator shall be explained. This addition-polymerizable monomer is a monomer having at least one addition-polymerizable double bond. One of the examples of a monofunctional monomer having one addition-polymerizable double bond is a (meth) acrylic acid base monomer. The specific examples thereof are (meth)acrylic acid, methyl(meth)acrylate, ethyl (meth)acrylate, n-propyl(meth)acrylate, isopropyl (meth)acrylate, n-butyl(meth)acrylate, isobutyl (meth)acrylate, tert-butyl(meth) acrylate, n-pentyl (meth)acrylate, n-hexyl(meth)acrylate, cyclohexyl (meth)acrylate, n-heptyl(meth)acrylate, n-octyl (meth)acrylate, 2-ethylhexyl(meth)acrylate, nonyl (meth) acrylate, decyl(meth)acrylate, dodecyl(meth)acrylate, phenyl(meth)acrylate, toluyl(meth)acrylate, benzyl (meth)acrylate, 2-methoxyethyl(meth)acrylate, 3-methoxypropyl(meth) acrylate, 3-methoxybutyl(meth)acrylate, 2-hydroxyethyl (meth)acrylate, 2-hydroxypropyl(meth)acrylate, stearyl (meth)acrylate, glycidyl(meth)acrylate, 3-ethyl-3-(meth) acryloyloxymethyloxetane, 2-(meth)

acryloyloxyethylisocyanate, 2-aminoethyl(meth)acrylate, 2-(2-bromopropionylyloxy)ethyl(meth)acrylate, 2-(2-bromoisobutyryloxy)ethyl(meth)acrylate, 1-(meth)acryloxy-2-phenyl-2-(2,2,6,6-tetramethyl-piperidinyloxy)ethane, (1-(4-((4-(meth)acryloxy)ethoxyethyl)phenylethoxy)piperidine, γ-(methacryloyloxypropyl)trimethoxysilane, 3-(3,5,7,9,11,13,15-heptaethylpentacyclo[9.5.1.1$^{3,9}$.1$^{5,15}$.1$^{7,13}$]octasiloxane-1-yl)propyl(meth)acrylate, 3-(3,5,7,9,11,13,15-heptaisobutylpentacyclo[9.5.1.1$^{3,9}$.1$^{5,15}$.1$^{7,13}$]octasiloxane-1-yl)propyl(meth)acrylate, 3-(3,5,7,9,11,13,15-heptaisooctylpentacyclo[9.5.1.1$^{3,9}$.1$^{5,15}$.1$^{7,13}$]-octasiloxane-1-yl)propyl(meth)acrylate, 3-(3,5,7,9,11,13,15-heptacyclopentylpentacyclo-[9.5.1.1$^{3,9}$.1$^{5,15}$.1$^{7,13}$]octasiloxane-1-yl)propyl (meth)acrylate, 3-(3,5,7,9,11,13,15-heptaphenylpentacyclo[9.5.1.1$^{3,9}$.1$^{5,15}$.1$^{7,13}$]-octasiloxane-1-yl)propyl(meth)acrylate, 3-[(3,5,7,9,11,13,15-heptaethylpentacyclo-[9.5.1.1$^{3,9}$.1$^{5,15}$.1$^{7,13}$]octasiloxane-1-yloxy)dimethylsilyl]propyl(meth)acrylate, 3-[(3,5,7,9,11,13,15-heptaisobutylpentacyclo[(9.5.1.1$^{3,9}$.1$^{5,15}$.1$^{7,13}$]octasiloxane-1-yloxy)dimethylsilyl]propyl(meth)acrylate, 3-[(3,5,7,9,11,13,15-heptaisooctylpentacyclo[9.5.1.1$^{3,9}$.1$^{5,15}$.1$^{7,13}$]octasiloxane-1-yloxy)dimethylsilyl]propyl(meth)acrylate, 3-[(3,5,7,9,11,13,15-heptacyclopentylpentacyclo[9.5.1.1$^{3,9}$.1$^{5,15}$.1$^{7,13}$]octasiloxane-1-yloxy)dimethylsilyl]propyl(meth)acrylate, 3-[(3,5,7,9,11,13,15-heptaphenylpentacyclo[9.5.1.1$^{3,9}$.1$^{5,15}$.1$^{7,13}$]octasiloxane-1-yloxy)dimethylsilyl]propyl(meth)acrylate, ethylene oxide adducts of (meth)acrylic acid, trifluoromethylmethyl(meth)acrylate, 2-trifluoromethylethyl (meth)acrylate, 2-perfluoroethylethyl (meth)acrylate, 2-perfluoroethyl-2-perfluorobutylethyl (meth)acrylate, 2-perfluoroethyl(meth)acrylate, trifluoromethyl(meth)acrylate, diperfluoromethylmethyl (meth)acrylate, 2-perfluoromethyl-2-perfluoroethylethyl (meth)acrylate, 2-perfluorohexylethyl(meth)acrylate, 2-perfluorodecylethyl(meth)acrylate and 2-perfluorohexadecylethyl(meth)acrylate.

Another example of the monofunctional monomer is a styrene base monomer. The specific examples thereof are styrene, vinyltoluene, α-methylstyrene, p-chlorostyrene, p-chloromethylstyrene, m-chloromethylstyrene, o-aminostyrene, p-styrenechlorosulfonic acid, styrenesulfonic acid and salts thereof, vinylphenylmethyl dithiocarbamate, 2-(2-bromopropionyloxy)styrene, 2-(2-bromo-isobutyryloxy)styrene, 1-(2-((4-vinylphenyl)-methoxy)-1-phenylethoxy)-2,2,6,6-tetramethyl-piperidine, 1-(4-vinylphenyl)-3,5,7,9,11,13,15-heptaethylpentacyclo-[9.5.1.1$^{3,9}$.1$^{5,15}$.1$^{7,13}$]-octasiloxane, 1-(4-vinylphenyl)-3,5,7,9,11,13,15-heptaisobutylpentacyclo[9.5.1.1$^{3,9}$.1$^{5,15}$.1$^{7,13}$]-octasiloxane, 1-(4-vinylphenyl)-3,5,7,9,11,13,15-heptaisooctylpentacyclo[9.5.1.1$^{3,9}$.1$^{5,15}$.1$^{7,13}$]-octasiloxane, 1-(4-vinylphenyl)-3,5,7,9,11,13,15-heptacyclopentylpentacyclo[9.5.1.1$^{3,9}$.1$^{5,15}$.1$^{7,13}$]octasiloxane, 1-(4-vinylphenyl)-3,5,7,9,11,13,15-heptaphenylpentacyclo[9.5.1.1$^{3,9}$.1$^{5,15}$.1$^{7,13}$]-octasiloxane, 3-(3,5,7,9,11,13,15-heptaethylpentacyclo[9.5.1.1$^{3,9}$.1$^{5,15}$.1$^{7,13}$]octasiloxane-1-yl)ethylstyrene, 3-(3,5,7,9,11,13,15-heptaisobutylpentacyclo[9.5.1.1$^{3,9}$.1$^{5,15}$.1$^{7,13}$]octasiloxane-1-yl)ethylstyrene, 3-(3,5,7,9,11,13,15-heptaisooctylpentacyclo[9.5.1.1$^{3,9}$.1$^{5,15}$.1$^{7,13}$]-octasiloxane-1-yl)ethylstyrene, 3-(3,5,7,9,11,13,15-heptacyclopentylpentacyclo[9.5.1.1$^{3,9}$.1$^{5,15}$.1$^{7,13}$]-octasiloxane-1-yl)ethylstyrene, 3-(3,5,7,9,11,13,15-heptaphenylpentacyclo[9.5.1.1$^{3,9}$.1$^{5,15}$.1$^{7,13}$]-octasiloxane-1-yl)ethylstyrene, 3-((3,5,7,9,11,13,15-heptaethylpentacyclo[9.5.1.1$^{3,9}$.1$^{5,15}$.1$^{7,13}$]octasiloxane-1-yloxy)dimethylsilyl]ethylstyrene, 3-((3,5,7,9,11,13,15-heptaisobutylpentacyclo-[9.5.1.1$^{3,9}$.1$^{5,15}$.1$^{7,13}$]octasiloxane-1-yloxy)dimethylsilyl)ethylstyrene, 3-((3,5,7,9,11,13,15-heptaisooctylpentacyclo-[9.5.1.1$^{3,9}$.1$^{5,15}$.1$^{7,13}$]octasiloxane-1-yloxy)dimethylsilyl)ethylstyrene, 3-((3,5,7,9,11,13,15-heptacyclopentylpentacyclo[9.5.1.1$^{3,9}$.1$^{5,15}$.1$^{7,13}$]-octasiloxane-1-yloxy)dimethylsilyl)ethylstyrene and 3-((3,5,7,9,11,13,15-heptaphenylpentacyclo-[9.5.1.1$^{3,9}$.1$^{5,15}$.1$^{7,13}$]octasiloxane-1-yloxy)dimethylsilyl]ethylstyrene.

The examples of the other monofunctional monomers are fluorine-containing vinyl monomers (perfluoroethylene, perfluoropropylene, vinylidene fluoride and the like), silicon-containing vinyl base monomers (vinyltrimethoxysilane, vinyltriethoxysilane and the like), maleic anhydride, maleic acid, monoalkyl esters and dialkyl esters of maleic acid, fumaric acid, monoalkyl esters and dialkyl esters of fumaric acid, maleimide base monomers (maleimide, methylmaleimide, ethylmaleimide, propylmaleimide, butylmaleimide, hexylmaleimide, octylmaleimide, dodecylmaleimide, stearylmaleimide, phenylmaleimide, cyclohexylmaleimide and the like), nitrile group-containing monomers (acrylonitrile, methacrylonitrile and the like), amide group-containing monomers (acrylamide, methacrylamide and the like), vinyl ester base monomers (vinyl acetate, vinyl propionate, vinyl pivalate, vinyl benzoate, vinyl cinnamate and the like), olefins (ethylene, propylene and the like), conjugated diene base monomers (butadiene, isoprene and the like), halogenated vinyls (vinyl chloride and the like), halogenated vinylidenes (vinylidene chloride and the like), halogenated allyls (allyl chloride and the like), allyl alcohol, vinylpyrrolidone, vinylpyridine, N-vinylcarbazole, methyl vinyl ketone and vinylisocyanate. Further, given as well are macromonomers which have one polymerizable double bond in a molecule and in which a principal chain is derived from styrene, (meth)acrylic acid ester and siloxane.

The examples of multifunctional monomers having two addition-polymerizable double bonds are di(meth)acrylate base monomers such as 1,3-butanediol di(meth)acrylate, 1,4-butanediol di(meth)acrylate, 1,6-hexanediol di(meth)acrylate, polyethylene glycol di(meth)acrylate, diethylene glycol di(meth)acrylate, neopentyl glycol di(meth)acrylate, triethylene glycol di(meth)acrylate, tripropylene glycol di(meth)acrylate, hydroxypivalic acid ester neopentyl glycol di(meth)acrylate, trimethylolpropane di(meth)acrylate, bis[(meth)acryloyloxyethoxy]bisphenol A, bis[(meth)acryloyloxyethoxy]tetrabromobisphenol A, bis[(meth)acryloyloxypolyethoxy]bisphenol A, 1,3-bis(hydroxyethyl)-5,5-dimethylhydantoin, 3-methylpentanediol di(meth)acrylate, di(meth)acrylates of hydroxypivalic acid ester neopentyl glycol derivatives and bis[(meth)acryloyloxypropyl]tetramethyldisiloxane and divinylbenzene. Further, given as well are macromonomers which have two polymerizable double bonds in a molecule and in which a principal chain is derived from styrene, (meth)acrylic acid ester and siloxane.

The examples of multifunctional monomers having three or more addition-polymerizable double bonds are trimethylolpropane tri(meth)acrylate, pentaerythritol tri(meth)acrylate, pentaerythritol tetra(meth)acrylate, dipentaerythritol monohydroxypenta(meth)acrylate, tris(2-hydroxyethylisocyanate)tri(meth)acrylate, tris(diethylene glycol)trimelate tri(meth)acrylate, 3,7,14-tris[(((meth)acryloyloxypropyl)-dimethylsiloxy)]-1,3,5,7,9,11,14-heptaethyltricyclo[7.3.3.1$^{5,11}$]heptasiloxane, 3,7,14-tris[(((meth)acryloyloxypropyl)dimethylsiloxy)]-1,3,5,7,9,11,14-heptaisobutyltricyclo[7.3.3.1$^{5,11}$]-heptasiloxane, 3,7,14-tris[(((meth)acryloyloxypropyl)dimethylsiloxy)]-1,3,5,7,9,11,14-heptaisooctyltricyclo[7.3.3.1$^{5,11}$]heptasiloxane, 3,7,14-tris[(((meth)acryloyloxypropyl)-dimethylsiloxy)]-1,3,5,7,9,11,14-heptacyclopentyltricyclo[7.3.3.1$^{5,11}$]heptasiloxane, 3,7,14-tris[(((meth)acryloyloxypropyl)dimethylsiloxy)]-1,3,5,7, 9,11,14-heptaphenyltricyclo[7.3.3.1^{5,11}]-heptasiloxane, octakis(3-(meth)acryloyloxypropyl-dimethylsiloxy)octasilsesquioxane and octakis(3-(meth)acryloyloxypropyl)octasilsesquioxane. Further, given as well are macromonomers which have two or more polymerizable double bonds in a molecule and in which a principal chain is derived from styrene, (meth)acrylic acid ester and siloxane.

The above monomers may be used alone or a plurality thereof may be copolymerized. When copolymerized, they may be random-copolymerized or block-copolymerized.

Next, a method for subjecting an addition-polymerizable monomer to atom transfer radical polymerization using the compound (6) as an initiator and a transition metal complex as a catalyst shall be explained. The atom transfer radical polymerization method in the present invention is one of living radical polymerization methods, and it is a method for radically polymerizing addition-polymerizable monomers using an organic halide or a halogenated sulfonyl compound as an initiator. This method is disclosed in J. Am. Chem. Soc., 1995, 117, 5614, Macromolecules, 1995, 28, 7901 and Science, 1996, 272, 866.

The preferred example of a transition metal complex used as a polymerization catalyst is a metal complex in which the 7th, 8th, 9th, 10th or 11th group element in the periodic table is used as center metal. More preferred catalyst is a complex of zero-valent copper, monovalent copper, divalent ruthenium, divalent iron or divalent nickel. Among them, the complex of copper is preferred. The examples of a monovalent copper compound are cuprous chloride, cuprous bromide, cuprous iodide, cuprous cyanide, cuprous oxide and cuprous perchlorate. When using the copper compounds, 2,2'-bipyridyl or derivatives thereof, 1,10-phenanthroline or derivatives thereof, polyamine(tetramethylethylenediamine, pentamethyldiethylenetriamine, hexamethyltris(2-aminoethyl)amine and the like) or polycyclic alkaloid such as L-(-)-sparteine is added as a ligand in order to enhance the catalyst activity. A tristriphenylphosphine complex (RuCl$_2$(PPh$_3$)$_3$) of divalent ruthenium chloride is also suited as the catalyst. When the ruthenium compound is used as the catalyst, aluminum alkoxides are added as an activating agent. Further, a bistriphenylphosphine complex (FeCl$_2$(PPh$_3$)$_2$) of divalent iron, a bistriphenylphosphine complex (NiCl$_2$(PPh$_3$)$_2$) of divalent nickel and a bistributylphosphine complex (NiBr$_2$(PBu$_3$)$_2$) of divalent nickel are also suited as the catalyst.

A solvent may be used for the polymerization reaction. The examples of the solvent used are hydrocarbon base solvents (benzene, toluene and the like), ether base solvents (diethyl ether, tetrahydrofuran, diphenyl ether, anisole, dimethoxybenzene and the like), halogenated hydrocarbon base solvents (methylene chloride, chloroform, chlorobenzene and the like), ketone base solvents (acetone, methyl ethyl ketone, methyl isobutyl ketone and the like), alcohol base solvents (methanol, ethanol, propanol, isopropanol, n-butyl alcohol, tert-butyl alcohol and the like), nitrile base solvents (acetonitrile, propionitrile, benzonitrile and the like), ester base solvents (ethyl acetate, butyl acetate and the like), carbonate base solvents (ethylene carbonate, propylene carbonate and the like), amide base solvents (N,N-dimethylformamide, N,N-dimethylacetamide and the like), hydrochlorofluorocarbon base solvents (HCFC-141b and HCFC-225), hydrofluorocarbon (HFCs) base solvents (HFCs having a carbon atom number of 2 to 4, 5 and 6 or more), perfluorocarbon base solvents (perfluoropentane and perfluorohexane), alicyclic hydrofluorocarbon base solvents (fluorocyclopentane and fluorocyclobutane), oxygen-containing fluorine base solvents (fluoroether, fluoropolyether fluoroketone and fluoroalcohol) and water. They may be used alone or two or more kinds thereof may be used in combination. The polymerization can be carried out as well in an emulsion system or a system in which a supercritical fluid CO$_2$ is used as a medium. The solvent which can be used shall not be restricted to these examples.

The atom transfer radical polymerization can be carried out under reduced pressure, atmospheric pressure or applied pressure according to the kind of the addition-polymerizable monomer and the kind of the solvent. An organic metal complex used in combination or a radical produced is likely to be deactivated when brought into contact with oxygen. In such case, the polymerizing speed is reduced, and a good living polymer is not obtained. Accordingly, it is important to carry out the polymerization under inert gas atmosphere of nitrogen or argon. In this reaction, dissolved oxygen in the polymerization system has to be removed in advance under reduced pressure. It is possible to shift the reaction system to a polymerization step as it is under reduced pressure after finishing the step of removing dissolved oxygen. Conventional processes can be adopted for the atom transfer radical polymerization, and it shall not specifically be restricted by a polymerization process. For example, bulk polymerization, solution polymerization, suspension polymerization, emulsion polymerization or bulk-suspension polymerization can be adopted. The polymerization temperature falls in a range of 0 to 200° C., and the preferred polymerization temperature falls in a range of a room temperature to 150° C.

A polymer obtained by using the compound (6) as an initiator by the process described above can be represented by Formula (7). The polymer represented by Formula (7) shall be described as the polymer (7).

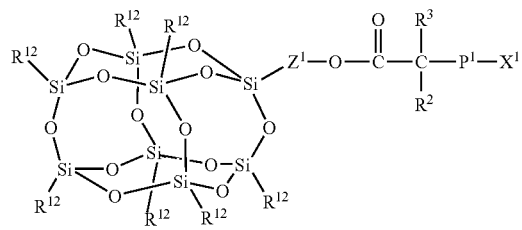

(7)

P$^1$ in Formula (7) is a chain of a structural unit obtained by polymerizing an addition-polymerizable monomer, and the other codes each have the same meanings as those of these codes in Formula (6).

Suitable selection of the kind of the addition-polymerizable monomer used makes it possible to control the structure of the compound (7) produced. For example, if the monomer is homopolymerized, silsesquioxane to which a homopolymer is bonded is obtained. If the plural monomers are added at the same time and polymerized, silsesquioxane to which a random copolymer is bonded is obtained. If used is a method in which the monomers are successively added, for example, a method in which the second monomer is added after finishing the polymerization of the first monomer to complete the polymerization, silsesquioxane to which a block copolymer is bonded is obtained. Repeating of this staged polymerization using plural monomers makes it possible to obtain silsesquioxane to which a multiblock copolymer is bonded. A cross-linked polymer having a three-dimensional network structure can be prepared by allowing a multifunctional monomer, if necessary, to coexist.

Silsesquioxanes to which highly branched type polymers are bonded can be obtained by using in combination a compound having a polymerizable functional group as well as a function as an initiator, for example, 2-(2-bromopropionyloxy)ethyl (meth)acrylate, 2-(2-bromoisobutyryloxy)ethyl (meth)acrylate, 2-(2-bromopropionyloxy)styrene and 2-(2-bromoisobutyryloxy)styrene when polymerizing a usual addition-polymerizable monomer. Further, combined use of compounds which are trialkoxysilane, polydimethylsiloxane and silsesquioxane and which have polymerizable functional groups such as a (meth)acryl group and a styryl group makes it possible to introduce a structural unit containing a silicon atom into the structure of the polymer. After copolymerized with an addition-polymerizable monomer having an initiating group which does not take part in atom transfer radical polymerization, for example, 1-(2-(4-vinylphenylmethoxy)-1-phenylethoxy)-2,2,6,6-tetramethylpyridine, 1-(meth)acryloxy-2-phenyl-2-(2,2,6,6-tetramethyl-1-piperidinyloxy) ethane, 1-(4-(4-(meth)acryloyloxyethoxyethyl) phenylethoxy)piperidine and vinylphenylmethyl dithiocarbamate, an addition-polymerizable monomer is further polymerized in the other polymerization mode (for example, nitroxyl polymerization and photo initiator-transfer agent-terminator polymerization) using the resulting polymer as an initiator, whereby a graft copolymer can be formed.

After copolymerized with a monomer having an oxetanyl group, for example, 3-ethyl-3-(meth)acryloyloxymethyloxetane, diphenyl-4-thiophenoxyphenylsulfonium hexafluoroantimonate or (4-pentadecyloxyphenyl)phenyliodonium hexafluoroantimonate is added as an initiator to the resulting polymer, whereby it can be subjected to photocationic polymerization.

Next, a refining method for the polymer (7) shall be explained. This compound is isolated and refined by efficiently removing the unreacted addition-polymerizable monomer. Various methods are available, and a refining method carried out by reprecipitation operation is preferred. This refining method is carried out in the following manner. First, a solvent which does not dissolve the polymer (7) but dissolves the unreacted monomer, a so-called precipitant is added to the polymerization reaction liquid containing the polymer (7) and the unreacted monomer to precipitate only the polymer (7). A preferred use amount of the precipitant is 20 to 50 times based on the weight of the polymerization reaction liquid described above.

The preferred precipitant is a solvent which is compatible with the solvent used in polymerization and which does not dissolve the polymer (7) at all but dissolves only the unreacted monomer and has a relatively low boiling point. The examples of the preferred precipitant are lower alcohols and aliphatic hydrocarbons. The particularly preferred precipitant is methanol and hexane. A repeating frequency of the reprecipitation operation is advisably increased in order to further raise a removing efficiency of the unreacted monomer. This method makes it possible to deposit only the polymer (7) in a poor solvent, and the polymer can readily be separated from the unreacted monomer by filtering operation.

The transition metal complex which is the polymerization catalyst remains in the compound (7) isolated by the method described above, and therefore problems such as coloring of the polymer, influence on the physical properties and environmental safety are brought about in a certain case. Accordingly, this catalyst residue has to be removed in finishing the polymerization reaction. The catalyst residue can be removed by adsorbing treatment using activated carbon. The examples of adsorbents other than activated carbon are ion exchange resins (acid, basic or chelate form) and inorganic adsorbents. The inorganic adsorbents have a character of a solid acid, a solid base or neutrality. They are particles having a porous structure and therefore have a very high adsorbing ability. It is also one of the characteristics of the inorganic adsorbents that they can be used in a wide temperature range extending from a low temperature to a high temperature.

The representative examples of the inorganic adsorbents are silicon dioxide, magnesium oxide, silica-alumina, aluminum silicate, activated alumina, clay base adsorbents such as acid clay and activated clay, zeolite base adsorbents, dawsonites compounds and hydrotalcites compounds. Zeolite includes natural products and synthetic products, and either can be used. Kinds such as a crystal form, an amorphous form, a noncrystal form, a glass form, a synthetic product and a natural product are available for silicon dioxide, and silicon dioxide of a powder form can be used in the present invention regardless of the kind. The examples of natural aluminum silicate are pumice, fly ash, kaoline, bentonite, activated clay and diatomaceous earth. Synthetic aluminum silicate has a large specific surface area and a high adsorbing ability. The hydrotalcites compound is carbonate hydrate of aluminum-magnesium hydroxide.

The acid adsorbents and the basic adsorbents are preferably used in combination with activated carbon. The examples of the acid adsorbents are acid clay, activated clay and aluminum silicate. The examples of the basic adsorbents are activated alumina, the zeolite base adsorbents and the hydrotalcites compounds each described above. These adsorbents may be used alone or in a mixture of two or more kinds thereof. The polymer (7) produced by the atom transfer radical polymerization can be refined by bringing into contact with activated alumina. A commercial product available from Aldrich Co., Ltd. can be used as activated alumina. When adsorbing treatment is carried out by using activated alumina in combination with the other adsorbents, the adsorbents can be mixed and brought into contact with the compound, but they may be brought into contact at the separate steps respectively. When brought into contact with the adsorbent, the reaction liquid may be used as it is or may be diluted with a solvent. The diluent may be selected from usual solvents only on the condition that it is not a poor solvent for the polymer. A temperature for treating with the adsorbent shall not specifically be restricted. The treatment may be carried out usually at 0 to 200° C. The preferred temperature range is a room temperature to 180° C. A use amount of the absorbent falls in a range of 0.1 to 500% by weight based on the weight of the polymer (7). Considering the economical efficiency and the operability, the preferred range is 0.5 to 10% by weight.

A method of a batch system in which stirring-mixing and solid-liquid separation are carried out by batch operation can be used for solid-liquid contact of the absorbent and the polymer liquid. In addition thereto, capable of being used is a method of a continuous system such as a fixed layer system in which the polymer liquid is allowed to pass through a vessel charged with the adsorbent, a moving layer system in which the liquid is allowed to pass through a moving layer of the adsorbent and a fluidized layer system in which the adsorbent is fluidized by a liquid to carry out adsorption. Further, a mixing and dispersing operation carried out by stirring can be combined, if necessary, with an operation for elevating the dispersing efficiency, such as shaking of the vessel and use of a supersonic wave. After the polymer liquid is brought into contact with the absorbent, the absorbent is removed by a method such as filtering, centrifugal separation and settling separation, and washing treatment is carried out if necessary to obtain the refined polymer liquid. Treatment by the absorbent may be carried out for the polymer (7) which is the final product, and it may be carried out for an intermediate product used for producing this polymer. For example, in the respective polymerizing steps of the block copolymer obtained by the atom transfer radical polymerization, this polymer can be isolated and subjected to adsorbing treatment. The polymer (7) subjected to treatment by the adsorbent may be separated by depositing in a poor solvent or distilling off volatile components such as the solvent under reduced pressure.

The analytical methods of a molecular weight and a molecular weight distribution of the polymer (7) produced shall be explained. Usually, a molecular weight of an addition polymer can be measured by gel permeation chromatography (GPC) using a calibration curve in which a linear polymer such as polystyrene and poly(methyl methacrylate) is used as a standard sample. A molecular weight and a molecular weight distribution of the polymer (7) can be analyzed as well by GPC.

The polymer (7) has silsesquioxane at an end part thereof, and therefore it can readily be decomposed under an acid condition or a basic condition. That is, an accuracy in molecular weight analysis of a polymer part can further be enhanced by cutting off an addition polymer from silsesquioxane and then measuring the molecular weight thereof. Hydrofluoric acid is preferably used when decomposing the polymer (7) under an acid condition. Potassium hydroxide is preferably used when decomposing the polymer (7) under a basic condition. The polymer (7) can be decomposed in either of a homogeneous system and a heterogeneous system. For example, the silsesquioxane part of the polymer (7) can be decomposed in a homogeneous mixed system of an organic solvent (tetrahydrofuran, acetonitrile and the like) which can dissolve the polymer (7) and hydrofluoric acid. The silsesquioxane part can be decomposed as well in a heterogeneous mixed system of toluene and hydrofluoric acid. In this case, a phase transfer catalyst is preferably used in combination. The examples of the phase transfer catalyst are benzyltrimethylammonium chloride, tetramethylammonium chloride, tetrabutylammonium bromide, trioctylammonium chloride, dioctyldimethylammonium chloride, triethylamine and dimethylaniline. When using potassium hydroxide, decomposition can be carried out as well in a mixed solvent of tetrahydrofuran, ethanol and water.

The addition polymer cut off by the above methods is measured by GPC, whereby a molecular weight of an addition polymer part in the polymer (7) can be determined. It is possible as well to determine a molecular weight of the polymer (7) by using a universal calibration curve obtained from the viscosity and the GPC data. An absolute molecular weight of the polymer (7) can be determined as well by an end group determination method, a membrane osmotic pressure method, a ultracentrifugal method and a light scattering method.

A preferred molecular weight of the polymer (7) falls in a range of 500 to 1,000,000 for a number average molecular weight in terms of polystyrene. The more preferred range is 1,000 to 100,000. However, the upper limit value and the lower limit value in this range do not necessarily have a specific meaning. The molecular weight distribution falls preferably in a range of 1.01 to 2.0 in terms of a polydispersity (Mw/Mn).

The molecular weight of the polymer (7) can be controlled by a proportion of the addition-polymerizable monomer to the compound (6) which is an initiator. That is, a theoretical molecular weight of the graft chain in the polymer (7) can be predicted from a mole ratio of the addition-polymerizable monomer/the compound (6) and a consumption rate of the monomer using the following calculation equation:

$$Mn = (\text{conversion rate(mole \%) of monomer}/100) \times MW_M \times \text{mole ratio} + MW_I$$

In the above calculation equation, Mn is a theoretical number average molecular weight; $MW_M$ is a molecular weight of the addition-polymerizable monomer; $MW_I$ is a molecular weight of the compound (6); and the mole ratio is a mole ratio of the addition-polymerizable monomer to the compound (6).

When intending to obtain a polymer having the number average molecular weight range described above, a mole ratio of the addition-polymerizable monomer to the compound (6) is controlled to about 2 to about 40,000. The preferred range of the above mole ratio is about 10 to about 5,000. The number average molecular weight can be controlled as well by changing the polymerization time.

Any method of GPC, $^1$H-NMR and gas chromatography can be adopted for determining a consumption rate (hereinafter referred to as "conversion") of the monomer.

EXAMPLES

The present invention shall more specifically be explained with reference to examples, but the present invention shall not be restricted to the following examples.

The data of molecular weights in Examples 1 to 100 are polystyrene-standard values determined by GPC (gel permeation chromatography), and the data of molecular weights in Examples 101 to 130 are poly(methyl methacrylate)-standard values determined by GPC. The measuring conditions of GPC are shown below.

Apparatus: JASCO GULLIVER 1500 (intelligent differential refractometer RI-1530), manufactured by JASCO Corp.

Solvent: tetrahydrofuran

Flow velocity: 1 ml/minute

Column temperature: 40° C.

Columns used: Examples 1 to 90: TSKguardcolumn HXL-L (GUARDCOLUMN)+TSKgel G1000HxL (exclusion limited of molecular weight (polystyrene): 1,000)+TSKgel G2000HxL (excluded critical molecular weight (polystyrene): 10,000), each manufactured by Tosoh Co., Ltd.

Standard sample for calibration curve: Polymer Standards (PL), Polystyrene, manufactured by Polymer Laboratories Co., Ltd.

Columns used: Examples 91 to 130: Shodex KF-G (GUARDCOLUMN)+Shodex KF-804L (exclusion limited of molecular weight (polystyrene): 400,000)×2, columns each manufactured by Showa Denko K. K.

Codes used in the examples mean the following.

Ph: phenyl

Ch: cyclohexyl

Cp: cyclopentyl

Et: ethyl iBu: isobutyl iOc: isooctyl

TFPr: trifluoropropyl

TDFOc: tridecafluoro-1,1,2,2-tetrahydrooctyl

TMS: trimethylsilyl

Mn: number average molecular weight

Mw: weight average molecular weight

Example 1

Synthesis of Polyphenylsilsesquioxane (Compound A)

A four neck separable flask having a content volume of 2 liter equipped with stirrer, a reflux condenser, a thermometer and a dropping funnel was charged with ice and water (640.7 g) and toluene (200 g), and the inside of the flask was cooled to 0° C. while stirring. Next, a mixed solution of phenyltrichlorosilane (211.5 g) and toluene (130 g) dried on molecular sieves for a whole day and nigh was dropwise added thereto in one hour so that a temperature of the inside of the flask did not exceed 2° C. Then, after stirring at a room temperature for 30 minutes, the solution was washed with refined water, and toluene was distilled off under reduced pressure to obtain a solid compound A (120.7 g). The compound A had a weight average molecular weight of about 3100.

Example 2

Synthesis of Sodium-Bonded Phenylsilsesquioxane Compound (Compound B)

A four neck flask of 500 ml equipped with a reflux condenser and a thermometer was charged with the compound A (12.9 g) obtained above, tetrahydrofuran (250 ml) dried on molecular sieves for a whole day and night and sodium hydroxide (4.0 g), and the flask was heated at 67° C. while stirring by means of a magnetic stirrer to maintain a reflux state. After about 4 hours, the solution began to get cloudy by deposition of fine powder, and refluxing was continued for one hour as it was to finish the reaction. A solid matter deposited was washed with tetrahydrofuran and separated from tetrahydrofuran by filtering, and then it was dried under vacuum to obtain a compound B (10.1 g).

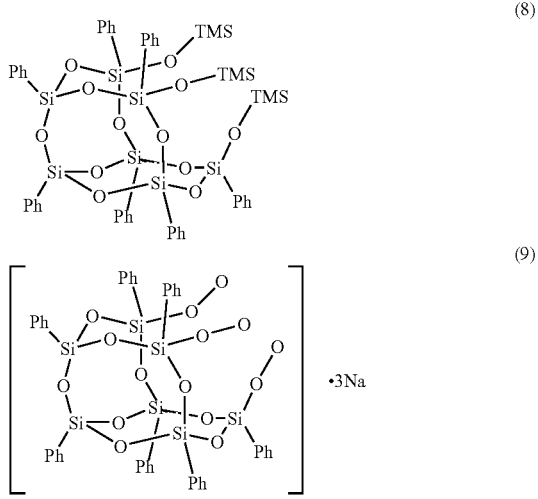

Example 3

Synthesis of Sodium-Bonded Phenylsilsesquioxane Compound (Compound B) Using Phenyltrimethoxysilane as a Raw Material A four neck flask having a content volume of one liter equipped with a reflux condenser, a thermometer and a dropping funnel was charged with phenyltrimethoxyosilane (99 g), sodium hydroxide (10 g) and 2-propanol (500 ml), and a rotator was put thereinto. Deionized water 11 g was dropwise added thereto from the dropping funnel in about 2 minutes while stirring at a room temperature by means of a magnetic stirrer, and then the flask was heated on an oil bath up to a temperature at which 2-propanol was refluxed. After refluxing was started, stirring was continued for 1.5 hour to complete the reaction. Then, the flask was pulled up from the oil bath and left standing still a night at a room temperature to completely deposit a solid matter produced. The solid matter deposited was filtrated by means of a pressure filter equipped with a membrane filter having a pore diameter of 0.1 μm. Then, the solid matter thus obtained was washed once with 2-propanol and dried at 70° C. for 4 hours in a vacuum dryer to obtain a compound B (66 g) of a white solid matter.

Example 4

Introduction of Trimethylsilyl Group into Compound B Obtained Using Phenyltrimethoxysilane as a Raw Material (Compound C)

A four neck flask having a content volume of 50 ml equipped with a dropping funnel, a reflux condenser and a thermometer was charged with a rotator, the compound B (1.2 g) obtained in Example 3, tetrahydrofuran (12 g) and triethylamine (1.8 g), and the flask was sealed with dry nitrogen. Chlorotrimethylosilane (2.3 g) was dropwise added thereto from the dropping funnel at a room temperature in about one minute while stirring by means of a magnetic stirrer. After finishing dropwise adding, stirring was continued at a room temperature for 3 hours to complete the reaction. Then, 10 g of purified water was added thereto to dissolve sodium chloride produced and hydrolyze unreacted chlorotrimethylsilane. The reaction mixture thus obtained was transferred to a separating funnel and separated into an organic phase and an aqueous phase, and the resulting organic phase was repeatedly washed with deionized water until a washing liquid became neutral. The organic phase thus obtained was dried on anhydrous magnesium sulfate, filtered and concentrated under reduced pressure by means of a rotary evaporator to obtain a compound C (1.2 g) of a white solid matter.

The compound C was subjected to structural analysis by means of $^1$H-NMR, $^{13}$C-NMR, $^{29}$Si-NMR, mass spectrometry, X ray crystal structure analysis and IR analysis. It was confirmed from a $^1$H-NMR chart and a $^{13}$C-NMR chart that a phenyl group and a trimethylsilyl group were present in an integral ratio of 7:3. It was confirmed from $^{29}$Si-NMR that three kinds of peaks of 11.547 ppm indicating a trimethylsilyl group, −77.574 ppm, −78.137 ppm and −78.424 ppm (all based on tetramethylsilane) having a phenyl group and indicating a T structure were present in a ratio of 1:3:3. It was confirmed from the measuring results of a mass spectrometric spectrum that the absolute molecular weight was consistent with a theoretical molecular weight of the structure represented by Formula (8) described above. It was confirmed from the measuring results of crystal structure analysis by X ray crystal structure analysis that the compound was the structural body represented by Formula (8) described above. Confirmed from the measuring results of an IR analytical spectrum were absorptions assigned respectively to deformation vibration of Si-Ph in 1430 and 1590 $cm^{-1}$, harmonic vibration of a substituted benzene ring in 1960 to 1760 $cm^{-1}$, stretching vibration of Si—O—Si in 1200 to 950 $cm^{-1}$ and vibration of Si—CH$_3$ in 1250 $cm^{-1}$. These results support that the compound (compound C) replaced by a trimethylsilyl group has the structure represented by Formula (8) described above, and this has made it apparent that the sodium-containing silsesquioxane compound (compound B) obtained has the structure represented by Formula (9) described above. The T structure means a structure in which three oxygen atoms are bonded to an Si atom.

Example 5

Synthesis of Sodium-Bonded Cyclohexylsilsesquioxane Compound Using Cyclohexyltrimethoxysilane as a Raw Material The same operation as in Example 3 is carried out, except that cyclohexyltrimethoxysilane is substituted for phenyltrimethoxyosilane, whereby a sodium-bonded cyclohexylsilsesquioxane compound represented by Formula (10) can be obtained.

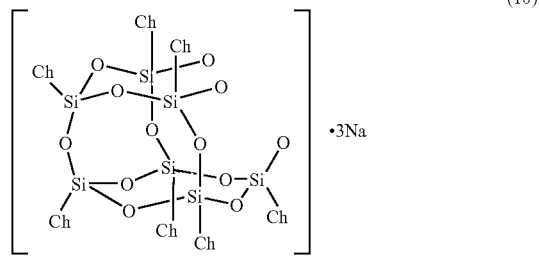

(10)

Example 6

Introduction of Trimethylsilyl Group into Compound (10)

The same operation as in Example 4 is carried out, except that the compound (10) is substituted for the compound (9), whereby a cyclohexylsilsesquioxane compound having a trimethylsilyl group represented by Formula (11) can be obtained. Further, it can be confirmed by subjecting the compound (11) to structural analysis by the same operation as in Example 4 that the compound (10) described above is produced.

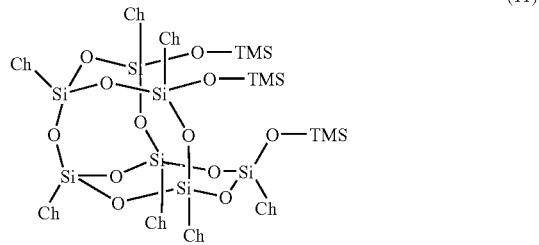

(11)

Example 7

Synthesis of Sodium-Bonded Cyclopentylsilsesquioxane Compound Using Cyclopentyltrimethoxysilane as a Raw Material A four neck flask having a content volume of 200 ml equipped with a reflux condenser, a thermometer and a dropping funnel was charged with cyclopentyltrimethoxyosilane (19.0 g), THF (100 ml), sodium hydroxide (1.7 g) and deionized water (2.3 g), and the flask was heated while stirring by means of a magnetic stirrer. After refluxing was started at 67° C., stirring was continued for 10 hours to finish the reaction. Then, the flask was pulled up from the oil bath and left standing still a night at a room temperature to completely deposit a solid matter produced. The solid matter deposited was filtrated and dried under vacuum to obtain a compound of a powder-like solid matter (4.2 g).

Example 8

Introduction of Trimethylsilyl Group

A four neck flask having a content volume of 100 ml equipped with a reflux condenser was charged with the compound (1.0 g) obtained in Example 7, THF (30 ml), triethylamine (0.5 g) and trimethylchlorosilane (0.7 g), and the mixture was stirred at a room temperature for 2 hours while stirring by means of a magnetic stirrer. After finishing the reaction, the same treatment as in confirming the structure in Example 4 was carried out to obtain a compound of a powder-like solid matter (0.9 g).

The compound thus obtained was analyzed by means of $^1$H-NMR, $^{29}$Si-NMR and X ray crystal structure analysis. It was confirmed from $^1$H-NMR that a cyclopentyl group and a trimethylsilyl group were present in an integral ratio of 7:3. Confirmed from $^{29}$Si-NMR were 8.43 ppm indicating a trimethylsilyl group and three kinds of peaks of −66.37 ppm, −67.97 ppm and −67.99 ppm having a cyclopentyl group and indicating a T structure. A ratio of the sum of the peak intensities of −67.97 ppm and −67.99 ppm to a peak intensity of −66.37 ppm was 6:1. It was confirmed from these results and the crystal structure obtained by the X ray crystal structure analysis that the compound of a powder-like solid matter which was the object of the analysis was a silicon compound represented by Formula (12). Accordingly, it was indicated that the compound obtained in Example 7 had a structure represented by Formula (13).

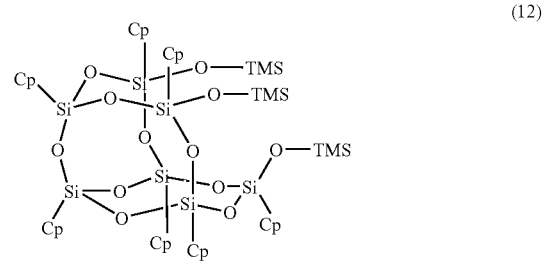

(12)

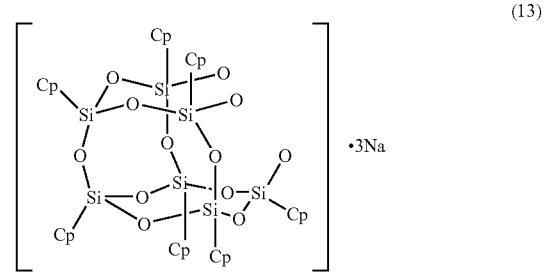

(13)

Example 9

Synthesis of Sodium-Bonded Ethylsilsesquioxane Compound Using Ethyltrimethoxysilane as Raw Material The same operation as in Example 3 is carried out, except that ethyltrimethoxysilane is substituted for phenyltrimethoxyosilane, whereby a sodium-bonded ethylsilsesquioxane compound represented by Formula (14) can be obtained.

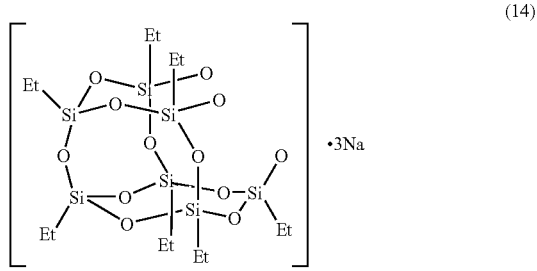

(14)

Example 10

Introduction of Trimethylsilyl Group into Compound (14)

The same operation as in Example 4 is carried out, except that the compound (14) is substituted for the compound (9), whereby an ethylsilsesquioxane compound having a trimethylsilyl group represented by Formula (15) can be obtained. Further, it can be confirmed by subjecting the compound (15) to structural analysis by the same operation as in Example 4 that the compound (14) described above is produced.

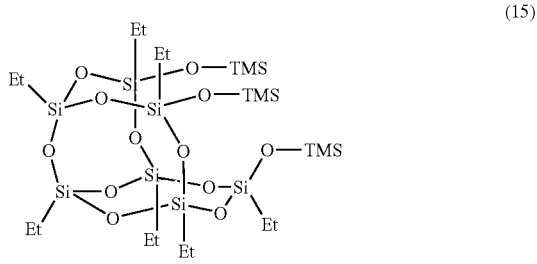

(15)

Example 11

Synthesis of Sodium-Bonded Isobutylsilsesquioxane Compound Using Isobutyltrimethoxysilane as a Raw Material A four neck flask having a content volume of 200 ml equipped with a reflux condenser, a thermometer and a dropping funnel was charged with isobutyltrimethoxysilane (18.7 g), THF (100 ml), sodium hydroxide (1.8 g) and deionized water (2.4 g), and the flask was heated while stirring by means of a magnetic stirrer. After refluxing was started at 67° C., stirring was continued for 10 hours to finish the reaction. The reaction liquid was concentrated under constant pressure until a solid matter was deposited, and then the resulting concentrate was left standing still a night at a room temperature to completely deposit the solid matter. This was filtered and dried under vacuum to obtain a compound of a powder-like solid matter (5.1 g).

Example 12

Introduction of Trimethylsilyl Group

A four neck flask having a content volume of 200 ml equipped with a reflux condenser was charged with the compound of a powder-like solid matter (1.0 g) obtained in Example 11, THF (20 ml), triethylamine (0.5 g) and trimethylchlorosilane (0.8 g), and the mixture was stirred at a room temperature for 2 hours while stirring by means of a magnetic stirrer. After finishing the reaction, the same treatment as in confirming the structure in Example 4 was carried out to obtain a compound of a powder-like solid matter (0.9 g).

The powder-like solid matter described above was subjected to structural analysis by means of $^1$H-NMR and $^{29}$Si-NMR. It was confirmed from a $^1$H-NMR chart that an isobutyl group and a trimethylsilyl group were present in an integral ratio of 7:3. It was confirmed from $^{29}$Si-NMR that three kinds of peaks of 8.72 ppm indicating a trimethylsilyl group, −67.38 ppm, −68.01 ppm and −68.37 ppm having an isobutyl group and indicating a T structure were present in a ratio of 1:3:3. It was confirmed from these results that the compound of a powder-like solid matter which was the object of the analysis was a silicon compound represented by Formula (16). Accordingly, it was indicated that the compound obtained in Example 11 had a structure represented by Formula (17).

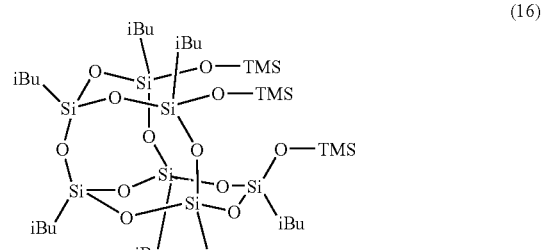

(16)

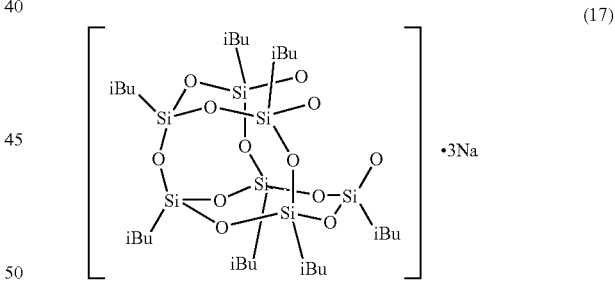

(17)

Example 13

Synthesis of Sodium-Bonded Isooctylsilsesquioxane Compound Using Isooctyltrimethoxysilane as a Raw Material The same operation as in Example 3 is carried out, except that isooctyltrimethoxysilane is substituted for phenyltrimethoxyosilane, whereby a sodium-bonded isooctylsilsesquioxane compound represented by Formula (18) can be obtained.

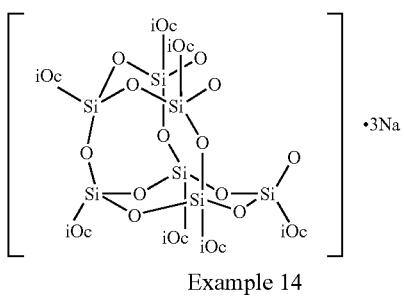

Example 14

Introduction of Trimethylsilyl Group into Compound (18)

The same operation as in Example 4 is carried out, except that the compound (18) is substituted for the compound (9), whereby an isooctylsilsesquioxane compound having a trimethylsilyl group represented by Formula (19) can be obtained. Further, it can be confirmed by subjecting the compound (19) to structural analysis by the same operation as in Example 4 that the compound (18) described above is produced.

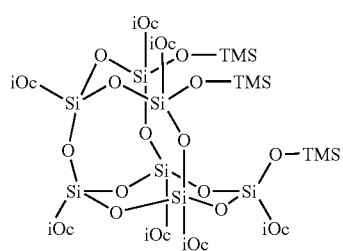

Example 15

Synthesis of Sodium-Added Trifluoropropylsilsesquioxane Compound Using Trifluoropropyltrimethoxysilane as a Raw Material A four neck flask having a content volume of 1 liter equipped with a reflux condenser, a thermometer and a dropping funnel was charged with trifluoropropyltrimethoxyosilane (100 g), THF (500 ml), deionized water (10.5 g) and sodium hydroxide (7.9 g), and the flask was heated on an oil bath from a room temperature up to a temperature at which THF was refluxed while stirring by means of a magnetic stirrer. After refluxing was started, stirring was continued for 5 hours to complete the reaction. Thereafter, the flask was pulled up from the oil bath and left standing still a night at a room temperature, and then the flask was set again on the oil bath to heat and concentrate the reaction liquid under constant pressure until a solid matter was deposited. The product deposited was filtrated through a pressure filter equipped with a membrane filter having a pore diameter of 0.5 μm. Then, the solid matter thus obtained was washed once with THF and dried at 80° C. for 3 hours in a vacuum dryer to obtain 74 g of a colorless powder-like solid matter.

Example 16

Introduction of Trimethylsilyl Group

A four neck flask having a content volume of 50 ml equipped with a dropping funnel, a reflux condenser and a thermometer was charged with the colorless powder-like solid matter (1.0 g) obtained in Example 15, THF (10 g) and triethylamine (1.0 g), and the flask was sealed with dry nitrogen. Chlorotrimethylsilane (3.3 g) was dropwise added thereto at a room temperature in about one minute while stirring by means of a magnetic stirrer. After finishing dropwise adding, stirring was continued at a room temperature for 3 hours to complete the reaction. Then, 10 g of purified water was added thereto to dissolve sodium chloride produced and hydrolyze unreacted chlorotrimethylsilane. The reaction mixture thus obtained was transferred to a separating funnel and separated into an organic phase and an aqueous phase, and the resulting organic phase was repeatedly washed with deionized water until a washing liquid became neutral. The organic phase thus obtained was dried on anhydrous magnesium sulfate, filtered and concentrated under reduced pressure by means of a rotary evaporator to obtain a compound (0.9 g) of a white solid matter.

The white power-like solid matter obtained was subjected to structural analysis by means of GPC, $^1$H-NMR, $^{29}$Si-NMR and $^{13}$C-NMR. It was confirmed from a GPC chart that the white power-like solid matter showed a monodispersibility and had a weight average molecular weight of 1570 in terms of polystyrene and a purity of 98% by weight. It was confirmed from a $^1$H-NMR chart that a trifluoropropyl group and a trimethylsilyl group were present in an integral ratio of 7:3. It was confirmed from a $^{29}$Si-NMR chart that three peaks having a trifluoropropyl group and indicating a T structure were present in a ratio of 1:3:3 and that one peak indicating a trimethylsilyl group was present in 12.11 ppm. It was confirmed from a $^{13}$C-NMR chart that peaks indicating a trifluoropropyl group were present in 131 to 123 ppm, 28 to 27 ppm and 6 to 5 ppm and that a peak indicating a trimethylsilyl group was present in 1.4 ppm. It was confirmed from the measuring results of a mass spectrometric spectrum that the absolute molecular weight was consistent with a theoretical molecular weight of a structural body represented by Formula (20). It was confirmed from the results of crystal structure analysis by X ray crystal structure analysis that the compound was the structural body represented by Formula (20). The above results show that the colorless powder-like solid matter which is an object for the structural analysis has the structure represented by Formula (20). Accordingly, it is judged that the compound before trimethylsilylated has a structure represented by Formula (21).

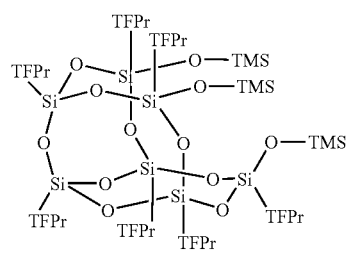

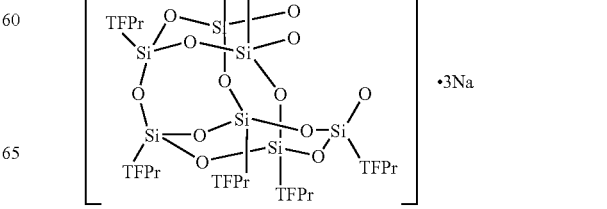

Example 17

Synthesis of Acetoxyethyl-Heptaphenyloctasilsesquioxane Using the Compound (9) as a Raw Material The compound (9) 10 g obtained in Example 1 and tetrahydrofuran (200 ml) were introduced into a four neck flask of 500 ml equipped with a reflux condenser, a thermometer and a rotator. Then, acetoxyethyltrichlorosilane (3.3 g, 1.5 equivalent based on the compound (9)) was quickly added to a compound (9)/tetrahydrofuran solution, and the solution was stirred at a room temperature for 2 hours. Then, the reaction liquid was poured into hexane (1000 g). A solid component deposited was recovered by suction filtration and dissolved again in toluene (90 g), and then the organic layer was washed with water (330 ml). After washing was carried out three times, the organic layer was separated and dried on anhydrous magnesium sulfate (5 g). Thereafter, solid-liquid separation was carried out by filtration through a filter. Then, ethanol (90 g) was added to a solid component obtained by concentrating the organic layer, and the mixture was stirred under a room temperature condition. Further, solid-liquid separation was carried out by means of a pressure filtering device, and a solid component obtained was then dried (80° C., 3 hours) under reduced pressure to obtain a colorless solid matter (6.88 g, yield: 65.9%).

As a result of carrying out GPC measurement of the compound obtained, a single peak was confirmed, and the presence of impurities was not confirmed. It was found from the results of IR, $^1$H-NMR, $^{13}$C-NMR and $^{29}$Si-NMR each shown below that the colorless solid matter obtained had a structure represented by Formula (22).

IR (KBr method: ν=1740 (C=O), 1430 (Si-Ph), 1240 (C—O), 1135 to 1090 (Si-Ph), 1090 to 1000 (Si—O—Si) cm$^{-1}$ $^1$H NMR (400 MHz, TMS standard: δ=0.0 ppm): 7.82 to 7.72, 7.46 to 7.31 (m, 35H, Ph-Si), 4.32 to 4.28 (t, 2H, —O—CH$_2$—), 1.84 (s, 3H, CH$_3$—(C=O)—), 1.37 to 1.33 (t, 2H, —CH$_2$—Si)

$^{13}$C NMR (100 MHz, TMS standard: δ=0.0 ppm): 171.15 (C=O), 134.4 to 134.3, 131.1 to 131.0, 130.2, 128.12 (Ph-Si), 60.6 (—O—CH$_2$—), 20.8 (CH$_3$—(C=O)—), 13.2 (—CH$_2$—Si)

$^{29}$Si NMR (79 MHz, TMS standard: δ=0.0 ppm): −67.97 (—CH$_2$—SiO$_{1.5}$), −78.36, −78.67 (Ph-SiO$_{1.5}$)

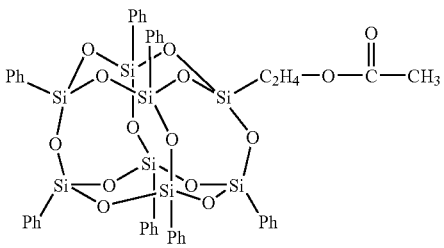

(22)

Example 18

Synthesis of Acetoxyethyl-Heptacyclohexyloctasilsesquioxane Using the Compound (10) as a Raw Material The same operation as in Example 17 is carried out, except that the compound (10) obtained in Example 5 is substituted for the compound (9), whereby a compound represented by Formula (23) can be obtained.

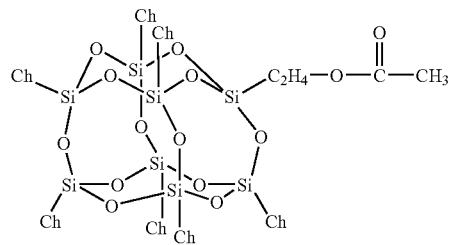

(23)

Example 19

Synthesis of Acetoxyethyl-Heptacyclopentyloctasilsesquioxane Using the Compound (13) as a Raw Material The same operation as in Example 17 is carried out, except that the compound (13) obtained in Example 7 is substituted for the compound (9), whereby a compound represented by Formula (24) can be obtained.

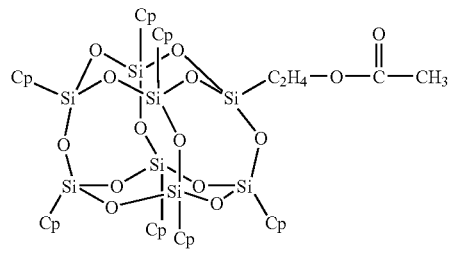

(24)

Example 20

Synthesis of Acetoxyethyl-Heptaethyloctasilsesquioxane Using the Compound (14) as Raw a Material The same operation as in Example 17 is carried out, except that the compound (14) obtained in Example 9 is substituted for the compound (9), whereby a compound represented by Formula (25) can be obtained.

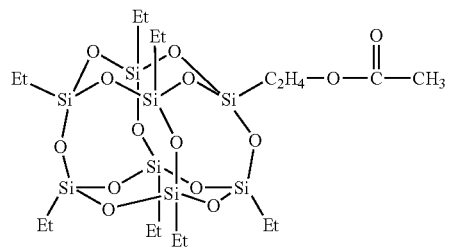

(25)

Example 21

Synthesis of Acetoxyethyl-Heptaisobutyloctasilsesquioxane Using the Compound (17) as a Raw Material The same operation as in Example 17 is carried out, except that the compound (17) obtained in Example 11 is substituted for the compound (9), whereby a compound represented by Formula (26) can be obtained.

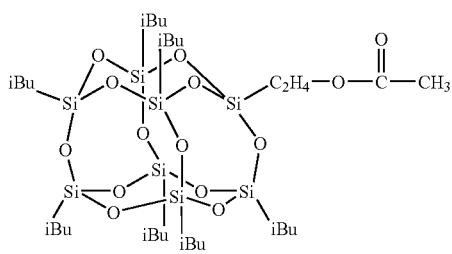 (26)

Example 22

Synthesis of Acetoxyethyl-Heptaisooctyloctasilsesquioxane Using the Compound (18) as a Raw Material The same operation as in Example 17 is carried out, except that the compound (18) obtained in Example 13 is substituted for the compound (9), whereby a compound represented by Formula (27) can be obtained.

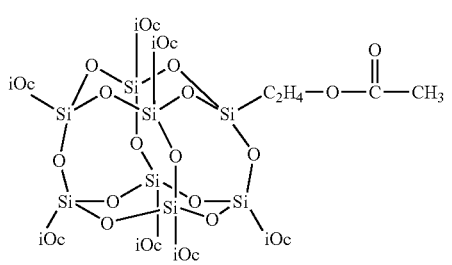 (27)

Example 23

Synthesis of Acetoxyethyl-Heptatrifluoropropyloctasilsesquioxane Using the Compound (21) as a Raw Material The compound (21) 22.71 g obtained in Example 15 and tetrahydrofuran (400 g) were introduced into a four neck flask of 500 ml equipped with a reflux condenser, a thermometer and a rotator. Then, acetoxyethyltrichlorosilane (3.21 g, 1.6 equivalent based on the compound (21)) was quickly added to a compound (21)/tetrahydrofuran solution, and the solution was stirred at a room temperature for 4 hours. Then, after solid-liquid separation was carried out by filtration through a filter, the filtrate was concentrated by means of a rotary evaporator. Methanol (100 ml) was added to the concentrate to carry out solid-liquid separation by filtration through a filter. Further, tetrahydrofuran (200 ml) was added to the solid component thus obtained, and the mixture was dried on anhydrous magnesium sulfate (5 g). Then, solid-liquid separation was carried out by filtration through a filter. Thereafter, methanol (100 g) was added to a solid component obtained by concentrating the organic layer, and the solution was stirred under a room temperature condition. Further, solid-liquid separation was carried out by filtration through a filter, and a solid component obtained was then dried (75° C., 5 hours) under reduced pressure to obtain a colorless solid matter (12.2 g, yield: 51.6%).

As a result of carrying out GPC measurement of the compound obtained, a single peak was confirmed, and the presence of impurities was not confirmed. It was found from the results of $^1$H-NMR, $^{13}$C-NMR and $^{29}$Si-NMR each shown below that the colorless solid matter obtained had a structure represented by Formula (28).

$^1$H NMR (400 MHz, TMS standard: δ=0.0 ppm): 4.18 (t, 2H, —O—CH$_2$—), 2.14 (m, 14H, —[CH$_2$]—CF$_3$), 2.04 (s, 3H, CH$_3$—(C=O)—) 1.19 (t, 2H, —CH$_2$—Si), 0.95 (m, 14H, Si—[CH$_2$]—CH$_2$—CF$_3$)

$^{13}$C NMR (100 MHz, TMS standard: δ=0.0 ppm): 171.11 (C=O), 131.41, 128.68, 125.92, 123.20 (—CF$_3$), 60.01 (—O—CH$_2$—), 28.17, 27.85, 27.55, 27.25 (—[CH$_2$]—CF$_3$), 20.92 (CH$_3$—(C=O)—), 12.81 (—CH$_2$—Si), 4.03 (Si—[CH$_2$]—CH$_2$—CF$_3$)

$^{29}$Si NMR (79 MHz, TMS standard: δ=0.0 ppm): −68.66 (—CH$_2$—SiO$_{1.5}$), −67.62, −67.72 (CF$_3$—CH$_2$—CH$_2$—SiO$_{1.5}$)

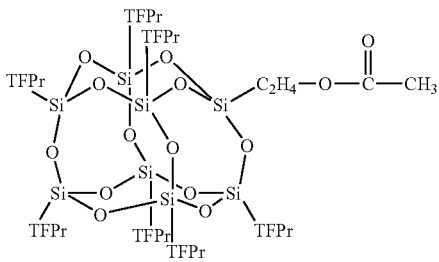 (28)

Example 24

Synthesis of Acetoxyethyl-Heptaphenyloctasilsesquioxane Using the Compound (29) as a Raw Material A compound represented by Formula (29) (10 g, trisilanolphenyl POSS, manufactured by Hybrid Plastics U.S. Co., Ltd.), triethylamine (4.24 g, 1.3 equivalent based on silanol) and tetrahydrofuran (200 ml) were introduced into a four neck flask of 500 ml equipped with a dropping funnel, a reflux condenser, a thermometer and a rotator in an ice bath. Then, acetoxyethyltrichlorosilane (3.32 g, 1.5 equivalent based on the compound (29)) was quickly added to a compound (29)/tetrahydrofuran solution, and the solution was stirred at a room temperature for 2 hours. Then, the reaction liquid was poured into hexane (1000 g). A solid component deposited was recovered by suction filtration and dissolved again in toluene (90 g), and then the organic layer was washed with water (330 ml). After washing was carried out three times, the organic layer was separated and dried on anhydrous magnesium sulfate (5 g). Subsequently, solid-liquid separation was carried out by filtration through a filter. Then, ethanol (90 g) was added to a solid component obtained, and the mixture was stirred under a room temperature condition. Further, solid-liquid separation was carried out by means of a pressure filtering device, and a solid component obtained was then dried (80° C., 3 hours) under reduced pressure to obtain a colorless solid matter (5.25 g, yield: 47.0%).

As a result of carrying out GPC measurement of the compound obtained, a single peak was confirmed, and the presence of impurities was not confirmed. It was found from the results of IR, $^1$H-NMR, $^{13}$C-NMR and $^{29}$Si-NMR each shown below that the colorless solid matter obtained had a structure represented by Formula (22).

IR (KBr method: ν=1740 (C=O), 1430 (Si-Ph), 1240 (C—O), 1135 to 1090 (Si-Ph), 1090 to 1000 (Si—O—Si) cm$^{-1}$ $^1$H NMR (400 MHz, TMS standard: δ=0.0 ppm): 7.82 to 7.72, 7.46 to 7.31 (m, 35H, Ph-Si), 4.32 to 4.28 (t, 2H, —O—CH$_2$—), 1.84 (s, 3H, CH$_3$—(C=O)—), 1.37 to 1.33 (t, 2H, —CH$_2$—Si)

$^{13}$C NMR (100 MHz, TMS standard: δ=0.0 ppm): 171.15 (C=O), 134.4 to 134.3, 131.1 to 131.0, 130.2, 128.12 (Ph-Si), 60.6 (—O—CH$_2$—), 20.8 (CH$_3$—(C=O)—), 13.2 (—CH$_2$—Si)

$^{29}$Si NMR (79 MHz, TMS standard: δ=0.0 ppm): −67.97 (—CH$_2$—SiO$_{1.5}$), −78.36, −78.67 (Ph-SiO$_{1.5}$)

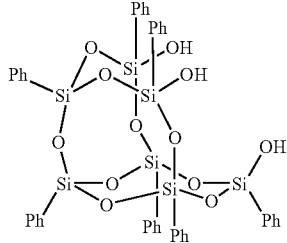

(29)

Example 25

Synthesis of Acetoxyethyl-Heptacyclohexyloctasilsesquioxane Using a Compound (30) as a Raw Material The same operation as in Example 24 is carried out, except that a compound represented by Formula (30) (trisilanolcyclohexyl POSS, manufactured by Hybrid Plastics, U.S. Co., Ltd.) is substituted for the compound (29), whereby the compound (23) described in Example 18 can be obtained.

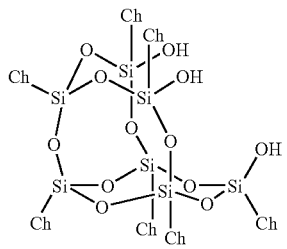

(30)

Example 26

Synthesis of Acetoxyethyl-Heptacyclopentyloctasilsesquioxane Using a Compound (31) as a Raw Material The same operation as in Example 24 is carried out, except that a compound represented by Formula (31) (trisilanolcyclopentyl POSS, manufactured by Hybrid Plastics, U.S. Co., Ltd.) is substituted for the compound (29), whereby the compound (24) described in Example 19 can be obtained.

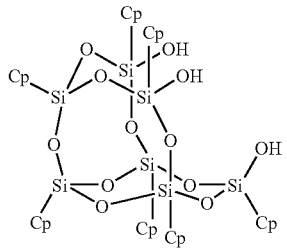

(31)

Example 27

Synthesis of Acetoxyethyl-Heptaethyloctasilsesquioxane Using a Compound (32) as a Raw Material The same operation as in Example 24 is carried out, except that a compound represented by Formula (32) (trisilanolethyl POSS, manufactured by Hybrid Plastics, U.S. Co., Ltd.) is substituted for the compound (29), whereby the compound (25) described in Example 20 can be obtained.

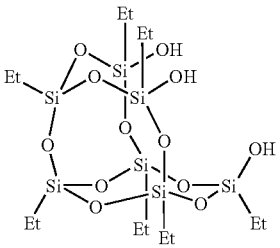

(32)

Example 28

Synthesis of Acetoxyethyl-Heptaisobutyloctasilsesquioxane Using a Compound (33) as a Raw Material The same operation as in Example 24 is carried out, except that a compound represented by Formula (33) (trisilanolisobutyl POSS, manufactured by Hybrid Plastics, U.S. Co., Ltd.) is substituted for the compound (29), whereby the compound (26) described in Example 21 can be obtained.

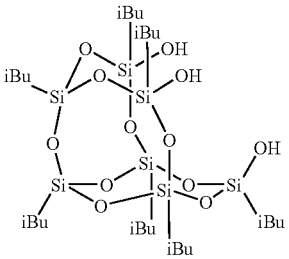

(33)

Example 29

Synthesis of Acetoxyethyl-Heptaisooctyloctasilsesquioxane Using a Compound (34) as a Raw Material The same operation as in Example 24 is carried out, except that a compound represented by Formula (34) (trisilanolisooctyl POSS, manufactured by Hybrid Plastics, U.S. Co., Ltd.) is substituted for the compound (29), whereby the compound (27) described in Example 22 can be obtained.

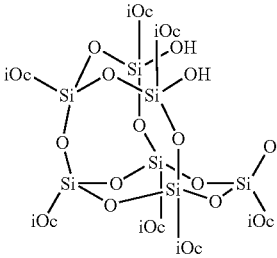

(34)

Example 30

Synthesis of Silanol-Containing Heptatrifluoropropylsilsesquioxane Using the Compound (21) as a Raw Material

A four neck flask of 300 ml equipped with a dropping funnel, a reflux condenser, a thermometer and a rotator was set in an ice bath. The compound (21) 5 g obtained in Example 15 was added to this four neck flask and dissolved in butyl acetate (50 g), and then acetic acid (0.5 g) was dropwise added thereto. The flask was stirred for one hour as it was put in the ice bath. After returned to a room temperature, the reaction liquid was washed (three times) with deionized water (100 ml). The solvent was distilled off by means of a rotary evaporator, and the residue was dried (50° C., one hour) as it was under reduced pressure to obtain a viscous liquid (4.3 g). As a result of carrying out GPC measurement of the compound obtained, a single peak was shown, and the presence of impurities was not confirmed. Further, analysis using IR was carried out to result in confirming absorption (in the vicinity of 3400 cm$^{-1}$) indicating the presence of a silanol group which was not observed in the compound (21). Accordingly, it was indicated that the compound obtained had a structure represented by Formula (35).

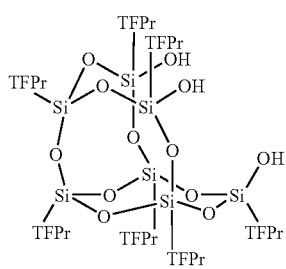

(35)

Acetoxyethyltrichlorosilane is reacted with the compound (35) described above which is a starting raw material under the presence of triethylamine according to the method described in Examples 24 to 29 described above, whereby the compound (28) can be derived.

Example 31

Synthesis of Acetoxyethyl-Heptaphenyloctasilsesquioxane Using the Compound (9) as a Raw Material

The compound (9) 10 g obtained in Example 1, triethylamine (1.5 g) and tetrahydrofuran (200 ml) were introduced into a four neck flask of 500 ml equipped with a reflux condenser, a thermometer and a rotator. Then, acetoxypropyltrichlorosilane (3.5 g, 1.5 equivalent based on the compound (9)) was quickly added to a compound (9)/triethylamine/tetrahydrofuran solution, and the solution was stirred at a room temperature for 2 hours. Then, the reaction liquid was poured into hexane (1000 g). A solid component deposited was recovered by suction filtration and dissolved again in toluene (90 g), and then the organic layer was washed with water (330 ml). After washing was carried out three times, the organic layer was separated and dried on anhydrous magnesium sulfate (5 g). Subsequently, solid-liquid separation was carried out by filtration through a filter. Then, ethanol (90 g) was added to a solid component obtained by concentrating the organic layer, and the mixture was stirred under a room temperature condition. Further, solid-liquid separation was carried out by means of a pressure filtering device, and a solid component obtained was then dried (80° C., 3 hours) under reduced pressure to obtain a colorless solid matter (7.15 g, yield: 67.6%).

As a result of carrying out GPC measurement of the compound obtained, a single peak was confirmed, and the presence of impurities was not confirmed. It was found from the results of IR, $^1$H-NMR, $^{13}$C-NMR and $^{29}$Si-NMR each shown below that the white solid matter obtained had a structure represented by Formula (36).

IR (KBr method: ν=1740 (C=O), 1430 (Si-Ph), 1240 (C—O) 1135 to 1090 (Si-Ph), 1090 to 1000 (Si—O—Si) cm$^{-1}$ $^1$H NMR (400 MHz, TMS standard: δ=0.0 ppm): 7.82 to 7.72, 7.46 to 7.31 (m, 35H, [Ph]-Si), 4.07 to 4.04 (t, 2H, —O—[CH$_2$]—), 1.94 (s, 3H, [CH$_3$]—(C=O)—), 1.84 to 1.88 (tt, 2H, —CH$_2$—[CH$_2$]—CH$_2$—), 1.37 to 1.33 (t, 2H, —[CH$_2$]—Si)

$^{13}$C NMR (100 MHz, TMS standard: δ=0.0 ppm): 171.10 (C=O), 134.4 to 134.3, 131.1 to 131.0, 130.2, 128.12 (Ph-Si), 66.2 (—O—CH$_2$—), 22.2 (—CH$_2$—[CH$_2$]—CH$_2$—), 20.9 ([CH$_3$]—(C=O)—), 8.26 (—[CH$_2$]—Si)

$^{29}$Si NMR (79 MHz, TMS standard: δ=0.0 ppm): −65.30 (—CH$_2$—SiO$_{1.5}$), −78.26, −78.62 (Ph-SiO$_{1.5}$)

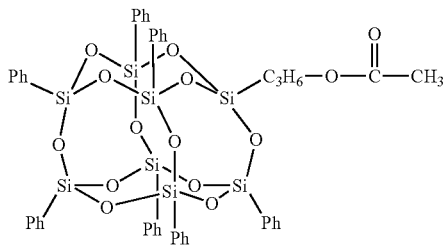

(36)

Example 32

Synthesis of Acetoxypropyl-Heptacyclohexyloctasilsesquioxane Using the Compound (10) as a Raw Material

The same operation as in Example 31 is carried out, except that the compound (10) obtained in Example 5 is substituted for the compound (9), whereby a compound represented by Formula (37) can be obtained.

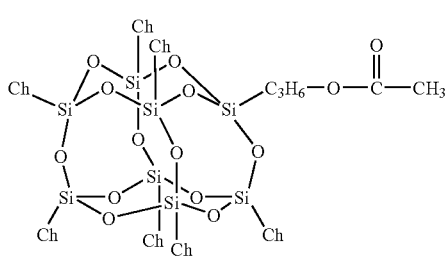

(37)

Example 33

Synthesis of Acetoxypropyl-Heptacyclopentyloctasilsesquioxane Using the Compound (13) as a Raw Material

The same operation as in Example 31 is carried out, except that the compound (13) obtained in Example 7 is substituted for the compound (9), whereby a compound represented by Formula (38) can be obtained.

(38)

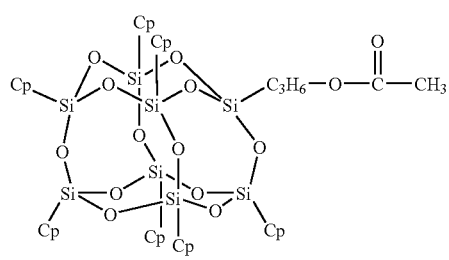

Example 34

Synthesis of Acetoxypropyl-Heptaethyloctasilsesquioxane Using the Compound (14) as a Raw Material The same operation as in Example 31 is carried out, except that the compound (14) obtained in Example 9 is substituted for the compound (9), whereby a compound represented by Formula (39) can be obtained.

(39)

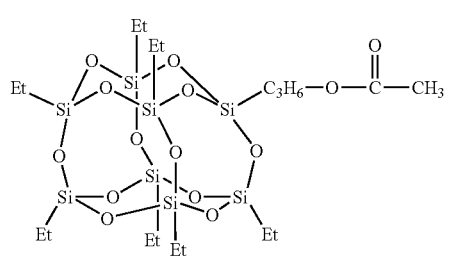

Example 35

Synthesis of Acetoxypropyl-Heptaisobutyloctasilsesquioxane Using the Compound (17) as a Raw Material The same operation as in Example 31 is carried out, except that the compound (17) obtained in Example 11 is substituted for the compound (9), whereby a compound represented by Formula (40) can be obtained.

(40)

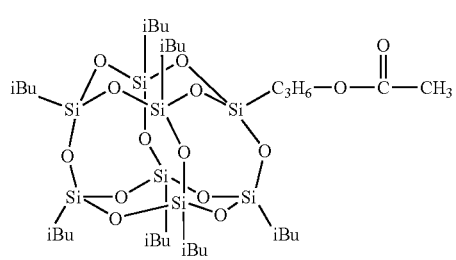

Example 36

Synthesis of Acetoxypropyl-Heptaisooctyloctasilsesquioxane Using the Compound (18) as a Raw Material The same operation as in Example 31 is carried out, except that the compound (18) obtained in Example 13 is substituted for the compound (9), whereby a compound represented by Formula (41) can be obtained.

(41)

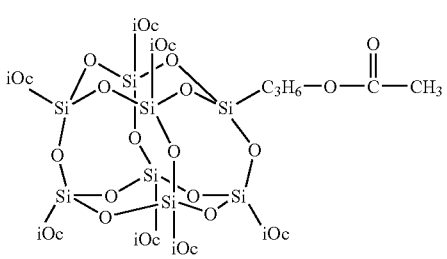

Example 37

Synthesis of Acetoxypropyl-Heptatrifluoropropyloctasilsesquioxane Using the Compound (21) as a Raw Material The same operations as the reaction conditions described in Example 31 and the refining conditions described in Example 23 are carried out, except that the compound (21) obtained in Example 15 is substituted for the compound (9), whereby a compound represented by Formula (42) can be obtained.

(42)

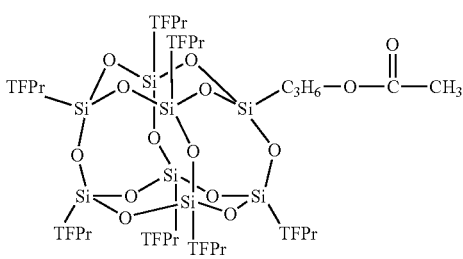

Example 38

Synthesis of Acetoxypropyl-Heptaphenyloctasilsesquioxane Using the Compound (29) as a Raw Material The compound (36) described in Example 31 can be obtained by a method in which acetoxypropyl-trichlorosilane (1.5 equivalent based on the compound (29)) is reacted with the compound (trisilanolphenyl POSS, manufactured by Hybrid Plastics U.S. Co., Ltd.) represented by Formula (29) described in Example 24 used as a raw material in tetrahydrofuran under the presence of triethylamine (1.3 equivalent based on silanol).

Example 39

Synthesis of Acetoxypropyl-Heptacyclohexyloctasilsesquioxane Using the Compound (30) as a Raw Material The same operation as in Example 38 is carried out, except that the compound represented by Formula (30) (trisilanolcyclohexyl POSS, manufactured by Hybrid Plastics, U.S.

Co., Ltd.) is substituted for the compound (29), whereby the compound (37) described in Example 32 can be obtained.

Example 40

Synthesis of Acetoxypropyl-Heptacyclopentyloctasilsesquioxane Using the Compound (31) as a Raw Material The same operation as in Example 38 is carried out, except that the compound represented by Formula (31) (trisilanolcyclopentyl POSS, manufactured by Hybrid Plastics, U.S. Co., Ltd.) is substituted for the compound (29), whereby the compound (38) described in Example 33 can be obtained.

Example 41

Synthesis of Acetoxypropyl-Heptaethyloctasilsesquioxane Using the Compound (32) as Raw Material The same operation as in Example 38 is carried out, except that the compound represented by Formula (32) (trisilanolcycloethyl POSS, manufactured by Hybrid Plastics, U.S. Co., Ltd.) is substituted for the compound (29), whereby the compound (39) described in Example 34 can be obtained.

Example 42

Synthesis of Acetoxypropyl-Heptaisobutyloctasilsesquioxane Using the Compound (33) as Raw Material The same operation as in Example 38 is carried out, except that the compound represented by Formula (33) (trisilanolisobutyl POSS, manufactured by Hybrid Plastics, U.S. Co., Ltd.) is substituted for the compound (29), whereby the compound (40) described in Example 35 can be obtained.

Example 43

Synthesis of Acetoxypropyl-Heptaisooctyloctasilsesquioxane Using the Compound (34) as Raw Material The same operation as in Example 38 is carried out, except that the compound represented by Formula (34) (trisilanolisooctyl POSS, manufactured by Hybrid Plastics, U.S. Co., Ltd.) is substituted for the compound (29), whereby the compound (41) described in Example 36 can be obtained.

Example 44

Synthesis of Acetoxypropyl-Heptatrifluoropropyloctasilsesquioxane Using the Compound (35) as a Raw Material Acetoxyethyltrichlorosilane is reacted under the presence of triethylamine according to the method described in Examples 31 to 43 described above, except that the compound represented by Formula (35) is substituted for the compound (29), whereby the compound (42) described in Example 37 can be obtained.

Example 45

Synthesis of Hydroxyethyl-Heptaphenyloctasilsesquioxane Using the Compound (22) as a Raw Material The compound (22) 2.58 g obtained in Example 17 was introduced into a Kjeldahl flask of 500 ml equipped with a rotator, and a mixed solution (300 ml) of methanol (174.7 ml), chloroform (174.3 ml) and sulfuric acid (36N, 0.7 ml) was introduced thereinto and stirred for 72 hours under a room temperature condition. Then, the solution was concentrated by means of a rotary evaporator, and the concentrate was dissolved again in ethyl acetate (500 ml). Thereafter, the organic layer was washed with water (500 ml) in a separating funnel and dried on anhydrous magnesium sulfate (5 g). Solid-liquid separation was carried out by filtration through a filter, and then the organic layer was concentrated by means of a rotary evaporator and dried to obtain a colorless solid matter (2.37 g, yield: 91.7%). The colorless solid matter (1.09 g) was recrystallized from toluene, and toluene was distilled off under reduced pressure to obtain a colorless solid matter (0.48 g, yield: 43.7%).

As a result of carrying out GPC measurement of the compound obtained, a single peak was confirmed, and the presence of impurities was not confirmed. It was found from the results of IR, $^1$H-NMR, $^{13}$C-NMR and $^{29}$Si-NMR each shown below that the solid matter had a structure represented by Formula (43).

IR (KBr method: ν=3600 to 3200 (OH), 1420 (Si-Ph), 1135 to 1090 (Si-Ph), 1090 to 1000 (Si—O—Si) cm$^{-1}$ $^1$H NMR (400 MHz, TMS standard: δ=0.0 ppm): 7.82 to 7.72, 7.46 to 7.31 (m, 35H, Ph-Si), 3.85 to 3.87 (t, 2H, —CH$_2$—O—), 1.42 to 1.62 (broad, 1H, —OH), 1.26 to 1.31 (t, 2H, Si—CH$_2$—)

$^{13}$C NMR (100 MHz, TMS standard: δ=0.0 ppm): 134.5 to 134.1, 131.1 to 131.0, 130.3, 128.11 to 127.9 (Ph-Si), 58.6 (—CH$_2$—OH), 17.5 (Si—CH$_2$—)

$^{29}$Si NMR (79 MHz, TMS standard: δ=0.0 ppm): −67.31 (—CH$_2$—SiO$_{1.5}$), −78.42, −78.79 (Ph-SiO$_{1.5}$)

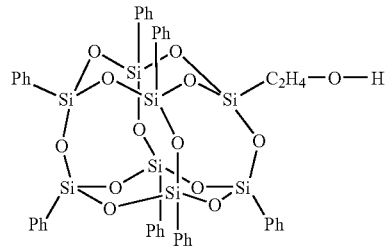

(43)

The compound (22) obtained in Example 24 can be derived as well into the compound (43) by carrying out the same operation as described above.

Example 46

Synthesis of Hydroxyethyl-Heptaphenyloctasilsesquioxane Using the Compound (22) as a Raw Material Reaction was carried out according to Example 45 to obtain a colorless solid matter (0.09 g, yield: 94.7%), except that the conditions were changed to the compound (22) 0.1 g obtained in Example 17, methanol (66.6 ml), chloroform (100 ml) and sulfuric acid (36N, 0.3 ml). It was found from the results of IR, $^1$H-NMR, $^{13}$C-NMR and $^{29}$Si-NMR each shown below that the solid matter obtained had the structure represented by Formula (43).

IR (KBr method: ν=3600 to 3200 (OH), 1420 (Si-Ph), 1135 to 1090 (Si-Ph), 1090 to 1000 (Si—O—Si) cm$^{-1}$ $^1$H NMR (400 MHz, TMS standard: δ=0.0 ppm): 7.82 to 7.72, 7.46 to 7.31 (m, 35H, Ph-Si), 3.85 to 3.87 (t, 2H, —CH$_2$—O—), 1.42 to 1.62 (broad, 1H, —OH), 1.26 to 1.31 (t, 2H, Si—CH$_2$—)

$^{13}$C NMR (100 MHz, TMS standard: δ=0.0 ppm): 134.5 to 134.1, 131.1 to 131.0, 130.3, 128.11 to 127.9 (Ph-Si), 58.6 (—CH$_2$—OH), 17.5 (Si—CH$_2$—)

$^{29}$Si NMR (79 MHz, TMS standard: δ=0.0 ppm): −67.31 (—CH$_2$—SiO$_{1.5}$), −78.42, −78.79 (Ph-SiO$_{1.5}$)

The compound (22) obtained in Example 22 can be derived as well into the compound (43) by carrying out the same operation as described above.

Example 47

Transesterification Reaction of the Compound (22) by a Chloroform/Methanol/Sulfuric Acid Mixed Solvent System Reaction was carried out according to Example 2 to obtain a colorless solid matter (0.064 g, yield: 67.4%), except that the conditions were changed to the compound (22) 0.1 g obtained in Example 17, ethanol (83.3 ml), chloroform (83.3 ml) and sulfuric acid (36N, 0.3 ml). IR measurement was carried out, and as a result thereof, absorption of carbonyl based on the presence of an acetoxy group was observed in 1740 cm$^{-1}$. It was found from the results of 1H-NMR that the solid matter was a mixture (content of the compound (43): 66.3 mol %) of the compound (43) and the compound (22).

Example 48

Transesterification Reaction of the Compound (22) by a Chloroform/Methanol/Sulfuric Acid Mixed Solvent System Reaction was carried out according to Example 2 to obtain a colorless solid matter (0.078 g, yield: 82.1%) except that the conditions were changed to the compound (22) 0.1 g obtained in Example 17, ethanol (66.6 ml), chloroform (100 ml), sulfuric acid (36N, 0.3 ml) and the reaction time: 96 hours. IR measurement was carried out, and as a result thereof, absorption of carbonyl based on the presence of an acetoxy group was observed in 1740 cm$^{-1}$. It was found from the results of $^1$H-NMR that the solid matter was a mixture (content of the compound (43): 90.1 mol %) of the compound (43) and the compound (22).

Example 49

Synthesis of Hydroxyethyl-Heptacyclohexyloctasilsesquioxane Using the Compound (23) as a Raw Material The same operation as in Example 45 is carried out, except that the compound (23) obtained in Example 18 or Example 25 is substituted for the compound (22), whereby a compound represented by Formula (44) can be obtained.

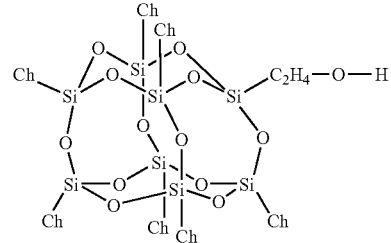

(44)

Example 50

Synthesis of Hydroxyethyl-Heptacyclopentyloctasilsesquioxane Using the Compound (24) as a Raw Material The same operation as in Example 45 is carried out, except that the compound (24) obtained in Example 19 or Example 26 is substituted for the compound (22), whereby a compound represented by Formula (45) can be obtained.

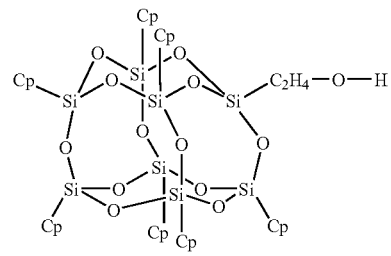

(45)

Example 51

Synthesis of Hydroxyethyl-Heptaethyloctasilsesquioxane Using the Compound (25) as a Raw Material The same operation as in Example 45 is carried out, except that the compound (25) obtained in Example 20 or Example 27 is substituted for the compound (22), whereby a compound represented by Formula (46) can be obtained.

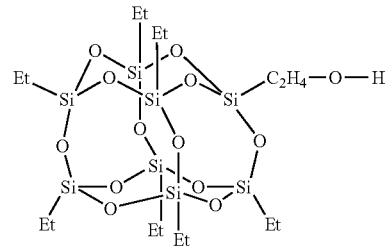

(46)

Example 52

Synthesis of Hydroxyethyl-Heptaisobutyloctasilsesquioxane Using the Compound (26) as a Raw Material The same operation as in Example 45 is carried out, except that the compound (26) obtained in Example 21 or Example 28 is substituted for the compound (22), whereby a compound represented by Formula (47) can be obtained.

(47)

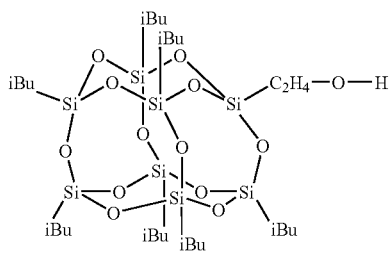

Example 53

Synthesis of Hydroxyethyl-Heptaisooctyloctasilsesquioxane Using the Compound (27) as a Raw Material The same operation as in Example 45 is carried out, except that the compound (27) obtained in Example 27 or Example 29 is substituted for the compound (22), whereby a compound represented by Formula (48) can be obtained.

(48)

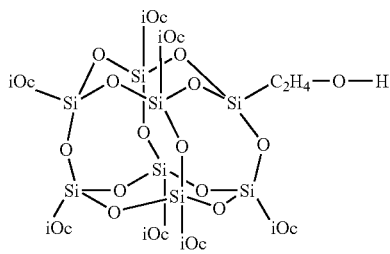

Example 54

Synthesis of Hydroxyethyl-Heptatrifluoropropyloctasilsesquioxane Using the Compound (28) as a Raw Material The compound (28) 3.5 g obtained in Example 23 was introduced into a three neck flask of 1000 ml equipped with a reflux condenser, a thermometer and a rotator, and a mixed solution (600 ml) of methanol (359.5 ml), AK-225 (239.6 ml, HCFC-225: $CF_3CF_2CHCl_2/CClF_2CF_2CHClF$ mixture, manufactured by Asahi Glass Co., Ltd.) and sulfuric acid (36N, 0.7 ml) was introduced thereinto and stirred at a room temperature for 12 hours. Thereafter, the temperature was raised up to 45° C., and the solution was further stirred for 9 hours. Then, the solution was concentrated by means of a rotary evaporator, and the concentrate was dissolved again in AK-225 (200 ml). Thereafter, the organic layer was washed with water (500 ml) in a separating funnel and dried on anhydrous magnesium sulfate (5 g) Solid-liquid separation was carried out by filtration through a filter, and then the organic layer was concentrated by means of a rotary evaporator and dried to obtain a colorless solid matter (3.04 g, yield: 89.9%).

As a result of carrying out GPC measurement of the compound obtained, a single peak was confirmed, and the presence of impurities was not confirmed. It was found from the results of $^1$H-NMR, $^{13}$C-NMR and $^{29}$Si-NMR each shown below that the colorless solid matter obtained had the structure represented by Formula (43).

$^1$H NMR (400 MHz, TMS standard: δ=0.0 ppm): 3.81 (t, 2H, —CH$_2$—O—), 2.14 (m, 14H, —[CH$_2$]—CF$_3$), 1.39 (broad, 1H, —OH), 1.13 (t, 2H, Si—[CH$_2$]—CH$_2$—OH), 0.93 (m, 14H, Si—[CH$_2$]—CH$_2$—CF$_3$)

$^{13}$C NMR (100 MHz, TMS standard: δ=0.0 ppm): 131.31, 128.58, 125.83, 123.11 (—CF$_3$), 58.08 (—CH$_2$—OH), –28.12, 27.83, 27.52, 27.22 (—[CH$_2$]—CF$_3$), 19.74 (—CH$_2$—Si), 4.02 (Si—[CH$_2$]—CH$_2$—CF$_3$)

$^{29}$Si NMR (79 MHz, TMS standard: δ=0.0 ppm): –67.84 (—CH$_2$—SiO$_{1.5}$), –67.65, –67.66, –67.84 (CF$_3$—CH$_2$—CH$_2$—SiO$_{1.5}$)

(49)

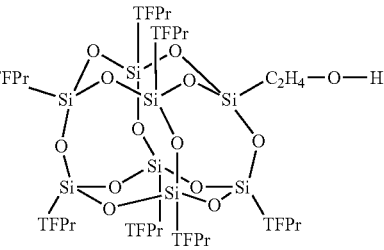

The compound (28) obtained in Example 30 can be derived as well into the compound (49) by carrying out the same operation as described above.

Example 55

Transesterification Reaction of the Compound (28) by a Chloroform/Methanol/Sulfuric Acid Mixed Solvent System Reaction was carried out according to Example 54 to obtain a colorless solid matter (yield: 93.1%), except that the conditions were changed to the compound (28) 0.5 g obtained in Example 23, methanol (42.7 ml), AK-225 (42.7 ml) and sulfuric acid (36N, 0.26 ml). It was found from the results of $^1$H-NMR that the solid matter was a mixture (content of the compound (49): 89.4 mol %) of the compound (49) and the compound (28).

Example 56

Transesterification Reaction of the Compound (28) by a Chloroform/Methanol/Sulfuric Acid Mixed Solvent System Reaction was carried out according to Example 54 to obtain a colorless solid matter (yield: 92.2%), except that the conditions were changed to the compound (28) 0.5 g obtained in Example 23, methanol (42.7 ml), AK-225 (42.7 ml), sulfuric acid (36N, 0.26 ml), a reaction temperature of a room temperature and a reaction time of 72 hours. It was found from the results of $^1$H-NMR that the solid matter was a mixture (content of the compound (49): 91.3 mol %) of the compound (49) and the compound (28).

Example 57

Transesterification Reaction of the Compound (28) by a Chloroform/Methanol/Sulfuric Acid Mixed Solvent System Reaction was carried out according to Example 54 to obtain a colorless solid matter (yield: 91.0%), except that the conditions were changed to the compound (28) 0.5 g obtained in Example 23, methanol (42.7 ml), chloroform (42.7 ml), sulfuric acid (36N, 0.26 ml), a reaction temperature of a room temperature and a reaction time of 72 hours. It was found from the results of $^1$H-NMR that the solid matter was a mixture (content of the compound (49): 81.5 mol %) of the compound (49) and the compound (28).

Example 58

Transesterification Reaction of the Compound (28) by a Chloroform/Methanol/Sulfuric Acid Mixed Solvent System Reaction was carried out according to Example 54 to obtain a colorless solid matter (yield: 90.9%), except that the conditions were changed to the compound (28) 0.5 g obtained in Example 23, methanol (42.7 ml), chloroform (42.7 ml), p-toluenesulfonic acid (4.43 g), a reaction temperature of a room temperature and a reaction time of 72 hours. It was found from the results of $^1$H-NMR that the solid matter was a mixture (content of the compound (49): 89.0 mol %) of the compound (49) and the compound (28).

Example 59

Synthesis of Hydroxypropyl-Heptaphenyloctasilsesquioxane Using the Compound (36) as a Raw Material The compound (36) 2.5 g obtained in Example 31 was introduced into a Kjeldahl flask of 500 ml equipped with a rotator, and a mixed solution (417.4 ml) of methanol (208.3 ml), chloroform (208.3 ml) and sulfuric acid (36N, 0.75 ml) was introduced thereinto and stirred for 72 hours under a room temperature condition. Then, the solution was concentrated by means of a rotary evaporator, and the concentrate was dissolved again in ethyl acetate (500 ml). Thereafter, the organic layer was washed with water (500 ml) in a separating funnel and dried on anhydrous magnesium sulfate (5.0 g). Solid-liquid separation was carried out by filtration through a filter, and then the organic layer was concentrated by means of a rotary evaporator and dried to obtain a colorless solid matter (2.35 g, yield: 97.9%). The colorless solid matter was washed with ethanol to obtain a colorless solid matter (1.26 g, yield: 52.5%) by suction filtration.

As a result of carrying out GPC measurement of the compound, a single peak was confirmed, and the presence of impurities was not confirmed. It was found from the results of IR, $^1$H-NMR, $^{13}$C-NMR and $^{29}$Si-NMR each shown below that the solid matter had a structure represented by Formula (50).

IR (KBr method: ν=3600 to 3200 (OH), 1420 (Si-Ph), 1135 to 1090 (Si-Ph), 1090 to 1000 (Si—O—Si) cm$^{-1}$ $^1$H NMR (400 MHz, TMS standard: δ=0.0 ppm): 7.82 to 7.72, 7.48 to 7.32 (m, 35H, [Ph]-Si), 3.62 to 3.57 (t, 2H, —[CH$_2$]—O—), 1.2 (broad, 1H, —[OH]), 1.78 to 1.74 (tt, 2H, —CH$_2$—[CH$_2$]—CH$_2$—), 0.90 to 0.86 (t, 2H, Si—[CH$_2$]—)

$^{13}$C NMR (100 MHz, TMS standard: δ=0.0 ppm): 134.5 to 134.4, 131.1 to 131.0, 130.6 to 130.4, 128.2 to 128.1 ([Ph]-Si), 65.0 (—[CH$_2$]—OH), 26.1 (—CH$_2$—[CH$_2$]—CH$_2$—), 7.9 (Si—[CH$_2$]—)

$^{29}$Si NMR (79 MHz, TMS standard: δ=0.0 ppm): −65.08 (—CH$_2$—SiO$_{1.5}$), −78.55, −78.94 (Ph-SiO$_{1.5}$)

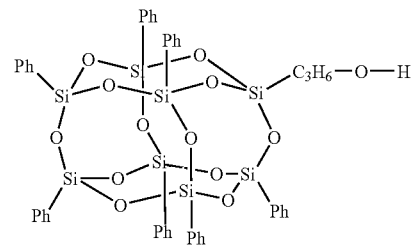

(50)

The compound (36) obtained in Example 38 can be derived as well into the compound (50) by carrying out the same operation as described above.

Example 60

Synthesis of Hydroxypropyl-Heptacyclohexyloctasilsesquioxane Using the Compound (37) as a Raw Material The same operation as in Example 59 is carried out, except that the compound (37) obtained in Example 32 or Example 39 is substituted for the compound (36), whereby a compound represented by Formula (51) can be obtained.

(51)

Example 61

Synthesis of Hydroxypropyl-Heptacyclopentyloctasilsesquioxane Using the Compound (38) as a Raw Material The same operation as in Example 59 is carried out, except that the compound (38) obtained in Example 33 or Example 40 is substituted for the compound (36), whereby a compound represented by Formula (52) can be obtained.

(52)

Example 62

Synthesis of Hydroxypropyl-Heptaethyloctasilsesquioxane Using the Compound (39) as a Raw Material The same operation as in Example 45 is carried out, except that the compound (39) obtained in Example 34 or Example 41 is substituted for the compound (36), whereby a compound represented by Formula (53) can be obtained.

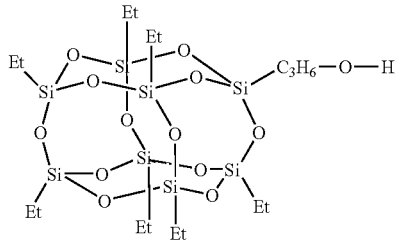

(53)

Example 63

Synthesis of Hydroxypropyl-Heptaisobutyloctasilsesquioxane Using the Compound (40) as a Raw Material The same operation as in Example 45 is carried out, except that the compound (40) obtained in Example 35 or Example 42 is substituted for the compound (36), whereby a compound represented by Formula (54) can be obtained.

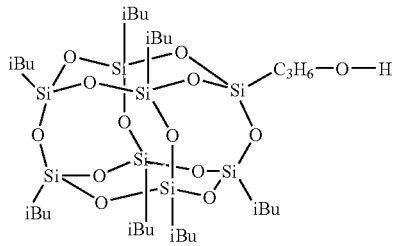

(54)

Example 64

Synthesis of Hydroxyethyl-Heptaisooctyloctasilsesquioxane Using the Compound (41) as a Raw Material The same operation as in Example 45 is carried out, except that the compound (41) obtained in Example 36 or Example 43 is substituted for the compound (36), whereby a compound represented by Formula (55) can be obtained.

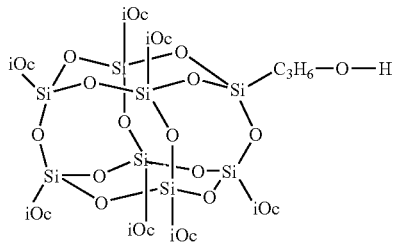

(55)

Example 65

Synthesis of hydroxypropyl-heptatrifluoropropylsilsesquioxane Using the Compound (42) as a Raw Material The same operation as in Example 54 is carried out, except that the compound (42) obtained in Example 37 or Example 44 is substituted for the compound (36), whereby a compound represented by Formula (56) can be obtained.

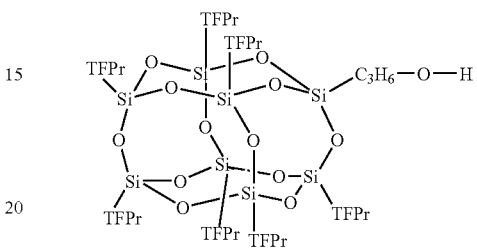

(56)

Example 66

Synthesis of Sodium-Bonded tridecafluoro-1,1,2,2-tetrahydrooctylsilsesquioxane Compound Using tridecafluoro-1,1,2,2-tetrahydrooctyltriethoxysilane as a Raw Material A four neck flask having a content volume of 50 ml equipped with a reflux condenser, a thermometer and a dropping funnel was charged with tridecafluoro-1,1,2,2-tetrahydrooctyltriethoxysilane (4.9 g), THF (15 ml), sodium hydroxide (0.2 g) and ion-exchanged water (0.2 g), and a rotator was put thereinto to heat and reflux the mixture at 75° C. Stirring was continued for 5 hours since refluxing was started to finish the reaction. Then, it was concentrated under constant pressure by heating and dried at 80° C. for 3 hours in a vacuum dryer to obtain 4.0 g of a viscous liquid.

Example 67

Introduction of Trimethylsilyl Group

A three neck flask having a content volume of 50 ml was charged with the viscous liquid (2.6 g) described above, THF (10 g), triethylamine (1.0 g) and trimethylchlorosilane (3.3 g), and the mixture was stirred at a room temperature for 3 hours while stirring by means of a magnetic stirrer. After finishing the reaction, the same treatment as in confirming the structure in Example 16 was carried out to obtain 1.3 g of a viscous liquid.

The compound thus obtained was analyzed by GPC. As a result of carrying out the measurement, it was confirmed that the viscous liquid was monodispersed and that it had a weight average molecular weight of 3650 in terms of polystyrene and a purity of 100%. Synthetically judging from the above results and the results obtained in Examples 3 to 16, it was estimated that the viscous liquid which was the object of the analysis was a silicon compound represented by Formula (57). Accordingly, it is indicated that the compound obtained in Example 66 has a structure represented by Formula (58).

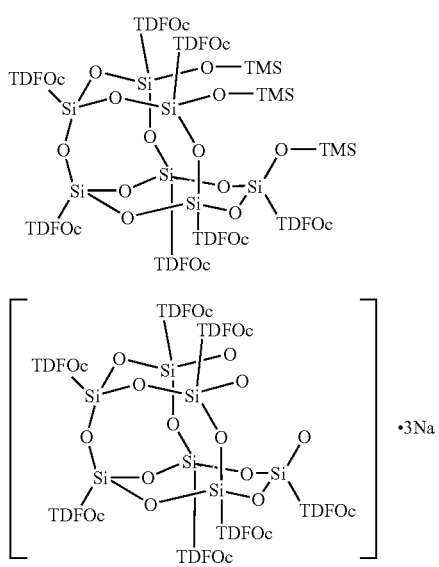

(57)

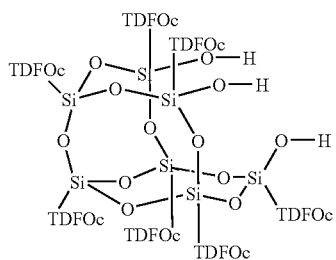

(58)

Example 68

Synthesis of Silanol-Containing tridecafluoro-1,1,2,2-tetrahydrooctylsilsesquioxane Compound Using the Compound (58) as a Raw Material The same operation as in Example 30 is carried out, except that the compound (58) is used as a raw material and that AK-225 is used as the solvent used for the reaction in place of butyl acetate, whereby a compound represented by Formula (59) can be obtained.

(59)

Example 69

Synthesis of acetoxyethyl-heptatridecafluoro-1,1,2,2-tetrahydrooctyloctasilsesquioxane Using the Compound (58) as a Raw Material The same operation as in Example 23 is carried out, except that the compound (58) is used as a raw material and that AK-225 is used as the solvent used for the reaction in place of tetrahydrofuran, whereby a compound represented by Formula (60) can be obtained.

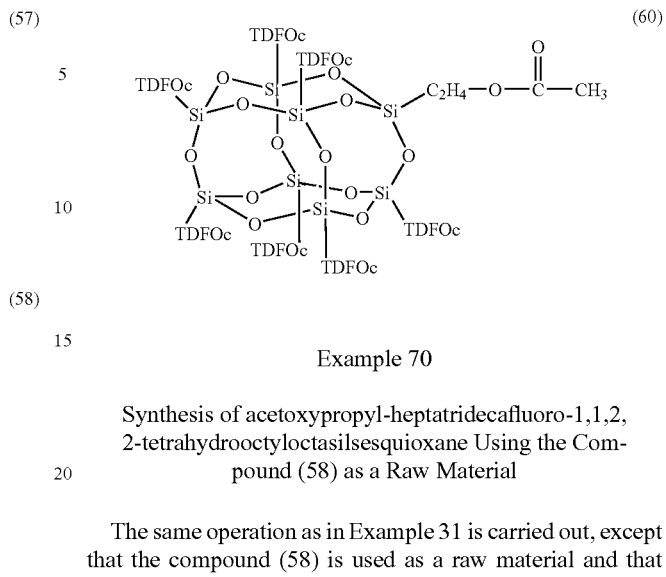

(60)

Example 70

Synthesis of acetoxypropyl-heptatridecafluoro-1,1,2,2-tetrahydrooctyloctasilsesquioxane Using the Compound (58) as a Raw Material The same operation as in Example 31 is carried out, except that the compound (58) is used as a raw material and that AK-225 is used as the solvent used for the reaction in place of tetrahydrofuran, whereby a compound represented by Formula (61) can be obtained.

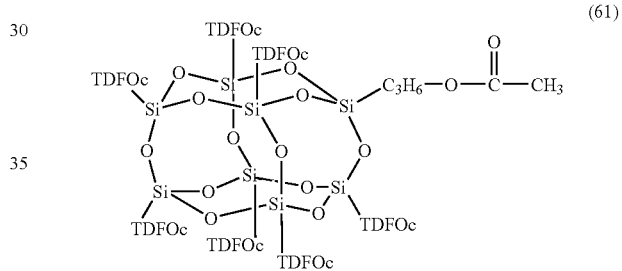

(61)

Example 71

Synthesis of acetoxyethyl-heptatridecafluoro-1,1,2,2-tetrahydrooctyloctasilsesquioxane Using the Compound (59) as a Raw Material Acetoxyethyltrichlorosilane is reacted under the presence of triethylamine according to the method described in Examples 24 to 30, except that the compound (59) is used as a raw material and that the solvent used for the reaction is changed to AK-225, whereby the compound (60) can be derived.

Example 72

Synthesis of acetoxypropyl-heptatridecafluoro-1,1,2,2-tetrahydrooctyloctasilsesquioxane Using the Compound (59) as a Raw Material Acetoxypropyltrichlorosilane is reacted under the presence of triethylamine according to the method described in Examples 38 to 44, except that the compound (59) is used as a raw material and that the solvent used for the reaction is changed to AK-225, whereby the compound (61) can be derived.

Example 73

Synthesis of hydroxyethyl-heptatridecafluoro-1,1,2,2-tetrahydrooctylsilsesquioxane Using the Compound (60) as a Raw Material The same operation as in Examples 54 to 58 is carried out, except that the compound (60) obtained in Example 69 or Example 71 is used, whereby a compound represented by Formula (62) can be obtained.

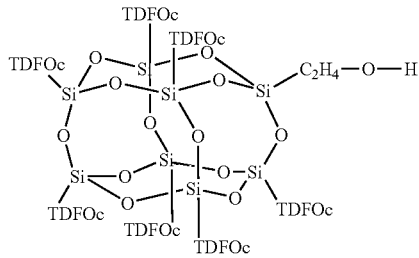

(62)

Example 74

Synthesis of hydroxypropyl-heptamidecafluoro-1,1,2,2-tetrahydrooctyloctasilsesquioxane Using the Compound (61) as a Raw Material The same operation as in Examples 54 to 58 is carried out, except that the compound (61) obtained in Example 70 or Example 72 is used, whereby a compound represented by Formula (63) can be obtained.

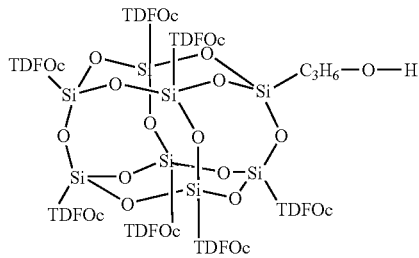

(63)

Example 75

Compound (64): Synthesis of (2-bromo-2-methylpropionyloxyethyl)-heptaphenyloctasilsesquioxane A 25 ml-Kjeldahl flask was charged with the compound (43) (1.21 g), triethylamine (0.12 g) dried on molecular sieves (4 Å) and dry methylene chloride (6.41 g) under argon atmosphere. The compound C was dissolved while stirring at a room temperature by means of a magnetic stirrer, and then the solution was cooled on a dry ice-methanol bath to maintain a solution temperature at −78° C. Then, 2-bromo-2-methylpropionyl bromide (0.3 g, 1.1 equivalent based on the compound (43)) was quickly added to the above solution and stirred at −78° C. for one hour, and then the solution was further stirred at a room temperature for 2 hours. After finishing the reaction, a triethylamine-hydrobromic acid salt was removed by filtration. Methylene chloride (100 ml) was added to the reaction liquid obtained, and it was washed in order once with water (300 ml), twice with a sodium hydrogencarbonate aqueous solution (1%, 300 ml) and twice with water (300 ml) and then dried on anhydrous magnesium sulfate (5 g). Thereafter, the above liquid was concentrated at a room temperature by means of a rotary evaporator to reduce a liquid amount to about 20 ml. Methanol (400 ml) was added to this concentrate (20 ml) to deposit a solid component. Then, it was left standing still in a freezing chamber of −35° C. to sufficiently deposit the solid component, and then solid-liquid separation was carried out by filtration. The solid component thus obtained was dried (40° C., 6 hours) under reduced pressure to obtain a white solid matter (1.13 g, yield: 81.4%).

As a result of carrying out GPC measurement of the compound obtained, a single peak was confirmed, and the presence of impurities was not confirmed. It was confirmed from the measuring result of the mass analytical spectrum that the absolute molecular weight was consistent with a theoretical molecular weight of a structure represented by Formula (64). It was found from the results of IR, $^1$H-NMR, $^{13}$C-NMR and $^{29}$Si-NMR each shown below that the white solid matter obtained had a structure represented by Formula (64).

IR (KBr method: ν=1740 (C=O), 1430 (Si-Ph), 1270 (C—O) 1135 to 1090 (Si-Ph), 1090 to 1000 (Si—O—Si) cm$^{-1}$.

$^1$H NMR (400 MHz, TMS standard: δ=0.0 ppm): 7.82 to 7.72, 7.46 to 7.31 (m, 35H, Ph-Si), 4.41 to 4.37 (t, 2H, —O—CH$_2$—), 1.79 (s, 6H, —C(Br)(CH$_3$)$_2$), 1.43 to 1.39 (t, 2H, —CH$_2$—Si).

$^{13}$C NMR (100 MHz, TMS standard: δ=0.0 ppm): 171.7 (C=O), 134.3, 131.1 to 131.1, 131.2 to 130.1, 128.1 to 128.0 (Ph-Si), 62.5 (—CH$_2$—O—), 55.8 (—C(Br)), 30.6 ((—CH$_3$)$_2$), 12.9 (Si—CH$_2$—).

$^{29}$Si NMR (79 MHz, TMS standard: δ=0.0 ppm): −68.27 (—CH$_2$—SiO$_{1.5}$), −78.4, −78.7 (Ph-SiO$_{1.5}$).

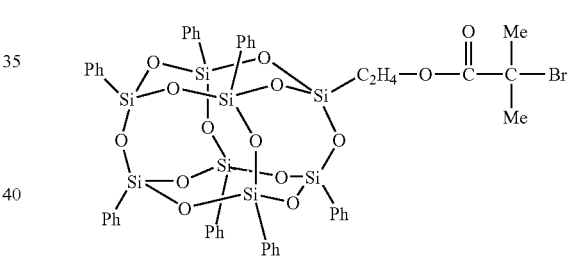

(64)

Example 76

Compound (65): Synthesis of (2-bromo-2-methylpropionyloxyethyl)-heptacyclohexyloctasilsesquioxane The same operation as in Example 75 is carried out, except that the compound (44) obtained in Example 49 is substituted for the compound (43), whereby a compound represented by Formula (65) can be obtained.

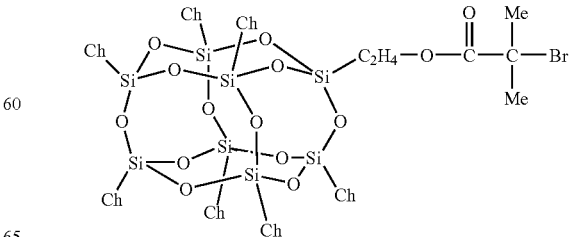

(65)

Example 77

Compound (66): Synthesis of (2-bromo-2-methyl-propionyloxyethyl)-heptacyclopentyloctasilsesquioxane The same operation as in Example 75 is carried out, except that the compound (45) obtained in Example 50 is substituted for the compound (43), whereby a compound represented by Formula (66) can be obtained.

(66)

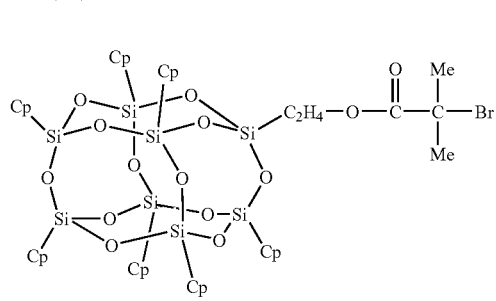

Example 78

Compound (67): Synthesis of (2-bromo-2-methyl-propionyloxyethyl)-heptaethyloctasilsesquioxane The same operation as in Example 75 is carried out, except that the compound (46) obtained in Example 51 is substituted for the compound (43), whereby a compound represented by Formula (67) can be obtained.

(67)

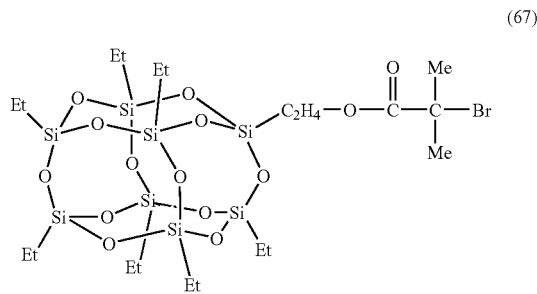

Example 79

Compound (68): Synthesis of (2-bromo-2-methyl-propionyloxyethyl)-heptaisobutyloctasilsesquioxane The same operation as in Example 75 is carried out, except that the compound (47) obtained in Example 52 is substituted for the compound (43), whereby a compound represented by Formula (68) can be obtained.

(68)

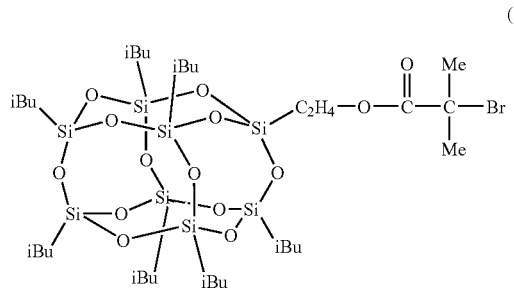

Example 80

Compound (69): Synthesis of (2-bromo-2-methyl-propionyloxyethyl)-heptaisooctyloctasilsesquioxane The same operation as in Example 75 is carried out, except that the compound (48) obtained in Example 53 is substituted for the compound (43), whereby a compound represented by Formula (69) can be obtained.

(69)

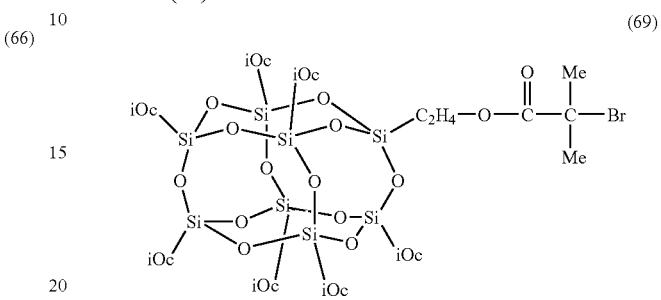

Example 81

Compound (70): Synthesis of (2-bromo-2-methyl-propionyloxyethyl)-heptatrifluoropropyloctasilsesquioxane A 25 ml-Kjeldahl flask was charged with the compound (49) (0.29 g), triethylamine (0.05 g) dried on molecular sieves (4 A) and dry methylene chloride (6.66 g) under argon atmosphere. The compound (49) was dissolved therein while stirring at a room temperature by means of a magnetic stirrer, and then the solution was cooled on a dry ice-methanol bath to maintain a solution temperature at −78° C. Then, 2-bromo-2-methylpropionyl bromide (0.12 g, 2.0 equivalent based on the compound (49)) was quickly added to the above solution and stirred at −78° C. for one hour, and then the solution was further stirred at a room temperature for 2 hours. After finishing the reaction, a triethylamine-hydrobromic acid salt was removed by filtration. Methylene chloride (100 ml) was added to the reaction liquid obtained, and it was washed in order once with water (300 ml), twice with a sodium hydrogencarbonate aqueous solution (1%, 300 ml) and twice with water (300 ml) and then dried on anhydrous magnesium sulfate (5 g). Thereafter, the above liquid was concentrated at a room temperature by means of a rotary evaporator to reduce a liquid amount to about 20 ml. Toluene (400 ml) was added to this concentrate (20 ml) to deposit a solid component. Then, it was left standing still in a freezing chamber of −35° C. to sufficiently deposit the solid component, and then solid-liquid separation was carried out by filtration. The solid component thus obtained was dried (40° C., 6 hours) under reduced pressure to obtain a white solid matter (0.17 g, yield: 60%).

As a result of carrying out GPC measurement of the compound obtained, a single peak was confirmed, and the presence of impurities was not confirmed. It was found from the results of $^1$H-NMR, $^{13}$C-NMR and $^{29}$Si-NMR each shown below that the white solid matter obtained had a structure represented by Formula (70).

$^1$H NMR (400 MHz, TMS standard: δ=0.0 ppm): 4.28 (t, 2H, —O—CH$_2$—), 2.15 (m, 14H, —[CH$_2$]—CF$_3$), 1.93 (s, 6H, —C(Br)(CH$_3$)$_2$), 1.25 (t, 2H, Si—[CH$_2$]—CH$_2$—O—), 0.94 (m, 14H, Si—[CH$_2$]—CH$_2$—CF$_3$)

$^{13}$C NMR (100 MHz, TMS standard: δ=0.0 ppm): 171.23 (C=O), 131.32, 128.57, 125.79, 123.07 (—CF$_3$), 61.83

(—CH$_2$—O—), 55.80 (—C(Br)), 30.70 ((—CH$_3$)$_2$), 28.13, 27.83, 27.52, 27.23 (—[CH$_2$]—CF$_3$), 12.45 (Si—[CH$_2$]—CH$_2$—O—), 4.00 (Si—[CH$_2$]—CH$_2$—CF$_3$)

$^{29}$Si NMR (79 MHz, TMS standard: δ=0.0 ppm): −69.02 (—CH$_2$—SiO$_{1.5}$), −67.67, −67.73 (CF$_3$—CH$_2$—CH$_2$—SiO$_{1.5}$)

(70)

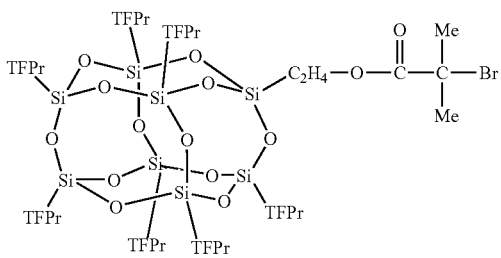

Example 82

Compound (71): Synthesis of (2-bromo-2-methyl-propionyloxyethyl)-hydroxyethyl-heptatridecafluoro-1,1,2,2-tetrahydrooctyloctasilsesquioxane The same operation as in Example 81 is carried out, except that the compound (62) obtained in Example 73 is substituted for the compound (43) and that methylene chloride is changed to AK-225, whereby a compound represented by Formula (71) can be obtained.

(71)

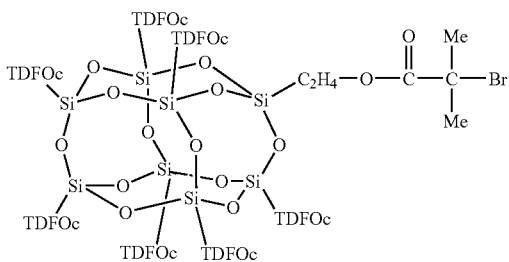

Example 83

Compound (72): Synthesis of (2-bromo-2-methyl-propionyloxypropyl)-heptaphenyloctasilsesquioxane A 100 ml-Kjeldahl flask was charged with the compound (50) (2.0 g) obtained by the method shown in Example 59, triethylamine (0.3 g) dried on molecular sieves (4 A) and dry methylene chloride (38 g) under argon atmosphere. The compound (50) was dissolved therein while stirring at a room temperature by means of a magnetic stirrer, and then the solution was cooled on a dry ice-methanol bath to maintain a solution temperature at −78° C. Then, 2-bromo-2-methylpropionyl bromide (0.68 g, 1.5 equivalent based on the compound (50)) was quickly added to the above solution and stirred at −78° C. for one hour, and then the solution was further stirred at a room temperature for 2 hours. After finishing the reaction, a triethylamine-hydrobromic acid salt was removed by filtration. Methylene chloride (100 ml) was added to the reaction liquid obtained, and it was washed in order once with water (300 ml), twice with a sodium hydrogencarbonate aqueous solution (1%, 300 ml) and twice with water (300 ml) and then dried on anhydrous magnesium sulfate (5 g). Thereafter, the above liquid was concentrated at a room temperature by means of a rotary evaporator to reduce a liquid amount to about 20 ml. Methanol (400 ml) was added to this concentrate (20 ml) to deposit a solid component. Then, it was left standing still in a freezing chamber of −35° C. to thereby sufficiently deposit the solid component, and then solid-liquid separation was carried out by filtration. The solid component thus obtained was dried (40° C., 6 hours) under reduced pressure to obtain a white solid matter (1.1 g, yield: 48.0%).

As a result of carrying out GPC measurement of the white solid matter obtained, a single peak was confirmed, and the presence of impurities was not confirmed. It was found from the results of IR, $^1$H-NMR, $^{13}$C-NMR and $^{29}$Si-NMR each shown below that the white solid matter obtained had a structure represented by Formula (72).

IR (KBr method: ν=1740 (C=O), 1430 (Si-Ph), 1270 (C—O) 1135 to 1090 (Si-Ph), 1090 to 1000 (Si—O—Si) cm$^{-1}$.

$^1$H NMR (400 MHz, TMS standard: δ=0.0 ppm): 7.82 to 7.72, 7.49 to 7.33 (m, 35H, Ph-Si), 4.17 to 4.14 (t, 2H, —O—CH$_2$—), 1.92 to 1.88 (t, 2H, —CH$_2$— [CH$_2$]—CH$_2$—), 1.79 (s, 6H, —C(Br)(CH$_3$)$_2$), 0.96 to 0.91 (t, 2H, —CH$_2$—Si).

$^{13}$C NMR (100 MHz, TMS standard: δ=0.0 ppm): 172.1 (C=O), 134.7 to 134.6, 131.3, 130.7 to 130.6, 128.4 to 128.3 (Ph-Si), 68.0 (—CH$_2$—O—), 56.3 (—C(Br)), 31.1 ((—CH$_3$)$_2$), 22.4 (—CH$_2$—[CH$_2$]—CH$_2$—), 8.4 (Si—CH$_2$—).

$^{29}$Si NMR (79 MHz, TMS standard: δ=0.0 ppm): −65.58 (—CH$_2$—SiO$_{1.5}$), −78.46, −78.80 (Ph-SiO$_{1.5}$).

(72)

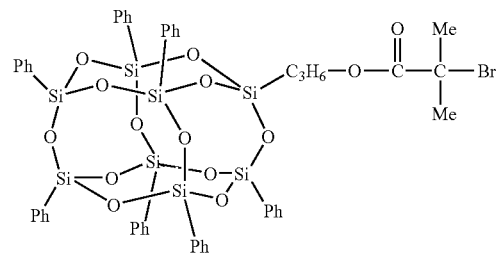

Example 84

Compound (73): Synthesis of (2-bromo-2-methyl-propionyloxypropyl)-heptacyclohexyloctasilsesquioxane The same operation as in Example 83 is carried out, except that the compound (51) obtained in Example 60 is substituted for the compound (50), whereby a compound represented by Formula (73) can be obtained.

(73)

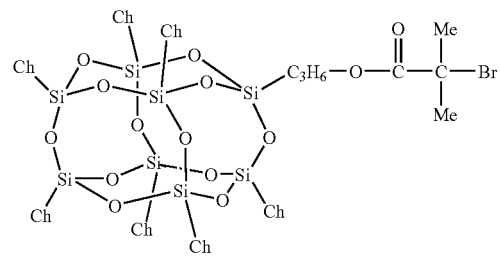

Example 85

Compound (74): Synthesis of (2-bromo-2-methyl-propionyloxypropyl)-heptacyclopentyloctasilsesquioxane The same operation as in Example 83 is carried out, except that the compound (52) obtained in Example 61 is substituted for the compound (50), whereby a compound represented by Formula (74) can be obtained.

(74)

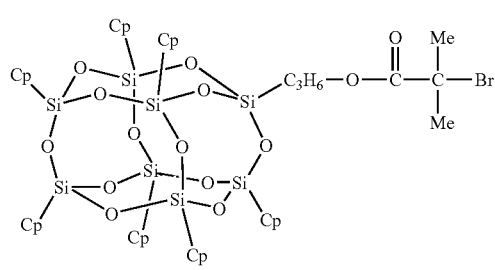

Example 86

Compound (75): Synthesis of (2-bromo-2-methyl-propionyloxypropyl)-heptaethyloctasilsesquioxane The same operation as in Example 83 is carried out, except that the compound (53) obtained in Example 62 is substituted for the compound (50), whereby a compound represented by Formula (75) can be obtained.

(75)

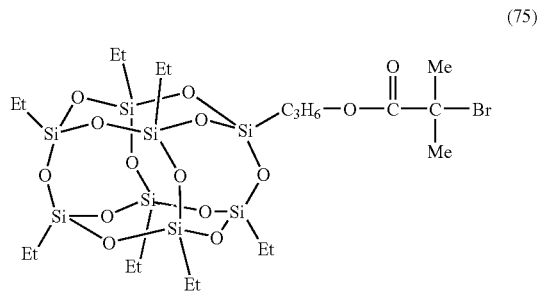

Example 87

Compound (76): (Synthesis of 2-bromo-2-methyl-propionyloxypropyl)-heptaisobutyloctasilsesquioxane The same operation as in Example 83 is carried out, except that the compound (54) obtained in Example 63 is substituted for the compound (50), whereby a compound represented by Formula (76) can be obtained.

(76)

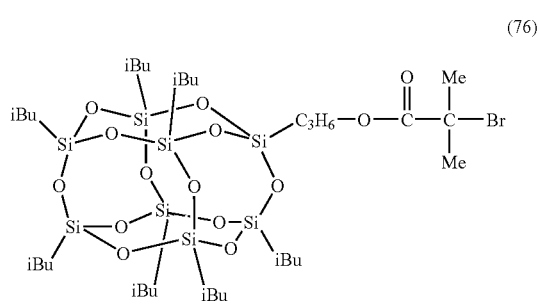

Example 88

Compound (77): Synthesis of (2-bromo-2-methyl-propionyloxypropyl)-heptaisooctyloctasilsesquioxane The same operation as in Example 83 is carried out, except that the compound (55) obtained in Example 64 is substituted for the compound (50), whereby a compound represented by Formula (77) can be obtained.

(77)

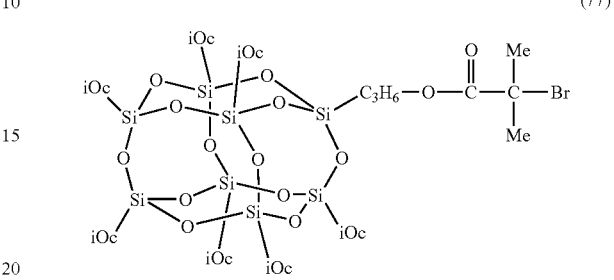

Example 89

Compound (78): Synthesis of (2-bromo-2-methyl-propionyloxypropyl)-heptatrifluoropropyloctasilsesquioxane The same operation as in Example 83 is carried out, except that the compound (56) obtained in Example 65 is substituted for the compound (50), whereby a compound represented by Formula (78) can be obtained.

(78)

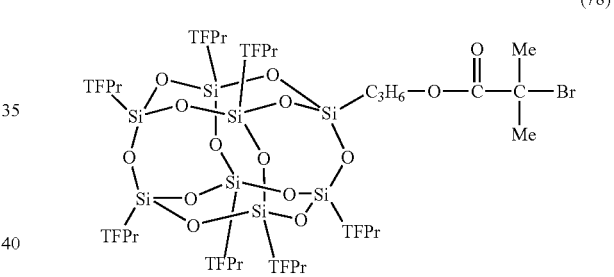

Example 90

Compound (79): Synthesis of (2-bromo-2-methyl-propionyloxypropyl)-heptatridecafluoro-1,1,2,2-tetrahydrooctyloctasilsesquioxane The same operation as in Example 81 is carried out, except that the compound (63) obtained in Example 74 is substituted for the compound (50) and that methylene chloride is changed to AK-225, whereby a compound represented by Formula (79) can be obtained.

(79)

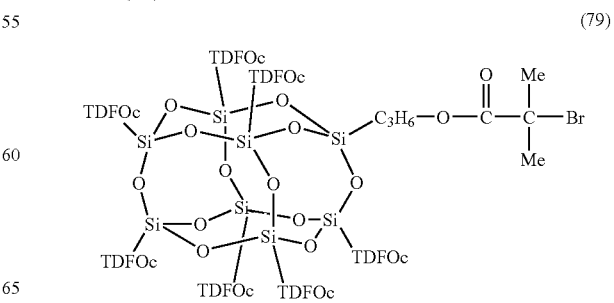

Example 91

Preparation of Solution for Polymerization

Cuprous bromide was introduced into a heat resistant glass-made ampul in a draft which was cut off from a UV ray, and a compound (64)/styrene/L-(−)-sparteine/diphenyl ether solution was further added thereto and quickly cooled using liquid nitrogen. Then, freezing vacuum deaeration (pressure: 1.0 Pa) was carried out three times by means of a vacuum device equipped with an oil-sealed rotary pump, and the ampul was quickly sealed by means of a hand burner while maintaining a state of vacuum. In this case, a proportion of the compound (64), styrene, cuprous bromide and L-(−)-sparteine in the above solution for polymerization was set to 1:500:1:2 in terms of a mole ratio in the above order, and a use amount of diphenyl ether was set to such an amount that a concentration of styrene became 50 wt %.

<Polymerization>

The sealed heat resistant glass-made ampul was set in a constant temperature shaking bath, and polymerization was carried out to obtain a brown viscous solution of a polymer (1a). In this case, the polymerization temperature was 110° C., and the polymerization time was 1.0 hour. Thereafter, a prescribed amount of the solution of the polymer (1a) was sampled and diluted with tetrahydrofuran, and then it was subjected to GPC measurement. A monomer conversion rate in this polymerization reaction system was analyzed based on a peak area obtained from a GPC measured value of a polystyrene solution having a known concentration. The polymer obtained was reprecipitated and refined using methanol. Then, a tetrahydrofuran solution (1 wt %) of the above polymer was prepared, and this was allowed to pass through a column filled with activated carbon to thereby remove the copper complex by adsorption. Further, this solution was dropwise added to methanol to reprecipitate the polymer, and this was dried (80° C., 6 hours) under reduced pressure. Shown in Table 10 are the analytical results of the monomer conversion rate and a theoretical number average molecular weight, a number average molecular weight and a molecular weight distribution of the polymer (1a).

Examples 92 to 100

Polymerization was carried out in the same manner as in Example 91 to obtain the respective brown viscous solutions of a polymer (1b) to a polymer (1j), except that the polymerization time was changed as shown in Table 10. Then, the monomer conversion rates were determined in the same manner as in the case of Example 91, and the respective polymers were refined in the same manner as in the case of Example 91 to determine a theoretical number average molecular weight, a number average molecular weight and a molecular weight distribution of the polymers. The results thereof are shown in Table 10.

TABLE 10

| Example No. | Example No. | Polymerization time (hr) | Conversion (mol-%) | Mn teoretical value | Mn measured value | Molecular weight distribution (Mw/Mn) |
|---|---|---|---|---|---|---|
| 91 | 1a | 1.0 | 6.1 | 4,300 | 3,700 | 1.14 |
| 92 | 1b | 2.0 | 12.3 | 7,600 | 7,600 | 1.11 |
| 93 | 1c | 3.2 | 17.8 | 10,400 | 11,400 | 1.09 |
| 94 | 1d | 3.7 | 22.5 | 12,900 | 13,200 | 1.11 |
| 95 | 1e | 4.0 | 29.1 | 16,300 | 17,000 | 1.11 |
| 96 | 1f | 5.0 | 28.9 | 16,200 | 17,000 | 1.14 |
| 97 | 1g | 6.5 | 34.9 | 19,300 | 20,700 | 1.15 |
| 98 | 1h | 9.0 | 45.9 | 25,100 | 24,900 | 1.20 |
| 99 | 1i | 13.0 | 64.1 | 34,000 | 36,500 | 1.23 |
| 100 | 1j | 18.0 | 75.7 | 40,600 | 45,000 | 1.30 |

Polymers can be obtained by the methods according to the examples described above using the compounds (65) to (69) in place of the compound (65).

Example 101

Preparation of Solution for Polymerization

Cuprous bromide was introduced into a heat resistant glass-made ampul in a draft which was cut off from a UV ray, and a compound (64)/methyl methacrylate/L-(−)-sparteine/anisole solution was further added thereto and quickly cooled using liquid nitrogen. Then, freezing vacuum deaeration (pressure: 1.0 Pa) was carried out three times by means of a vacuum device equipped with an oil-sealed rotary pump, and the ampul was quickly sealed by means of a hand burner while maintaining a state of vacuum. In this case, a proportion of the compound (64), methyl methacrylate, cuprous bromide and L-(−)-sparteine in the above solution for polymerization was set to 1:500:0.5:1 in terms of a mole ratio in the above order, and a use amount of anisole was set to such an amount that a concentration of methyl methacrylate became 25 wt %.

<Polymerization>

The sealed heat resistant glass-made ampul was set in a constant temperature shaking bath, and polymerization was carried out to obtain a brown viscous solution of a polymer (2a). In this case, the polymerization temperature was 70° C., and the polymerization time was 0.5 hour. Thereafter, a prescribed amount of the solution of the polymer (2a) was sampled and diluted with tetrahydrofuran, and then it was subjected to GPC measurement. A monomer conversion rate in this polymerization reaction system was analyzed based on a peak area obtained from a GPC measured value of a polystyrene solution having a known concentration. The polymer obtained was reprecipitated and refined using hexane. Then, a tetrahydrofuran solution (1 wt %) of the above polymer was prepared, and this was allowed to pass through a column filled with activated carbon to thereby remove the copper complex by adsorption. Further, this solution was dropwise added to hexane to reprecipitate the polymer, and this was dried (80° C., 6 hours) under reduced pressure. Shown in Table 11 are the analytical results of the conversion rate and a theoretical number average molecular weight, a number average molecular weight and a molecular weight distribution of the polymer (2a).

Example 102

Polymerization was carried out in the same manner as in the case of Example 101 to obtain a brown viscous solution of a polymer (2b), except that a proportion of the compound (64), methyl methacrylate, copper (cuprous bromide:cupric bromide=85:15 (mole ratio)) and L-(−)-sparteine in the solution for polymerization was set to 1:500:0.5:1 in terms of a mole ratio in the above order and that a use amount of anisole was set to such an amount that a concentration of methyl methacrylate became 50 wt %. In this case, the polymerization temperature was 70° C., and the polymerization time was 1.0 hour. Then, a prescribed amount of the solution of the polymer (2b) was sampled and subjected to GPC measurement in the same manner as in the case of Example 101. The polymer obtained was refined in the same manner as in the case of Example 101. Shown in Table 11 are the analytical results of the conversion rate and a theoretical number average molecular weight, a number average molecular weight and a molecular weight distribution of the polymer (2b).

Example 103

Polymerization was carried out in the same manner as in the case of Example 101 to obtain a brown viscous solution of a polymer (2c), except that a proportion of the compound (64), methyl methacrylate, copper (cuprous bromide:cupric bromide=90:10 (mole ratio)) and L-(−)-sparteine in the solution for polymerization was set to 1:500:0.5:1 in terms of a mole ratio in the above order and that a use amount of anisole was set to such an amount that a concentration of methyl methacrylate became 50 wt %. In this case, the polymerization temperature was 70° C., and the polymerization time was 1.0 hour. Then, a prescribed amount of the solution of the polymer (2c) was sampled and subjected to GPC measurement in the same manner as in the case of Example 101. The polymer obtained was refined in the same manner as in the case of Example 101. Shown in Table 11 are the analytical results of the conversion rate and a theoretical number average molecular weight, a number average molecular weight and a molecular weight distribution of the polymer (2c).

Example 104

Polymerization was carried out in the same manner as in the case of Example 101 to obtain a brown viscous solution of a polymer (2d), except that a proportion of the compound (64), methyl methacrylate, cuprous bromide and L-(−)-sparteine in the solution for polymerization was set to 1:500: 2:4 in terms of a mole ratio in the above order and that a use amount of anisole was set to such an amount that a concentration of methyl methacrylate became 50 wt %. In this case, the polymerization temperature was 70° C., and the polymerization time was 0.5 hour. Then, a prescribed amount of the solution of the polymer (2d) was sampled and subjected to GPC measurement in the same manner as in the case of Example 101. The polymer obtained was refined in the same manner as in the case of Example 101. Shown in Table 11 are the analytical results of the conversion rate and a theoretical number average molecular weight, a number average molecular weight and a molecular weight distribution of the polymer (2d).

Example 105

Polymerization was carried out in the same manner as in the case of Example 101 to obtain a brown viscous solution of a polymer (2e), except that a proportion of the compound (64), methyl methacrylate, cuprous bromide and L-(−)-sparteine in the solution for polymerization was set to 1:500: 1:2 in terms of a mole ratio in the above order and that a use amount of anisole was set to such an amount that a concentration of methyl methacrylate became 50 wt %. In this case, the polymerization temperature was 70° C., and the polymerization time was 0.5 hour. Then, the respective polymers were refined in the same manner as in the case of Example 101. Shown in Table 11 are the analytical results of a number average molecular weight and a molecular weight distribution of the polymer (2e). In this case, the value of the conversion rate was not obtained and therefore a theoretical number average molecular weight of the polymer (2e) could not be obtained.

Example 106

Polymerization was carried out in the same manner as in the case of Example 101 to obtain a brown viscous solution of a polymer (2f), except that a proportion of the compound (64), methyl methacrylate, cuprous bromide and L-(−)-sparteine in the solution for polymerization was set to 1:500:0.5:1 in terms of a mole ratio in the above order and that a use amount of anisole was set to such an amount that a concentration of methyl methacrylate became 50 wt %. In this case, the polymerization temperature was 70° C., and the polymerization time was 0.5 hour. Then, a prescribed amount of the solution of the polymer (2f) was sampled and subjected to GPC measurement in the same manner as in the case of Example 101. The polymer obtained was refined in the same manner as in the case of Example 101. Shown in Table 11 are the analytical results of the conversion rate and a theoretical number average molecular weight, a number average molecular weight and a molecular weight distribution of the polymer (2f).

Example 107

Polymerization was carried out in the same manner as in the case of Example 101 to obtain a brown viscous solution of a polymer (2g), except that a proportion of the compound (64), methyl methacrylate, cuprous bromide and L-(−)-sparteine in the solution for polymerization was set to 1:500: 0.25:0.50 in terms of a mole ratio in the above order and that a use amount of anisole was set to such an amount that a concentration of methyl methacrylate became 50 wt %. In this case, the polymerization temperature was 70° C., and the polymerization time was 0.6 hour. Then, a prescribed amount of the solution of the polymer (2g) was sampled and subjected to GPC measurement in the same manner as in the case of Example 101. The polymer obtained was refined in the same manner as in the case of Example 101. Shown in Table 11 are the analytical results of the conversion rate and a theoretical number average molecular weight, a number average molecular weight and a molecular weight distribution of the polymer (2g).

Example 108

Polymerization was carried out in the same manner as in the case of Example 101 to obtain a brown viscous solution of a polymer (2h), except that a proportion of the compound (64), methyl methacrylate, cuprous bromide and L-(−)-sparteine in the solution for polymerization was set to 1:500:1:2 in terms of a mole ratio in the above order and that a use amount of anisole was set to such an amount that a concentration of methyl methacrylate became 50 wt %. In this case, the polymerization temperature was 70° C., and the polymerization time was 3.0 hours. Then, a prescribed amount of the solution of the polymer (2h) was sampled and subjected to GPC measurement in the same manner as in the case of Example 101. The polymer obtained was refined in the same manner as in the case of Example 101. Shown in Table 11 are the analytical results of the conversion rate and a theoretical number average molecular weight, a number average molecular weight and a molecular weight distribution of the polymer (2h).

<Polymerization>

The sealed heat resistant glass-made ampul was set in a constant temperature shaking bath, and polymerization was carried out to obtain a brown viscous solution of a polymer (3a). In this case, the polymerization temperature was 70° C., and the polymerization time was 0.5 hour. A monomer conversion rate in this polymerization reaction system was determined from the relation of a proton ratio of substituents in the respective monomer and polymer by diluting the solution of the polymer (3a) with deuterated chloroform and then subjecting the solution to $^1$H-NMR measurement. The polymer obtained was reprecipitated and refined using hexane. Then, a tetrahydrofuran solution (1 wt %) of the above polymer was prepared, and this was allowed to pass through a column filled with activated carbon to thereby remove the copper complex by adsorption. Further, this solution was dropwise added to

TABLE 11

| Example No. | Example No. | Polymerization time (hr) | Conversion (mol-%) | Mn teoretical value | Mn measured value | Molecular weight distribution (Mw/Mn) |
|---|---|---|---|---|---|---|
| 101 | 2a | 0.5 | 11.4 | 6,900 | 4,500 | 1.08 |
| 102 | 2b | 1.0 | 4.55 | 3,400 | 4,700 | 1.09 |
| 103 | 2c | 1.0 | 6.23 | 4,300 | 6,300 | 1.12 |
| 104 | 2d | 0.5 | 8.64 | 5,500 | 6,300 | 1.12 |
| 105 | 2e | 0.5 | — | — | 7,100 | 1.12 |
| 106 | 2f | 0.5 | 8.14 | 5,200 | 8,000 | 1.13 |
| 107 | 2g | 0.6 | 14.9 | 8,600 | 8,500 | 1.20 |
| 108 | 2h | 3.0 | 44.0 | 23,200 | 28,000 | 1.14 |

Polymers can be obtained by the methods according to the examples described above using the compounds (65) to (69) in place of the compound (64).

Example 109

Preparation of Solution for Polymerization

Cuprous bromide was introduced into a heat resistant glass-made ampul in a draft which was cut off from a UV ray, and a compound (72)/methyl methacrylate/L-(−)-sparteine/anisole solution was further added thereto and quickly cooled using liquid nitrogen. Then, freezing vacuum deaeration (pressure: 1.0 Pa) was carried out three times by means of a vacuum device equipped with an oil-sealed rotary pump, and the ampul was quickly sealed by means of a hand burner while maintaining a state of vacuum. In this case, a proportion of the compound (72), methyl methacrylate, cuprous bromide and L-(−)-sparteine in the above solution for polymerization was set to 1:300:1:2 in terms of a mole ratio in the above order, and a use amount of anisole was set to such an amount that a concentration of methyl methacrylate became 50 wt %.

hexane to reprecipitate the polymer, and this was dried (80° C., 6 hours) under reduced pressure. Shown in Table 12 are the analytical results of the conversion rate and a theoretical number average molecular weight, a number average molecular weight and a molecular weight distribution of the polymer (3a).

Examples 110 to 115

Polymerization was carried out in the same manner as in Example 109 to obtain the respective brown viscous solutions of a polymer (3b) to a polymer (3g), except that the polymerization time was changed as shown in Table 12. Then, the monomer conversion rates were determined in the same manner as in the case of Example 109, and the respective polymers were refined in the same manner as in the case of Example 109. Shown in Table 12 are the analytical results of the conversion rates corresponding to the respective polymers and the respective theoretical number average molecular weights, number average molecular weights and molecular weight distributions of the polymer (3b) to the polymer (3g).

TABLE 12

| Example No. | Example No. | Polymerization time (hr) | Conversion (mol-%) | Mn teoretical value | Mn measured value | Molecular weight distribution (Mw/Mn) |
|---|---|---|---|---|---|---|
| 109 | 3a | 0.5 | 13.0 | 5,100 | 7,600 | 1.13 |
| 110 | 3b | 1.0 | 27.1 | 9,300 | 11,800 | 1.14 |
| 111 | 3c | 1.5 | 35.7 | 11,900 | 14,600 | 1.15 |
| 112 | 3d | 2.0 | 44.1 | 14,400 | 17,900 | 1.15 |
| 113 | 3e | 3.0 | 55.8 | 17,900 | 21,500 | 1.15 |
| 114 | 3f | 4.0 | 65.5 | 20,800 | 25,400 | 1.17 |
| 115 | 3g | 5.0 | 73.7 | 23,300 | 28,800 | 1.16 |

Polymers can be obtained by the methods according to the examples described above using the compounds (73) to (77) in place of the compound (72).

Example 116

Preparation of Solution for Polymerization

Cuprous bromide was introduced into a heat resistant glass-made ampul in a draft which was cut off from a UV ray, and a compound (72)/methyl methacrylate/L-(−)-sparteine/ anisole solution was further added thereto and quickly cooled using liquid nitrogen. Then, freezing vacuum deaeration (pressure: 1.0 Pa) was carried out three times by means of a vacuum device equipped with an oil-sealed rotary pump, and the ampul was quickly sealed by means of a hand burner while maintaining a state of vacuum. In this case, a proportion of the compound (72), methyl methacrylate, cuprous bromide and L-(−)-sparteine in the above solution for polymerization was set to 1:150:1:2 in terms of a mole ratio in the above order, and a use amount of anisole was set to such an amount that a concentration of methyl methacrylate became 50 wt %.

<Polymerization>

The sealed heat resistant glass-made ampul was set in a constant temperature shaking bath, and polymerization was carried out to obtain a brown viscous solution of a polymer (4a). In this case, the polymerization temperature was 70° C., and the polymerization time was 0.5 hour. A monomer conversion rate in this polymerization reaction system was determined from the relation of a proton ratio of substituents in the respective monomer and polymer by diluting the solution of the polymer (4a) with deuterated chloroform and then subjecting the solution to $^1$H-NMR measurement. The polymer obtained was reprecipitated and refined using hexane. Then, a tetrahydrofuran solution (1 wt %) of the above polymer was prepared, and this was allowed to pass through a column filled with activated carbon to thereby remove the copper complex by adsorption. Further, this solution was dropwise added to hexane to reprecipitate the polymer, and this was dried (80° C., 6 hours) under reduced pressure. Shown in Table 13 are the analytical results of the conversion rate and a theoretical number average molecular weight, a number average molecular weight and a molecular weight distribution of the polymer (4a).

Examples 117 to 122

Polymerization was carried out in the same manner as in Example 116 to obtain the respective brown viscous solutions of a polymer (4b) to a polymer (4g), except that the polymerization time was changed as shown in Table 13. Then, the monomer conversion rates were determined in the same manner as in the case of Example 116, and the respective polymers were refined in the same manner as in the case of Example 116. Shown in Table 13 are the analytical results of the conversion rates corresponding to the respective polymers and the respective theoretical number average molecular weights, number average molecular weights and molecular weight distributions of the polymer (4b) to the polymer (4g).

TABLE 13

| Example No. | Example No. | Polymerization time (hr) | Conversion (mol-%) | Mn teoretical value | Mn measured value | Molecular weight distribution (Mw/Mn) |
|---|---|---|---|---|---|---|
| 116 | 4a | 0.25 | 5.3 | 2,000 | 3,800 | 1.07 |
| 117 | 4b | 0.50 | 16.8 | 3,700 | 6,200 | 1.10 |
| 118 | 4c | 1.00 | 39.5 | 7,100 | 10,900 | 1.14 |
| 119 | 4d | 1.50 | 54.1 | 9,300 | 11,800 | 1.15 |
| 120 | 4e | 2.00 | 61.9 | 10,500 | 13,200 | 1.15 |
| 121 | 4f | 2.50 | 66.4 | 11,100 | 13,900 | 1.16 |
| 122 | 4g | 3.00 | 76.4 | 12,600 | 15,400 | 1.18 |

Polymers can be obtained by the methods according to the examples described above using the compounds (73) to (77) in place of the compound (72).

Example 123

Preparation of Solution for Polymerization

Cuprous chloride was introduced into a Schlenk tube substituted with argon in a draft which was cut off from a UV ray, and a compound (70)/methyl methacrylate/4,4'-di(5-nonyl)-2,2'-bipyridine/dimethylformamide solution was further added thereto and quickly cooled using liquid nitrogen. Then, freezing vacuum deaeration (pressure: 1.0 Pa) was carried out three times by means of a vacuum device equipped with an oil-sealed rotary pump, and argon was finally introduced thereinto. In this case, a proportion of the compound (70), methyl methacrylate, cuprous chloride and 4,4'-di(5-nonyl)-2,2'-bipyridine in the above solution for polymerization was set to 1:399:1:2 in terms of a mole ratio in the above order, and a use amount of dimethylformamide was set to such an amount that a concentration of methyl methacrylate became 50 wt %.

<Polymerization>

The Schlenk tube described above was set in a constant temperature shaking bath, and polymerization was carried out to obtain a brown viscous solution of a polymer (5a). In this case, the polymerization temperature was 70° C., and the polymerization time was 0.5 hour. Then, a prescribed amount of the solution of the polymer (5a) was sampled and subjected to GPC measurement after diluted with tetrahydrofuran. A monomer conversion rate in this polymerization reaction system was determined from the relation of a proton ratio of substituents in the respective monomer and polymer by diluting the solution of the polymer (5a) with deuterated chloroform and then subjecting the solution to $^1$H-NMR measurement. The polymer obtained was reprecipitated and refined using hexane. Then, a tetrahydrofuran solution (1 wt %) of the above polymer was prepared, and this was allowed to pass through a column filled with activated carbon to thereby remove the copper complex by adsorption. Further, this solution was dropwise added to hexane to reprecipitate the polymer, and this was dried (80° C., 6 hours) under reduced pressure. Shown in Table 14 are the analytical results of a theoretical number average molecular weight, a number average molecular weight and a molecular weight distribution of the polymer (5a), and a difference was apparently observed between the theoretical values of the number average molecular weights and the measured values thereof.

<Analysis of Theoretical Number Average Molecular Weight of Graft Chain>

A theoretical number average molecular weight of the graft chain was calculated according to the following equation assuming that an ester bond which was an initiating end in the polymerization was cut off by hydrolysis brought about by hydrofluoric acid treatment and that all terminating ends in the polymerization had become Br. The results thereof are shown in Table 14-2.

<Calculating Equation>

Theoretical Mn of graft chain=(monomer consumption rate (mole %)/100)×$MW_M$×(mole ratio of vinyl base monomer to α-bromoester group)+ $MW_1$ <Parameters Used for Calculation>

$MW_M$=100(methyl methacrylate)

Mole ratio of vinyl base monomer to α-bromoester group=300

$MW_1$=167.01(BrC($CH_3$)$_2$$CO_2$H)

<Molecular Weight Measurement of Graft Chain>

The polymer (5a) (15.5 mg) was dissolved in toluene (2.0 ml) in a polypropylene-made microtube (10 ml) into which a rotator was introduced. A mixture of a phase transfer catalyst (trioctylmethylammonium chloride, 20 mg), hydrofluoric acid (1.0 ml) and water (3.0 ml) was added thereto, and the solution was stirred at 25° C. for 12 hours by means of a magnetic stirrer. After finishing the reaction, neutralizing treatment by sodium hydrogencarbonate was carried out, and then a prescribed amount of the supernatant organic layer was sampled and subjected to GPC measurement after diluted with tetrahydrofuran.

Results obtained by subjecting this polymer to GPC measurement are shown in Table 14-2, and it was found that they were almost consistent with theoretical Mn of the graft chains derived from the calculating equation described above. Accordingly, it was indicated that in the polymers before subjected to hydrofluoric acid treatment, the polymers themselves were aggregated by strong interaction between silsesquioxanes in tetrahydrofuran.

Examples 124 to 130

Polymerization was carried out in the same manner as in Example 123 to obtain the respective brown viscous solutions of a polymer (5b) to a polymer (5h), except that the polymerization time was changed as shown in Table 14-1. Then, a monomer conversion rate, a theoretical number average molecular weight, a number average molecular weight and a molecular weight distribution in the respective polymers were determined in the same manner as in the case of Example 123, and the results thereof are shown Table 14-1. In all polymers, a difference was apparently observed between the theoretical values of the number average molecular weights and the measured values thereof.

Then, calculation of a theoretical number average molecular weight of the graft chains, hydrofluoric acid treatment of the polymers and analysis of a number average molecular weight and a molecular weight distribution of the graft chains were carried out in the respective polymers in the same manner as in Example 123, and the results thereof are shown Table 14-1. It was found that measured Mn of the graft chains was almost consistent with theoretical MN thereof in all polymers. Accordingly, it was indicated that in the polymers obtained in the present examples, the polymers themselves were aggregated by strong interaction between silsesquioxanes in tetrahydrofuran.

TABLE 14-1

| Example No. | Example No. | Polymerization time (hr) | Conversion (mol-%) | Mn teoretical value | Mn measured value | Molecular weight distribution (Mw/Mn) |
| --- | --- | --- | --- | --- | --- | --- |
| 123 | 5a | 0.5 | 12.1 | 6,100 | 18,300 | 1.15 |
| 124 | 5b | 1.0 | 22.2 | 10,200 | 22,700 | 1.23 |
| 125 | 5c | 1.5 | 27.4 | 12,200 | 27,400 | 1.26 |
| 126 | 5d | 2.0 | 31.4 | 13,800 | 30,200 | 1.22 |
| 127 | 5e | 3.0 | 38.4 | 16,600 | 34,900 | 1.23 |
| 128 | 5f | 4.0 | 44.3 | 19,000 | 37,800 | 1.27 |
| 129 | 5g | 5.0 | 47.9 | 20,400 | 40,100 | 1.26 |
| 130 | 5h | 6.0 | 51.6 | 21,900 | 43,700 | 1.32 |

TABLE 14-2

(data on graft chain)

| Example No. | Example No. | Polymerization time (hr) | Mn measured value | Molecular weight distribution (Mw/Mn) |
| --- | --- | --- | --- | --- |
| 123 | 5a | 5,000 | 7,500 | 1.42 |
| 124 | 5b | 9,000 | 11,300 | 1.29 |
| 125 | 5c | 11,100 | 13,500 | 1.28 |
| 126 | 5d | 12,700 | 15,300 | 1.26 |
| 127 | 5e | 15,500 | 18,300 | 1.24 |
| 128 | 5f | 17,800 | 21,400 | 1.20 |
| 129 | 5g | 19,300 | 23,000 | 1.20 |
| 130 | 5h | 20,800 | 24,800 | 1.19 |

INDUSTRIAL APPLICABILITY

The silicon compound provided by the present invention is a silsesquioxane derivative having an excellent living polymerizable radical polymerization-initiating function. The silicon compound of the present invention shows an excellent living radical polymerizability particularly to styrene derivatives. For example, it is possible to initiate polymerization of a styrene base monomer by the silicon compound of the present invention to form a styrene base polymer with one point in the silsesquioxane structure of the present invention being used as a starting point. In the polymer thus obtained having an organic group of a silsesquioxane structure at an end, it is possible as well to positively make use of interaction between the organic groups of the silsesquioxane structure thereof. This makes it possible not only to obtain an organic-inorganic composite material having a distinct structure but also to control the structure of the above polymer as a molecular aggregate. Further, the silicon compound of the present invention has characteristics other than the function of a polymerization initiator. For example, α-haloester has a strong electrophilicity, and therefore reaction of the silicon compound of the present invention with nucleophilic reagents makes it possible to synthesize various silsesquioxane derivatives corresponding to the nucleophilic reagents. Accordingly, the silicon compound of the present invention is also useful as an intermediate in organic synthesis.

What is claimed is:

1. A silicon compound represented by Formula (1):

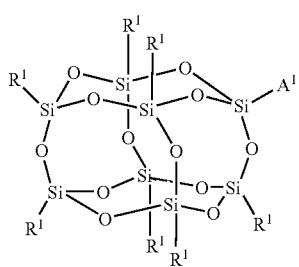

(1)

wherein $R^1$ is a group independently selected from hydrogen, alkyl having a carbon atom number of 1 to 40, substituted or non-substituted aryl and substituted or non-substituted arylalkyl; in this alkyl having a carbon atom number of 1 to 40, optional hydrogens may be substituted with fluorine, and optional —CH$_2$— may be substituted with —O—, —CH=CH—, cycloalkylene or cycloalkenylene; in alkylene in this arylalkyl, optional hydrogens may be substituted with fluorine, and optional —CH$_2$— may be substituted with —O— or —CH=CH—; and $A^1$ is a group having an α-haloester group, which does not have an addition-polymerizable double bond.

2. The silicon compound as described in claim 1, wherein $R^1$ is a group independently selected from hydrogen and alkyl having a carbon atom number of 1 to 30 in which optional hydrogens may be substituted with fluorine and in which optional —CH$_2$— may be substituted with —O— or cycloalkylene.

3. The silicon compound as described in claim 1, wherein $R^1$ is a group independently selected from alkenyl having a carbon atom number of 1 to 20 in which optional hydrogens may be substituted with fluorine and in which optional —CH$_2$— may be substituted with —O— or cycloalkylene and alkyl having a carbon atom number of 1 to 20 in which optional hydrogens may be substituted with fluorine and in which at least one —CH$_2$— is substituted with cycloalkenylene.

4. The silicon compound as described in claim 1, wherein $R^1$ is a group independently selected from non-substituted naphthyl and phenyl in which optional hydrogens may be substituted with halogen or alkyl having a carbon atom number of 1 to 10; and in the alkyl which is a substituent for the phenyl, optional hydrogens may be substituted with fluorine, and optional —CH$_2$— may be substituted with —O—, —CH=CH—, cycloalkylene or phenylene.

5. The silicon compound as described in claim 1, wherein $R^1$ is a group independently selected from phenylalkyls constituted from phenyl in which optional hydrogens may be substituted with halogen or alkyl having a carbon atom number of 1 to 12 and alkylene having a carbon atom number of 1 to 12 in which optional hydrogens may be substituted with fluorine and in which optional —CH$_2$— may be substituted with —O— or —CH=CH—; and in the alkyl which is a substituent for the phenyl, optional hydrogens may be substituted with fluorine, and optional —CH$_2$— may be substituted with —O—, —CH=CH—, cycloalkylene or phenylene.

6. The silicon compound as described in claim 1, wherein $R^1$ is a group independently selected from alkyl having a carbon atom number of 1 to 8 in which optional hydrogens may be substituted with fluorine and in which optional —CH$_2$— may be substituted with —O—, —CH=CH—, cycloalkylene or cycloalkenylene, phenyl in which optional hydrogens may be substituted with halogen, methyl or methoxy, non-substituted naphthyl and phenylalkyl constituted from phenyl in which optional hydrogens may be substituted with fluorine, alkyl having a carbon atom number of 1 to 4, vinyl or methoxy and alkylene which has a carbon atom number of 1 to 8 and in which optional —CH$_2$— may be substituted with —O— or —CH=CH—.

7. The silicon compound as described in claim 1, wherein all $R^1$'s are the same group selected from alkyl having a carbon atom number of 1 to 8 in which optional hydrogens may be substituted with fluorine and in which optional —CH$_2$— may be substituted with —O—, —CH=CH—, cycloalkylene or cycloalkenylene, phenyl in which optional hydrogens may be substituted with halogen, methyl or methoxy, non-substituted naphthyl and phenylalkyl constituted from phenyl in which optional hydrogens may be substituted with fluorine, alkyl having a carbon atom number of 1 to 4, vinyl or methoxy and alkylene which has a carbon atom number of 1 to 8 and in which optional —CH$_2$— may be substituted with —O— or —CH=CH—.

8. The silicon compound as described in claim 1, wherein all $R^1$'s are the same group selected from phenyl in which optional hydrogens may be substituted with halogen, methyl or methoxy, non-substituted naphthyl and phenylalkyl constituted from phenyl in which optional hydrogens may be substituted with fluorine, alkyl having a carbon atom number of 1 to 4, vinyl or methoxy and alkylene which has a carbon atom number of 1 to 8 and in which optional —CH$_2$— may be substituted with —O—.

9. The silicon compound as described in claim 1, wherein all $R^1$'s are the same group selected from ethyl, 2-methylpropyl, 2,4,4-trimethylpentyl, cyclopentyl, cyclohexyl, non-substituted phenyl, 3,3,3-trifluoropropyl and tridecafluoro-1,1,2,2-tetrahydrooctyl.

10. The silicon compound as described in claim 1, wherein all $R^1$'s are the same group selected from non-substituted phenyl and 3,3,3-trifluoropropyl.

11. The silicon compound as described in claim 1, wherein in Formula (1), $R^1$ is a group independently selected from hydrogen, alkyl having a carbon atom number of 1 to 40, substituted or non-substituted aryl and substituted or non-substituted arylalkyl; in this alkyl having a carbon atom number of 1 to 40, optional hydrogens may be substituted with fluorine, and optional —CH$_2$— may be substituted with —O—, —CH=CH—, cycloalkylene or cycloalkenylene; in alkylene in this arylalkyl, optional hydrogens may be substituted with fluorine, and optional —CH$_2$— may be substituted with —O— or —CH=CH—; and A$^1$ is a group represented by Formula (2):

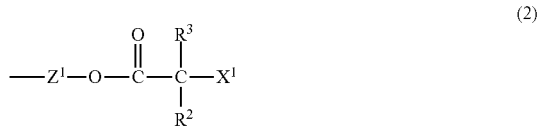

(2)

in Formula (2), X$^1$ is halogen; R$^2$ is alkyl having a carbon atom number of 1 to 20, aryl having a carbon atom number of 6 to 20 or aralkyl having a carbon atom number of 7 to 20; R$^3$ is hydrogen, alkyl having a carbon atom number of 1 to 20, aryl having a carbon atom number of 6 to 20 or aralkyl having a carbon atom number of 7 to 20; Z$^1$ is alkylene having a carbon atom number of 1 to 20 or alkenylene having a carbon atom number of 3 to 8; and in these alkylene and alkenylene, optional —CH$_2$— may be substituted with —O—.

12. The silicon compound as described in claim 11, wherein R$^1$ is a group independently selected from hydrogen and alkyl having a carbon atom number of 1 to 30 in which optional hydrogens may be substituted with fluorine and in which optional —CH$_2$— may be substituted with —O— or cycloalkylene.

13. The silicon compound as described in claim 11, wherein R$^1$ is a group independently selected from alkenyl having a carbon atom number of 1 to 20 in which optional hydrogens may be substituted with fluorine and in which optional —CH$_2$— may be substituted with —O— or cycloalkylene and alkyl having a carbon atom number of 1 to 20 in which optional hydrogens may be substituted with fluorine and in which at least one —CH$_2$— is substituted with cycloalkenyl.

14. The silicon compound as described in claim 11, wherein R$^1$ is a group independently selected from non-substituted naphthyl and phenyl in which optional hydrogens may be substituted with halogen or alkyl having a carbon atom number of 1 to 10; and in the alkyl which is a substituent for the phenyl, optional hydrogens may be substituted with fluorine, and optional —CH$_2$— may be substituted with —O—, —CH=CH—, cycloalkylene or phenylene.

15. The silicon compound as described in claim 11, wherein R$^1$ is a group independently selected from phenylalkyls constituted from phenyl in which optional hydrogens may be substituted with halogen or alkyl having a carbon atom number of 1 to 12 and alkylene having a carbon atom number of 1 to 12 in which optional hydrogens may be substituted with fluorine and in which optional —CH$_2$— may be substituted with —O— or —CH=CH—; and in the alkyl which is a substituent for the phenyl, optional hydrogens may be substituted with fluorine, and optional —CH$_2$— may be substituted with —O—, —CH=CH—, cycloalkylene or phenylene.

16. The silicon compound as described in claim 11, wherein R$^1$ is a group independently selected from alkyl having a carbon atom number of 1 to 8 in which optional hydrogens may be substituted with fluorine and in which optional —CH$_2$— may be substituted with —O—, —CH=CH—, cycloalkylene or cycloalkenylene, phenyl in which optional hydrogens may be substituted with halogen, methyl or methoxy, non-substituted naphthyl and phenylalkyl constituted from phenyl in which optional hydrogens may be substituted with fluorine, alkyl having a carbon atom number of 1 to 4, vinyl or methoxy and alkylene which has a carbon atom number of 1 to 8 and in which optional —CH$_2$— may be substituted with —O— or —CH=CH—.

17. The silicon compound as described in claim 11, wherein all R$^1$'s are the same group selected from alkyl having a carbon atom number of 1 to 8 in which optional hydrogens may be substituted with fluorine and in which optional —CH$_2$— may be substituted with —O—, —CH=CH—, cycloalkylene or cycloalkenylene, phenyl in which optional hydrogens may be substituted with halogen, methyl or methoxy, non-substituted naphthyl and phenylalkyl constituted from phenyl in which optional hydrogens may be substituted with fluorine, alkyl having a carbon atom number of 1 to 4, vinyl or methoxy and alkylene which has a carbon atom number of 1 to 8 and in which optional —CH$_2$— may be substituted with —O— or —CH=CH—.

18. The silicon compound as described in claim 11, wherein all R$^1$'s are the same group selected from phenyl in which optional hydrogens may be substituted with halogen, methyl or methoxy, non-substituted naphthyl and phenylalkyl constituted from phenyl in which optional hydrogens may be substituted with fluorine, alkyl having a carbon atom number of 1 to 4, vinyl or methoxy and alkylene which has a carbon atom number of 1 to 8 and in which optional —CH$_2$— may be substituted with —O—.

19. The silicon compound as described in claim 11, wherein all R$^1$'s are the same group selected from ethyl, 2-methylpropyl, 2,4,4-trimethylpentyl, cyclopentyl, cyclohexyl, non-substituted phenyl, 3,3,3-trifluoropropyl and tridecafluoro-1,1,2,2-tetrahydrooctyl.

20. The silicon compound as described in claim 11, wherein all R$^1$'s are the same group selected from non-substituted phenyl and 3,3,3-trifluoropropyl.

21. The silicon compound as described in claim 11, wherein Z$^1$ is alkylene which has a carbon atom number of 1 to 20 and in which optional —CH$_2$— may be substituted with —O—.

22. The silicon compound as described in claim 11, wherein Z$^1$ is —C$_2$H$_4$—O—C$_3$H$_6$—, —C$_3$H$_6$— or —C$_2$H$_4$—; R$^2$ is methyl or ethyl; R$^3$ is hydrogen, methyl or ethyl; and X$^1$ is bromine.

23. The silicon compound as described in claim 11, wherein Z$^1$ is —C$_3$H$_6$— or —C$_2$H$_4$—; both of R$^2$ and R$^3$ are methyl; and X$^1$ is bromine.

24. A process for producing the silicon compound represented by Formula (1) as described in claim 1, which comprises reacting a compound represented by Formula (3) with acid halide having a halogenated alkyl group:

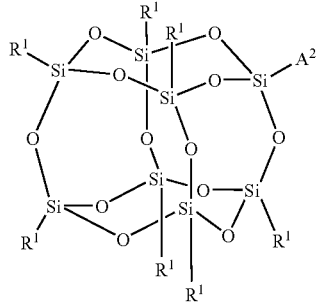

(3)

wherein R$^1$ is a group independently selected from hydrogen, alkyl having a carbon atom number of 1 to 40, substituted or non-substituted aryl and substituted or non-substituted arylalkyl; in this alkyl having a carbon atom number of 1 to 40, optional hydrogens may be substituted with fluorine, and optional —CH$_2$— may be substituted with —O—, —CH=CH—, cycloalkylene or cycloalkenylene; in alkylene in this arylalkyl, optional hydrogens may be substituted with fluorine, and optional —CH$_2$— may be substituted with —O— or —CH═CH—; and A$^2$ is an organic group having a terminal hydroxyl group.

25. A polymer obtained by polymerizing an addition-polymerizable monomer using the silicon compound as described in claim 1 as an initiator and using a transition metal complex as a catalyst, wherein the addition-polymerizable monomer is at least one member selected from the group consisting of (meth)acrylic acid, methyl (meth)acrylate, ethyl (meth)acrylate, n-propyl(meth)acrylate, isopropyl(meth)acrylate, n-butyl (meth)acrylate, isobutyl(meth)acrylate, tert-butyl(meth)acrylate, n-pentyl(meth)acrylate, n-hexyl (meth)acrylate, cyclohexyl(meth)acrylate, n-heptyl(meth)acrylate, n-octyl(meth)acrylate, 2-ethylhexyl(meth)acrylate, nonyl (meth)acrylate, decyl(meth)acrylate, dodecyl(meth)acrylate, phenyl(meth)acrylate, toluoyl(meth)acrylate, benzyl(meth)acrylate, 2-methoxyethyl (meth)acrylate, 3-methoxypropyl (meth)acrylate, 3-methoxybutyl(meth)acrylate, 2-hydroxyethyl (meth)acrylate, 2-hydroxypropyl(meth)acrylate, stearyl(meth)acrylate, glycidyl(meth)acrylate, 3-ethyl-3-(meth)acryloyloxymethyloxetane, 2-(meth)acryloyloxyethylisocyanate, 2-aminoethyl (meth)acrylate, 2-(2-bromopropionylyloxy)ethyl(meth)acrylate, 2-(2-bromoisobutyryloxy) ethyl (meth)acrylate, 1-(meth)acryloxy-2-phenyl-2-(2,2,6,6-tetramethyl-piperidinyloxy)ethane, (1-(4-((4-(meth)acryloxy)ethoxyethyl)phenylethoxy)piperidine, γ-(methacryloyloxypropyl)trimethoxysilane, 3-(3,5,7,9,11,13,15-heptaethylpentacyclo-[9.5.1.1$^{3,9}$.1$^{5,15}$.1$^{7,13}$]octasiloxane-1-yl)propyl(meth)acrylate, 3-(3,5,7,9,11,13,15-heptaisobutyl-pentacyclo[9.5.1.1$^{3,9}$.1$^{5,15}$.1$^{7,13}$]octasiloxane-1-yl)propyl(meth)acrylate, 3-(3,5,7,9,11,13,15-heptaisooctylpentacyclo[9.5.1.1$^{3,9}$.1$^{5,15}$.1$^{7,13}$]-octasiloxane-1-yl)propyl (meth)acrylate, 3-(3,5,7,9,11,13,15-heptacyclopentylpentacyclo-[9.5.1.1$^{3,9}$.1$^{5,15}$.1$^{7,13}$]octasiloxane-1-yl)propyl(meth)acrylate, 3-(3,5,7,9,11,13,15-heptaphenylpentacyclo[9.5.1.1$^{3,9}$.1$^{5,15}$.1$^{7,13}$]-octasiloxane-1-yl)propyl(meth)acrylate, 3-[(3,5,7,9,11,13,15-heptaethylpentacyclo-[9.5.1.1$^{3,9}$.1$^{5,15}$.1$^{7,13}$]octasiloxane-1-yloxy)dimethylsilyl]propyl(meth)acrylate, 3-[(3,5,7,9,11,13,15-heptaisobutylpentacyclo-[9.5.1.1$^{3,9}$.1$^{5,15}$.1$^{7,13}$]octasiloxane-1-yloxy)dimethylsilyl]propyl(meth)acrylate, 3-[(3,5,7,9,11,13,15-heptaisooctylpentacyclo-[9.5.1.1$^{3,9}$.1$^{5,15}$.1$^{7,13}$]octasiloxane-1-yloxy)dimethylsilyl]propyl(meth)acrylate, 3-[(3,5,7,9,11,13,15-heptacyclopentylpentacyclo-[9.5.1.1$^{3,9}$.1$^{5,15}$.1$^{7,13}$]octasiloxane-1-yloxy)dimethylsilyl]propyl(meth)acrylate, 3-[(3,5,7,9,11,13,15-heptaphenylpentacyclo-[9.5.1.1$^{3,9}$.1$^{5,15}$.1$^{7,13}$]octasiloxane-1-yloxy)-dimethylsilyl]propyl(meth)acrylate, ethylene oxide adducts of (meth)acrylic acid, trifluoromethylmethyl(meth)acrylate, 2-trifluoromethylethyl (meth)acrylate, 2-perfluoroethylethyl(meth)acrylate, 2-perfluoroethyl-2-perfluorobutylethyl(meth)acrylate, 2-perfluoroethyl(meth)acrylate, trifluoromethyl(meth)acrylate, diperfluoromethylmethyl (meth)acrylate, 2-perfluoromethyl-2-perfluoroethylethyl(meth)acrylate, 2-perfluorohexylethyl (meth)acrylate, 2-perfluorodecylethyl(meth)acrylate, 2-perfluorohexadecylethyl(meth)acrylate, styrene, vinyltoluene, α-methylstyrene, p-chlorostyrene, p-chloromethylstyrene, m-chloromethylstyrene, o-aminostyrene, p-styrenechlorosulfonic acid, styrenesulfonic acid and salts thereof, vinylphenylmethyl dithiocarbamate, 2-(2-bromopropionylyloxy)styrene, 2-(2-bromo-isobutyryloxy)styrene, 1-(2-((4-vinylphenyl)-methoxy)-1-phenylethoxy)-2,2,6,6-tetramethyl-piperidine, 1-(4-vinylphenyl)-3,5,7,9,11,13,15-heptaethylpentacyclo-[9.5.1.1$^{3,9}$.1$^{5,15}$.1$^{7,13}$]-octasiloxane, 1-(4-vinylphenyl)-3,5,7,9,11,13,15-heptaisobutylpentacyclo[9.5.1.1$^{3,9}$.1$^{5,15}$.1$^{7,13}$]-octasiloxane, 1-(4-vinylphenyl)-3,5,7,9,11,13,15-heptaisooctylpentacyclo[9.5.1.1$^{3,9}$.1$^{5,15}$.1$^{7,13}$]-octasiloxane, 1-(4-vinylphenyl)-3,5,7,9,11,13,15-heptacyclopentylpentacyclo[9.5.1.1$^{3,9}$.1$^{5,15}$.1$^{7,13}$]-octasiloxane, 1-(4-vinylphenyl)-3,5,7,9,11,13,15-heptaphenylpentacyclo[9.5.1.1$^{3,9}$.1$^{5,15}$.1$^{7,13}$]-octasiloxane, 3-(3,5,7,9,11,13,15-heptaethylpentacyclo[9.5.1.1$^{3,9}$.1$^{5,15}$.1$^{7,13}$]octasiloxane-1-yl)ethylstyrene, 3-(3,5,7,9,11,13,15-heptaisobutylpentacyclo[9.5.1.1$^{3,9}$.1$^{5,15}$.1$^{7,13}$]-octasiloxane-1-yl)ethylstyrene, 3-(3,5,7,9,11,13,15-heptaisooctylpentacyclo[9.5.1.1$^{3,9}$.1$^{5,15}$.1$^{7,13}$]-octasiloxane-1-yl)ethylstyrene, 3-(3,5,7,9,11,13,15-heptacyclopentylpentacyclo[9.5.1.1$^{3,9}$.1$^{5,15}$.1$^{7,13}$]-octasiloxane-1-yl)ethylstyrene, 3-(3,5,7,9,11,13,15-heptaphenylpentacyclo[9.5.1.1$^{3,9}$.1$^{5,15}$.1$^{7,13}$]-octasiloxane-1-yl)ethylstyrene, 3-((3,5,7,9,11,13,15-heptaethylpentacyclo[9.5.1.1$^{3,9}$.1$^{5,15}$.1$^{7,13}$]octasiloxane-1-yloxy)dimethylsilyl)ethylstyrene, 3-((3,5,7,9,11,13,15-heptaisobutylpentacyclo-[9.5.1.1$^{3,9}$.1$^{5,15}$.1$^{7,13}$]octasiloxane-1-yloxy)dimethylsilyl)ethylstyrene, 3-((3,5,7,9,11,13,15-heptaisooctylpentacyclo-[9.5.1.1$^{3,9}$.1$^{5,15}$.1$^{7,13}$]octasiloxane-1-yloxy)-dimethylsilyl)ethylstyrene, 3-((3,5,7,9,11,13,15-heptacyclopentylpentacyclo[9.5.1.1$^{3,9}$.1$^{5,15}$.1$^{7,13}$]-octasiloxane-1-yloxy)dimethylsilyl)ethylstyrene, and 3-((3,5,7,9,11,13,15-heptaphenylpentacyclo-[9.5.1.1$^{3,9}$.1$^{5,15}$.1$^{7,13}$]octasiloxane-1-yloxy)dimethylsilyl)ethylstyrene.

26. A polymer obtained by polymerizing an addition-polymerizable monomer using the silicon compound as described in claim 11 as an initiator and using a transition metal complex as a catalyst, wherein the addition-polymerizable monomer is at least one member selected from the group consisting of (meth)acrylic acid, methyl (meth)acrylate, ethyl(meth)acrylate, n-propyl(meth)acrylate, isopropyl (meth)acrylate, n-butyl (meth)acrylate, isobutyl(meth)acrylate, tert-butyl(meth)acrylate, n-pentyl(meth)acrylate, n-hexyl (meth)acrylate, cyclohexyl(meth)acrylate, n-heptyl (meth)acrylate, n-octyl(meth)acrylate, 2-ethylhexyl(meth) acrylate, nonyl(meth)acrylate, decyl(meth)acrylate, dodecyl (meth)acrylate, phenyl(meth)acrylate, toluoyl(meth) acrylate, benzyl(meth)acrylate, 2-methoxyethyl (meth) acrylate, 3-methoxypropyl(meth)acrylate, 3-methoxybutyl (meth)acrylate, 2-hydroxyethyl (meth)acrylate, 2-hydroxypropyl(meth)acrylate, stearyl(meth)acrylate, glycidyl(meth)acrylate, 3-ethyl-3-(meth)acryloyloxymethyloxetane, 2-(meth)acryloyloxyethylisocyanate, 2-aminoethyl (meth)acrylate, 2-(2-bromopropionylyloxy)ethyl(meth) acrylate, 2-(2-bromoisobutyryloxy)ethyl (meth)acrylate, 1-(meth)acryloxy-2-phenyl-2-(2,2,6,6-tetramethyl-piperidinyloxy)ethane, (1-(4-((4-(meth)acryloxy)ethoxyethyl)phenylethoxy)piperidine, γ-(methacryloyloxypropyl)trimethoxysilane, 3-(3,5,7,9,11,13,15-heptaethylpentacyclo-[9.5.1.1$^{3,9}$.1$^{5,15}$.1$^{7,13}$]octasiloxane-1-yl)propyl(meth)acrylate, 3-(3,5,7,9,11,13,15-heptaisobutyl-pentacyclo[9.5.1.1$^{3,9}$.1$^{5,15}$.1$^{7,13}$]octasiloxane-1-yl)propyl(meth)acrylate, 3-(3,5,7,9,11,13,15-heptaisooctylpentacyclo[9.5.1.1$^{3,9}$.1$^{5,15}$.1$^{7,13}$]-octasiloxane-1-yl)propyl (meth)acrylate, 3-(3,5,7,9,11,13,15-heptacyclopentylpentacyclo-[9.5.1.1$^{3,9}$.1$^{5,15}$.1$^{7,13}$]octasiloxane-1-yl)propyl(meth)acrylate, 3-(3,5,7,9,11,13,15-heptaphenylpentacyclo[9.5.1.1$^{3,9}$.1$^{5,15}$.1$^{7,13}$]-octasiloxane-1-yl)propyl(meth)acrylate, 3-[(3,5,7,9,11,13,15-heptaethylpentacyclo-[9.5.1.1$^{3,9}$.1$^{5,15}$.1$^{7,13}$]octasiloxane-1-yloxy)dimethylsilyl]propyl(meth)acrylate, 3-[(3,5,7,9,11,13,15-heptaisobutylpentacyclo-[9.5.1.1$^{3,9}$.1$^{5,15}$.1$^{7,13}$]octasiloxane-1-yloxy)dimethylsilyl]propyl(meth)acrylate, 3-[(3,5,7,9,11,13,15-heptaisooctylpentacyclo-[9.5.1.1$^{3,9}$.1$^{5,15}$.1$^{7,13}$]octasiloxane-1-yloxy)dimethylsilyl]propyl(meth)acrylate, 3-[(3,5,7,9,11,13,15-heptacyclopentylpentacyclo-[9.5.1.1$^{3,9}$.1$^{5,15}$.1$^{7,13}$]

octasiloxane-1-yloxy)dimethylsilyl]propyl(meth)acrylate, 3-[(3,5,7,9,11,13,15-heptaphenylpentacyclo-[9.5.1.1$^{3,9}$.1$^{5,15}$.1$^{7,13}$]octasiloxane-1-yloxy)-dimethylsilyl]propyl (meth)acrylate, ethylene oxide adducts of (meth)acrylic acid, trifluoromethylmethyl(meth)acrylate, 2-trifluoromethylethyl (meth)acrylate, 2-perfluoroethylethyl(meth)acrylate, 2-perfluoroethyl-2-perfluorobutylethyl(meth)acrylate, 2-perfluoroethyl(meth)acrylate, trifluoromethyl(meth)acrylate, diperfluoromethylmethyl (meth)acrylate, 2-perfluoromethyl-2-perfluoroethylethyl(meth)acrylate, 2-perfluorohexylethyl (meth)acrylate, 2-perfluorodecylethyl(meth)acrylate, 2-perfluorohexadecylethyl(meth)acrylate, styrene, vinyltoluene, α-methylstyrene, p-chlorostyrene, p-chloromethylstyrene, m-chloromethylstyrene, o-aminostyrene, p-styrenechlorosulfonic acid, styrenesulfonic acid and salts thereof, vinylphenylmethyl dithiocarbamate, 2-(2-bromopropionyloxy)styrene, 2-(2-bromo-isobutyryloxy)styrene, 1-(2-((4-vinylphenyl)-methoxy)-1-phenylethoxy)-2,2,6,6-tetramethyl-piperidine, 1-(4-vinylphenyl)-3,5,7,9,11,13,15-heptaethylpentacyclo-[9.5.1.1$^{3,9}$.1$^{5,15}$.1$^{7,13}$]-octasiloxane, 1-(4-vinylphenyl)-3,5,7,9,11,13,15-heptaisobutylpentacyclo[9.5.1.1$^{3,9}$.1$^{5,15}$.1$^{7,13}$]-octasiloxane, 1-(4-vinylphenyl)-3,5,7,9,11,13,15-heptaisooctylpentacyclo[9.5.1.1$^{3,9}$.1$^{5,15}$.1$^{7,13}$]-octasiloxane, 1-(4-vinylphenyl)-3,5,7,9,11,13,15-heptacyclopentylpentacyclo[9.5.1.1$^{3,9}$.1$^{5,15}$.1$^{7,13}$]-octasiloxane, 1-(4-vinylphenyl)-3,5,7,9,11,13,15-heptaphenylpentacyclo[9.5.1.1$^{3,9}$.1$^{5,15}$.1$^{7,13}$]-octasiloxane, 3-(3,5,7,9,11,13,15-heptaethylpentacyclo[9.5.1.1$^{3,9}$.1$^{5,15}$.1$^{7,13}$]octasiloxane-1-yl)ethylstyrene, 3-(3,5,7,9,11,13,15-heptaisobutylpentacyclo[9.5.1.1$^{3,9}$.1$^{5,15}$.1$^{7,13}$]-octasiloxane-1-yl)ethylstyrene, 3-(3,5,7,9,11,13,15-heptaisooctylpentacyclo[9.5.1.1$^{3,9}$.1$^{5,15}$.1$^{7,13}$]-octasiloxane-1-yl)ethylstyrene, 3-(3,5,7,9,11,13,15-heptacyclopentylpentacyclo[9.5.1.1$^{3,9}$.1$^{5,15}$.1$^{7,13}$]-octasiloxane-1-yl)ethylstyrene, 3-(3,5,7,9,11,13,15-heptaphenylpentacyclo[9.5.1.1$^{3,9}$.1$^{5,15}$.1$^{7,13}$]-octasiloxane-1-yl)ethylstyrene, 3-((3,5,7,9,11,13,15-heptaethylpentacyclo[9.5.1.1$^{3,9}$.1$^{5,15}$.1$^{7,13}$]octasiloxane-1-yloxy)dimethylsilyl)ethylstyrene, 3-((3,5,7,9,11,13,15-heptaisobutylpentacyclo-[9.5.1.1$^{3,9}$.1$^{5,15}$.1$^{7,13}$]octasiloxane-1-yloxy)dimethylsilyl)ethylstyrene, 3-((3,5,7,9,11,13,15-heptaisooctylpentacyclo-[9.5.1.1$^{3,9}$.1$^{5,15}$.1$^{7,13}$]octasiloxane-1-yloxy)-dimethylsilyl)ethylstyrene, 3-((3,5,7,9,11,13,15-heptacyclopentylpentacyclo[9.5.1.1$^{3,9}$.1$^{5,15}$.1$^{7,13}$]-octasiloxane-1-yloxy)dimethylsilyl)ethylstyrene, and 3-((3,5,7,9,11,13,15-heptaphenylpentacyclo-[9.5.1.1$^{3,9}$.1$^{5,15}$.1$^{7,13}$]octasiloxane-1-yloxy)dimethylsilyl)ethylstyrene.

27. The silicon compound as described in claim 11, wherein X$^1$ is bromine.

* * * * *